US011678883B2

(12) United States Patent
Harris et al.

(10) Patent No.: US 11,678,883 B2
(45) Date of Patent: Jun. 20, 2023

(54) COMPRESSIBLE KNITTED ADJUNCTS WITH VARYING INTERCONNECTIONS

(71) Applicant: Cilag GmbH International, Zug (CH)

(72) Inventors: Jason L. Harris, Lebanon, OH (US); Michael J. Vendely, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 133 days.

(21) Appl. No.: 17/104,473

(22) Filed: Nov. 25, 2020

(65) Prior Publication Data

US 2022/0160360 A1 May 26, 2022

(51) Int. Cl.
*A61B 17/072* (2006.01)
(52) U.S. Cl.
CPC .......... *A61B 17/07292* (2013.01); *A61B 2017/07264* (2013.01); *A61B 2017/07271* (2013.01); *A61B 2017/07278* (2013.01); *A61B 2017/07285* (2013.01)
(58) Field of Classification Search
CPC .... A61B 17/07292; A61B 2017/07264; A61B 2017/07271; A61B 2017/07278; A61B 2017/07285; A61B 2017/00004; A61B 2017/00964
USPC ........................................... 227/175.1–182.1
See application file for complete search history.

(56) References Cited

U.S. PATENT DOCUMENTS

| D297,764 | S | 9/1988 | Hunt et al. |
| 4,892,244 | A | 1/1990 | Fox et al. |
| RE34,519 | E | 1/1994 | Fox et al. |
| 5,542,594 | A | 8/1996 | McKean et al. |
| 5,690,675 | A | 11/1997 | Sawyer et al. |
| 5,698,213 | A | 12/1997 | Jamiolkowski et al. |
| 5,700,583 | A | 12/1997 | Jamiolkowski et al. |
| 5,814,057 | A * | 9/1998 | Oi ........................ A61B 17/072 606/139 |
| 6,147,135 | A | 11/2000 | Yuan et al. |
| 6,325,810 | B1 | 12/2001 | Hamilton et al. |

(Continued)

FOREIGN PATENT DOCUMENTS

| EP | 0449431 A2 | 10/1991 |
| EP | 2008595 A2 | 12/2008 |

(Continued)

OTHER PUBLICATIONS

U.S. Appl. No. 17/104,413, filed Nov. 25, 2020, Compressible Knitted Adjuncts with Finished Edges.

(Continued)

*Primary Examiner* — Robert F Long
(74) *Attorney, Agent, or Firm* — Mintz Levin Cohn Ferris Glovsky and Popeo, P.C.

(57) ABSTRACT

Stapling assemblies for use with a surgical stapler are provided. In one exemplary embodiment, a stapling assembly can include a cartridge and a knitted adjunct that is configured to be releasably retained on the cartridge. The adjunct can include at least one knitted layer formed of first fibers and at least one core layer formed of second fibers that are interconnected with the first fibers to form a plurality of interconnections, in which one of the plurality of interconnections differs from at least another one of the plurality of interconnections to provide a variable compression strength.

19 Claims, 27 Drawing Sheets

(56) References Cited

U.S. PATENT DOCUMENTS

| | | | |
|---|---|---|---|
| 6,736,823 B2 | 5/2004 | Darois et al. |
| 7,143,924 B2 | 12/2006 | Scirica et al. |
| 7,143,925 B2 | 12/2006 | Shelton, IV et al. |
| 7,192,604 B2 | 3/2007 | Brown et al. |
| 7,641,091 B2 | 1/2010 | Olson et al. |
| 7,772,352 B2 | 8/2010 | Bezwada |
| 8,317,070 B2 | 11/2012 | Hueil et al. |
| 8,393,514 B2 | 3/2013 | Shelton, IV et al. |
| 8,551,058 B2 | 10/2013 | Measamer et al. |
| 8,590,762 B2 | 11/2013 | Hess et al. |
| 9,307,965 B2 | 4/2016 | Ming et al. |
| 9,332,984 B2 | 5/2016 | Weaner et al. |
| 9,445,808 B2 | 9/2016 | Woodard, Jr. et al. |
| 9,615,826 B2 | 4/2017 | Shelton, IV et al. |
| 9,700,311 B2 | 7/2017 | Shelton, IV et al. |
| 9,801,630 B2 | 10/2017 | Harris et al. |
| 9,826,965 B2 | 11/2017 | Stokes et al. |
| 9,848,871 B2 | 12/2017 | Harris et al. |
| 9,913,642 B2 | 3/2018 | Leimbach et al. |
| 9,913,646 B2 | 3/2018 | Shelton, IV |
| 9,924,944 B2 | 3/2018 | Shelton, IV et al. |
| 9,924,946 B2 | 3/2018 | Vendely et al. |
| 9,936,950 B2 | 4/2018 | Shelton, IV et al. |
| 9,936,954 B2 | 4/2018 | Shelton, IV et al. |
| 10,028,744 B2 | 7/2018 | Shelton, IV et al. |
| 10,052,104 B2 | 8/2018 | Shelton, IV et al. |
| D831,209 S | 10/2018 | Huitema et al. |
| D836,198 S | 12/2018 | Harris et al. |
| 10,166,026 B2 | 1/2019 | Shelton, IV et al. |
| 10,172,611 B2 | 1/2019 | Shelton, IV et al. |
| 10,172,616 B2 | 1/2019 | Murray et al. |
| 10,206,686 B2 | 2/2019 | Swayze et al. |
| 10,271,849 B2 | 4/2019 | Vendely et al. |
| 10,390,828 B2 | 8/2019 | Vendely et al. |
| 10,426,481 B2 | 10/2019 | Aronhalt et al. |
| 10,441,285 B2 | 10/2019 | Shelton, IV et al. |
| 10,456,129 B2 | 10/2019 | Shelton, IV et al. |
| 10,610,226 B2 | 4/2020 | Shelton, IV et al. |
| D885,574 S | 5/2020 | Shelton, IV et al. |
| 10,682,140 B2 | 6/2020 | Ingmanson et al. |
| 10,695,061 B2 | 6/2020 | Vendely et al. |
| 10,952,724 B2 | 3/2021 | Shelton, IV et al. |
| 10,959,721 B2 | 3/2021 | Shelton, IV et al. |
| 10,966,713 B2 | 4/2021 | Shelton, IV et al. |
| 10,980,533 B2 | 4/2021 | Shelton, IV et al. |
| 11,026,686 B2 | 6/2021 | Aranyi |
| 11,155,946 B2 | 10/2021 | Vendely et al. |
| D940,318 S | 1/2022 | Shelton, IV et al. |
| 11,272,932 B2 | 3/2022 | Aranyi |
| 11,446,027 B2 | 9/2022 | Harris et al. |
| 2005/0059997 A1 | 3/2005 | Bauman et al. |
| 2005/0245965 A1 | 11/2005 | Orban, III et al. |
| 2006/0084930 A1 | 4/2006 | Dhanaraj et al. |
| 2006/0257458 A1 | 11/2006 | Gorman et al. |
| 2008/0003913 A1 | 1/2008 | Vinson et al. |
| 2008/0140115 A1 | 6/2008 | Stopek |
| 2009/0001122 A1 | 1/2009 | Prommersberger et al. |
| 2009/0090763 A1 | 4/2009 | Zemlok et al. |
| 2009/0234193 A1 | 9/2009 | Weisenburgh, II et al. |
| 2009/0270686 A1 | 10/2009 | Duke et al. |
| 2010/0023056 A1* | 1/2010 | Johansson | A61B 17/0401 |
| | | | 606/232 |
| 2010/0036441 A1* | 2/2010 | Procter | A61L 27/502 |
| | | | 606/329 |
| 2011/0087279 A1* | 4/2011 | Shah | A61B 17/07207 |
| | | | 606/219 |
| 2011/0192882 A1 | 8/2011 | Hess et al. |
| 2012/0024934 A1 | 2/2012 | Shelton, IV et al. |
| 2012/0080335 A1 | 4/2012 | Shelton, IV et al. |
| 2012/0080344 A1 | 4/2012 | Shelton, IV |
| 2012/0083835 A1 | 4/2012 | Shelton, IV et al. |
| 2012/0187179 A1 | 7/2012 | Gleiman |
| 2012/0241502 A1 | 9/2012 | Aldridge et al. |
| 2013/0013074 A1 | 1/2013 | Shikinami |
| 2013/0112731 A1 | 5/2013 | Hodgkinson |
| 2013/0112733 A1 | 5/2013 | Aranyi et al. |
| 2013/0146642 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0161375 A1 | 6/2013 | Huitema et al. |
| 2013/0256365 A1 | 10/2013 | Shelton, IV et al. |
| 2013/0256372 A1 | 10/2013 | Baxter, III et al. |
| 2013/0256376 A1 | 10/2013 | Barton et al. |
| 2013/0256377 A1 | 10/2013 | Schmid et al. |
| 2013/0317526 A1 | 11/2013 | Mortarino |
| 2014/0158741 A1 | 6/2014 | Woodard, Jr. et al. |
| 2014/0158742 A1 | 6/2014 | Stopek et al. |
| 2014/0205637 A1 | 7/2014 | Widenhouse et al. |
| 2014/0224686 A1 | 8/2014 | Aronhalt et al. |
| 2014/0224857 A1 | 8/2014 | Schmid |
| 2014/0277575 A1 | 9/2014 | Landgrebe et al. |
| 2015/0034696 A1 | 2/2015 | Shelton, IV et al. |
| 2015/0099098 A1 | 4/2015 | Bahukudumbi et al. |
| 2015/0099140 A1 | 4/2015 | Amata et al. |
| 2015/0099410 A1 | 4/2015 | Bahukudumbi et al. |
| 2015/0108199 A1 | 4/2015 | Shelton, IV et al. |
| 2015/0134076 A1 | 5/2015 | Shelton, IV et al. |
| 2015/0134077 A1 | 5/2015 | Shelton, IV et al. |
| 2015/0173756 A1 | 6/2015 | Baxter, III et al. |
| 2015/0196299 A1 | 7/2015 | Swayze et al. |
| 2015/0272575 A1 | 10/2015 | Leimbach et al. |
| 2015/0297222 A1 | 10/2015 | Huitema et al. |
| 2015/0313594 A1 | 11/2015 | Shelton, IV et al. |
| 2015/0351753 A1 | 12/2015 | Shelton, IV et al. |
| 2015/0351754 A1 | 12/2015 | Harris et al. |
| 2015/0351758 A1 | 12/2015 | Shelton, IV et al. |
| 2016/0000430 A1 | 1/2016 | Ming et al. |
| 2016/0106427 A1 | 4/2016 | Shelton, IV et al. |
| 2016/0174974 A1 | 6/2016 | Schmid et al. |
| 2017/0055981 A1 | 3/2017 | Vendely et al. |
| 2017/0056000 A1 | 3/2017 | Nalagatla et al. |
| 2017/0056566 A1 | 3/2017 | Shelton, IV et al. |
| 2017/0086827 A1 | 3/2017 | Vendely et al. |
| 2017/0086829 A1* | 3/2017 | Vendely | D01D 5/0023 |
| 2017/0086835 A1 | 3/2017 | Harris et al. |
| 2017/0086837 A1 | 3/2017 | Vendely et al. |
| 2017/0086838 A1 | 3/2017 | Harris et al. |
| 2017/0086841 A1* | 3/2017 | Vendely | A61B 17/068 |
| 2017/0086843 A1 | 3/2017 | Vendely et al. |
| 2017/0216535 A1 | 8/2017 | Mao |
| 2017/0231633 A1 | 8/2017 | Marczyk et al. |
| 2018/0235626 A1* | 8/2018 | Shelton, IV | A61B 17/07292 |
| 2019/0038280 A1 | 2/2019 | Shelton, IV et al. |
| 2019/0059889 A1 | 2/2019 | Shelton, IV et al. |
| 2019/0254659 A1 | 8/2019 | Harris et al. |
| 2019/0254664 A1 | 8/2019 | Vendely et al. |
| 2019/0254665 A1 | 8/2019 | Vendely et al. |
| 2019/0254666 A1 | 8/2019 | Vendely et al. |
| 2019/0254667 A1 | 8/2019 | Vendely et al. |
| 2019/0254668 A1 | 8/2019 | Vendely et al. |
| 2019/0254669 A1 | 8/2019 | Shelton, IV et al. |
| 2020/0197006 A1 | 6/2020 | Shelton, IV et al. |
| 2020/0205806 A1 | 7/2020 | Shelton, IV et al. |
| 2021/0177418 A1 | 6/2021 | Shelton, IV et al. |
| 2021/0277555 A1 | 9/2021 | Vendely et al. |
| 2021/0315575 A1 | 10/2021 | Aranyi |
| 2021/0401433 A1 | 12/2021 | Freidel et al. |
| 2022/0015764 A1 | 1/2022 | Shelton, IV et al. |
| 2022/0039797 A1 | 2/2022 | Shelton, IV et al. |
| 2022/0133319 A1 | 5/2022 | Shelton, IV et al. |
| 2022/0133320 A1 | 5/2022 | Shelton, IV et al. |
| 2022/0133321 A1 | 5/2022 | Shelton, IV et al. |
| 2022/0160353 A1 | 5/2022 | Harris et al. |
| 2022/0160354 A1 | 5/2022 | Harris et al. |
| 2022/0160357 A1 | 5/2022 | Harris et al. |
| 2022/0160359 A1 | 5/2022 | Harris et al. |

FOREIGN PATENT DOCUMENTS

| | | |
|---|---|---|
| EP | 2644121 A2 | 10/2013 |
| EP | 2724734 A2 | 4/2014 |
| EP | 2954855 A1 | 12/2015 |
| EP | 2954857 A1 | 12/2015 |
| EP | 3135222 A1 | 3/2017 |

(56) References Cited

FOREIGN PATENT DOCUMENTS

| EP | 3150134 A1 * | 4/2017 | ....... A61B 17/00491 |
|---|---|---|---|
| EP | 3150143 A1 | 4/2017 | |
| EP | 3162384 A1 | 5/2017 | |
| EP | 3275378 A1 | 1/2018 | |
| EP | 3363386 A1 | 8/2018 | |
| JP | H1015640 A | 1/1998 | |
| JP | 2014117603 A | 6/2014 | |
| WO | 2014016819 A1 | 1/2014 | |
| WO | 2015191277 A2 | 12/2015 | |

OTHER PUBLICATIONS

U.S. Appl. No. 17/104,436, filed Nov. 25, 2020, Compressible Knitted Adjuncts with Surface Features.
U.S. Appl. No. 17/104,463, filed Nov. 25, 2020, Compressible Knitted Adjuncts with Finished Edges.
U.S. Appl. No. 17/104,488, filed Nov. 25, 2020, Compressible Knitted Adjuncts with Varying Fiber Features.
U.S. Appl. No. 16/119,292, filed Aug. 31, 2018, Adjunct Materials and Methods of Using Same in Surgical Methods for Tissue Sealing.
U.S. Appl. No. 16/806,252, filed Mar. 2, 2020, Adjunct Materialss and Methods of Using Same in Surgical Methods for Tissue Sealing.
U.S. Appl. No. 16/806,262, filed Mar. 2, 2020, Adjunct Materials and Methods of Using Same in Surgical Methods for Tissue Sealing.
U.S. Appl. No. 14/300,954, filed Jun. 10, 2014, Adjunct Materials and Methods of Using Same in Surgical Methods for Tissue Sealing.
U.S. Appl. No. 29/732,706, filed Apr. 27, 2020, Knitted Tissue Scaffold.
U.S. Appl. No. 15/901,103, filed Feb. 21, 2018, Knitted Tissue Scaffolds.
U.S. Appl. No. 15/901,245, filed Feb. 21, 2018, Knitted Tissue Scaffolds.
U.S. Appl. No. 15/901,613, filed Feb. 21, 2018, Knitted Tissue Scaffolds.
U.S. Appl. No. 15/901,632, filed Feb. 21, 2018, Knitted Tissue Scaffolds.
U.S. Appl. No. 15/901,647, filed Feb. 21, 2018, Knitted Tissue Scaffolds.
U.S. Appl. No. 15/901,668, filed Feb. 21, 2018, Knitted Tissue Scaffolds.
U.S. Appl. No. 29/637,760, filed Feb. 21, 2018, Knitted Tissue Scaffold.
Extended European Search Report received for EP Application No. 15171455.7, dated Sep. 30, 2015, 5 pages.
International Search Report and Written Opinion received for PCT Application No. PCT/IB2019/050505, dated Jun. 4, 2019, 11 pages.
International Search Report and Written Opinion received for PCT Application No. PCT/IB2019/050501, dated Jul. 31, 2019, 22 pages.
International Search Report and Written Opinion received for PCT Application No. PCT/IB2019/050502, dated Aug. 20, 2019, 20 pages.
International Search Report and Written Opinion received for PCT Application No. PCT/IB2019/050503, dated May 21, 2019, 12 pages.
International Search Report and Written Opinion received for PCT Application No. PCT/IB2019/050504, dated Jun. 4, 2019, 12 pages.
International Search Report and Written Opinion received for PCT Application No. PCT/IB2019/050506, dated Jun. 4, 2019, 11 pages.
Partial European Search Report received for EP Application No. 19158395.4, dated May 14, 2019, 8 pages.
Baker et al. (Nov. 2004) "The Science of Stapling and Leaks", Obesity Surgery, 14:1290-1298.
Chen et al. (2013) "Elastomeric Biomaterials for Tissue Engineering", Progress in Polymer Science, 38(3-4): 584-671.
Lim et al. (May 2012) "Fabrication and Evaluation of Poly(epsilon-Caprolactone)/Silk Fibroin Blend Nanofibrous Scaffold", Biopolymers, 97(5):265-275.
Ye et al. (2008) "Development of the Warp Knitted Spacer Fabrics for Cushion Applications", Journal of Industrial Textiles, 37(3):213-223.
Zhao et al. (Nov. 2007) "Biodegradable Fibrous Scaffolds Composed of Gelatin Coated Poly(ε-caprolactone) Prepared by Coaxial Electrospinning", Journal of Biomedical Materials Research, 83A(2): 372-382.

* cited by examiner

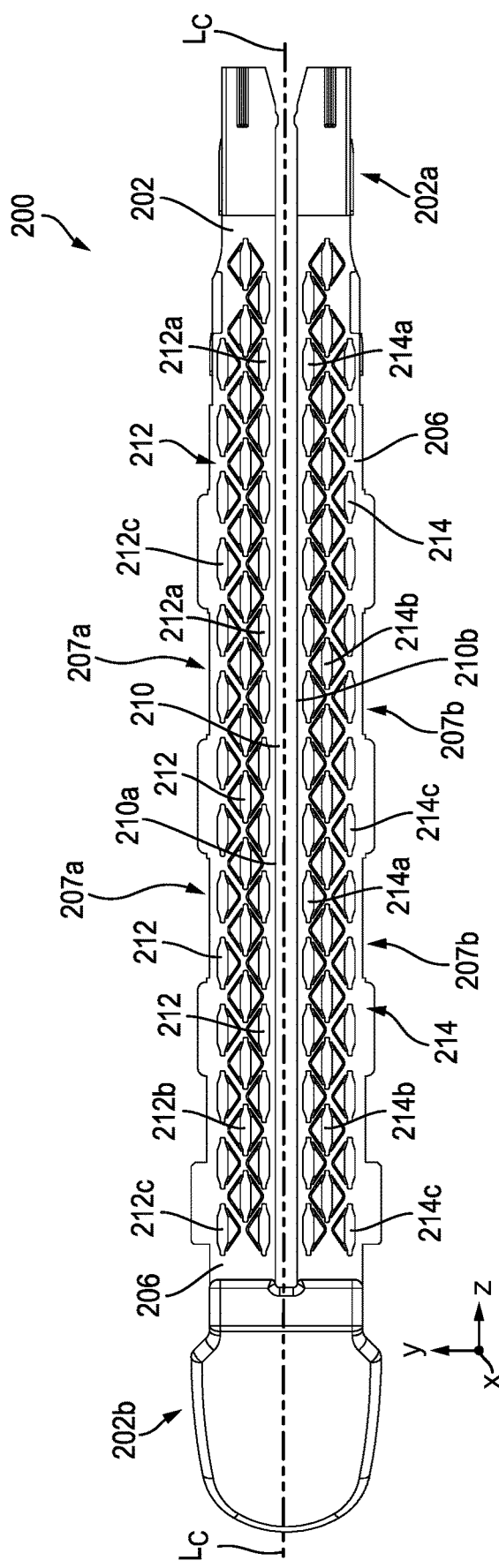
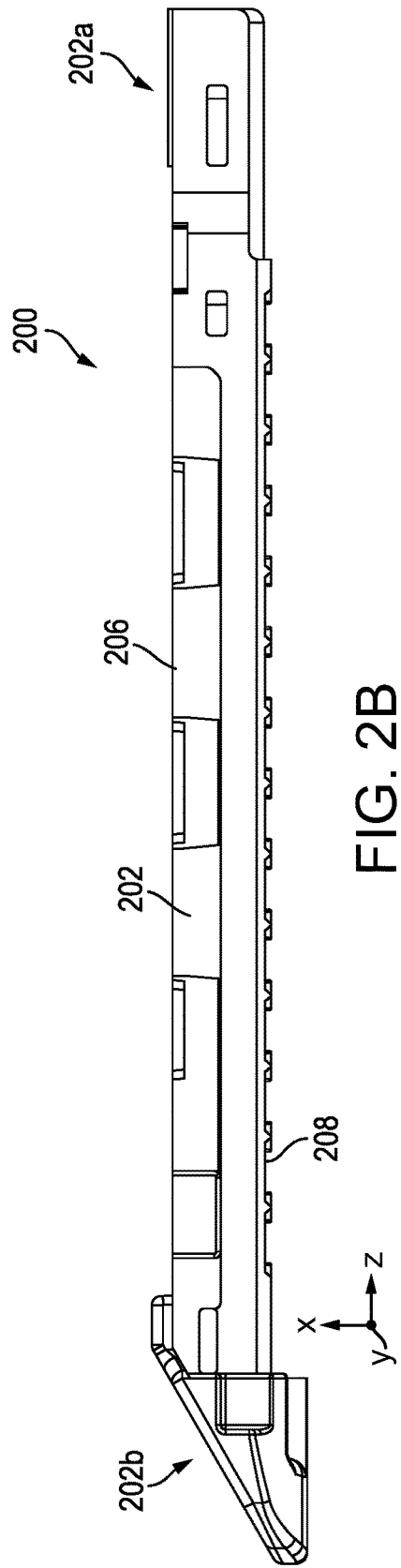
FIG. 2A
FIG. 2B

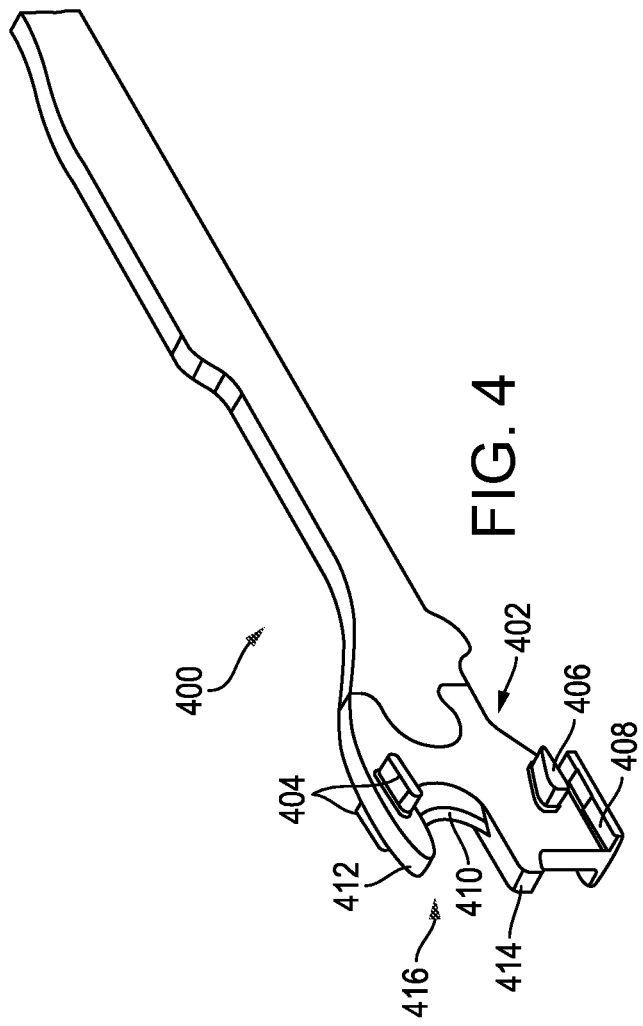
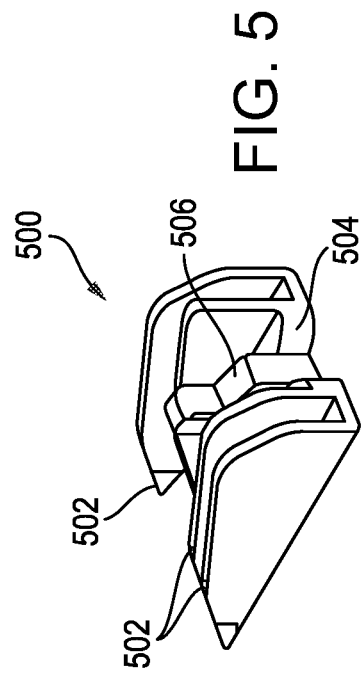
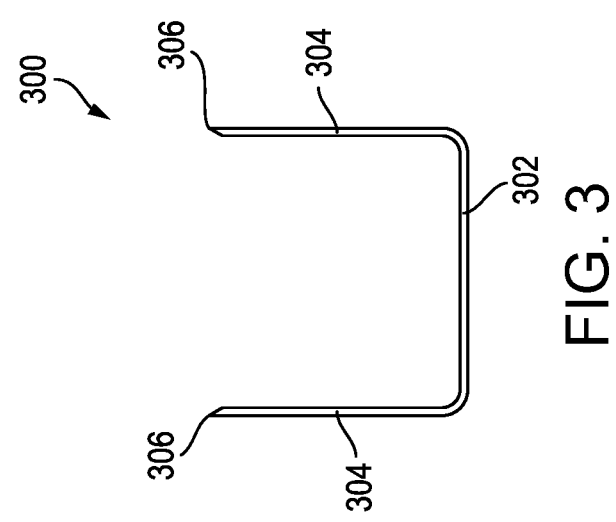

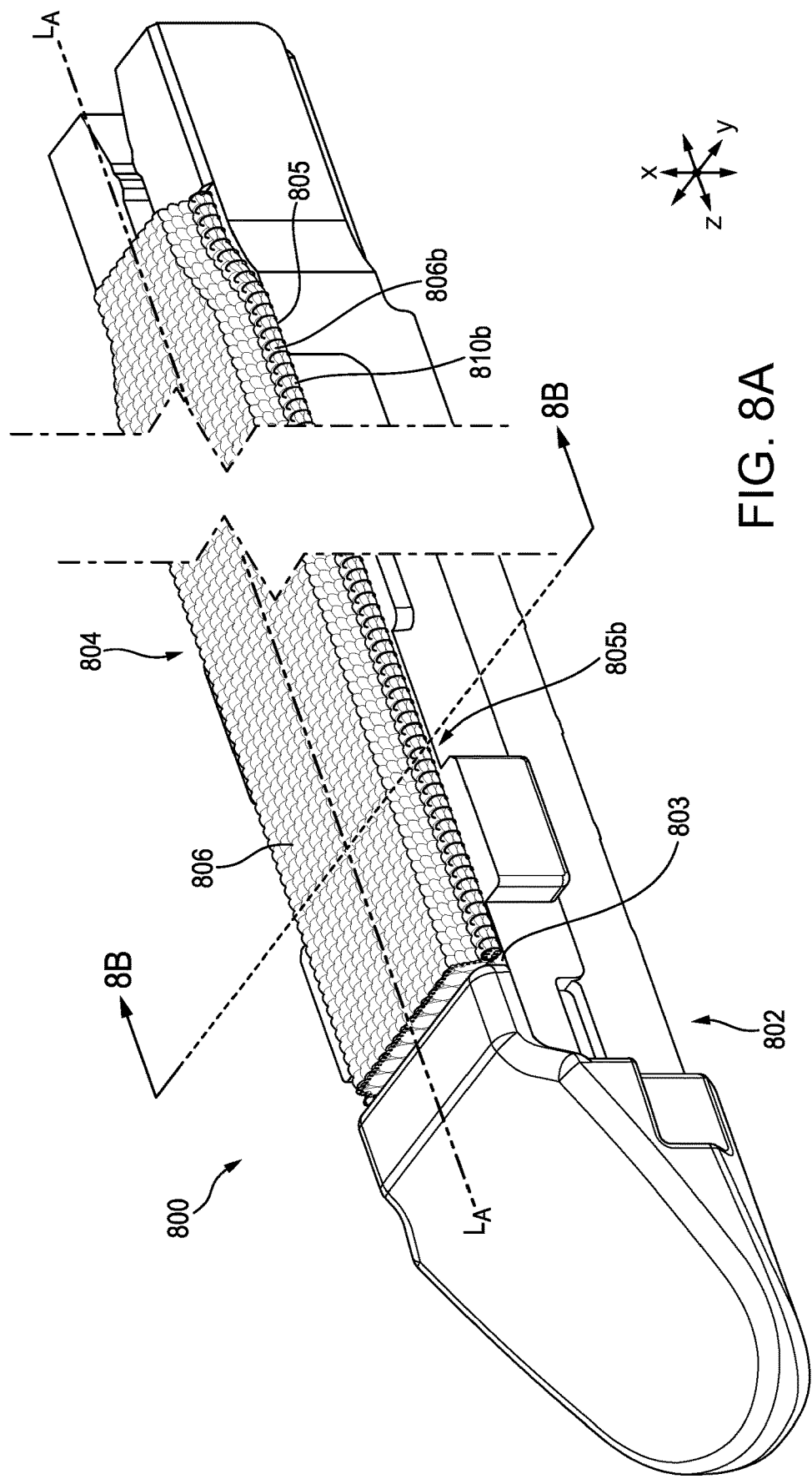

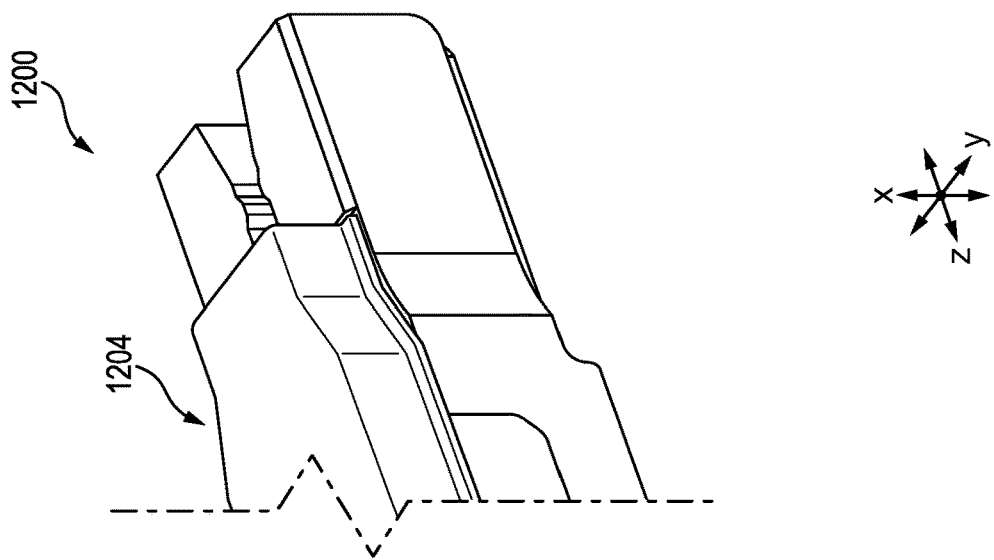
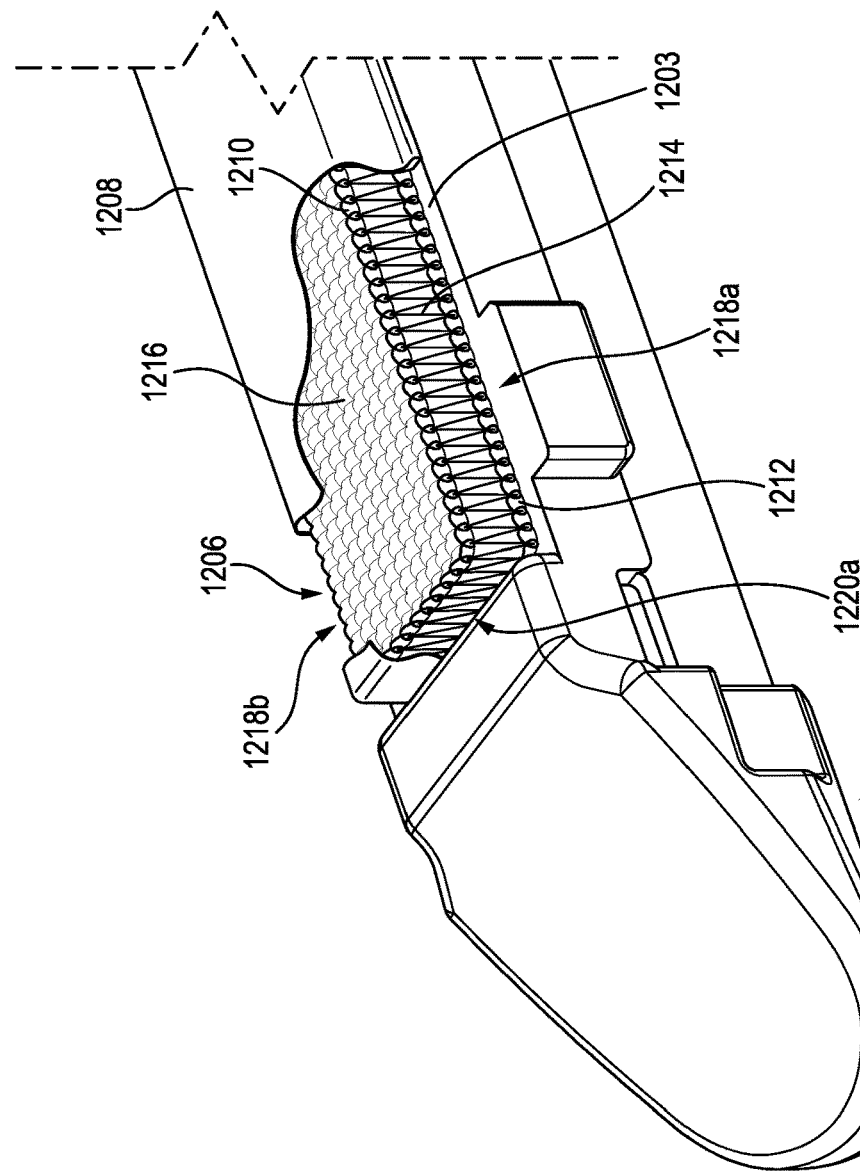
FIG. 12

COMPRESSIBLE KNITTED ADJUNCTS WITH VARYING INTERCONNECTIONS

FIELD

Compressible knitted adjuncts and methods of using the same are provided.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Some surgical staplers require a surgeon to select the appropriate staples having the appropriate staple height for the tissue being stapled. For example, a surgeon could select tall staples for use with thick tissue and short staples for use with thin tissue. In some instances, however, the tissue being stapled does not have a consistent thickness and, thus the staples cannot achieve the desired fired configuration at each staple site. As a result, a desirable seal at or near all of the stapled sites cannot be formed, thereby allowing blood, air, gastrointestinal fluids, and other fluids to seep through the unsealed sites.

Further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted, and therefore are unable to withstand the varying intra-tissue pressures at the implantation site. This can lead to undesirable tissue tearing, and consequently leakage, at or near the staple site.

Accordingly, there remains a need for improved devices and methods that address current issues with surgical staplers.

SUMMARY

Stapling assemblies for use with a surgical stapler are provided. In one exemplary embodiment, a stapling assembly includes a cartridge and a knitted adjunct. The cartridge has a plurality of staples disposed therein and configured to be deployed into tissue. The knitted adjunct is configured to be releasably retained on the cartridge such that the adjunct can be attached to tissue by the plurality of staples in the cartridge. The adjunct has a first end, a second end, and a longitudinal axis extending therebetween. The adjunct includes at least one knitted layer formed of first fibers and at least one core layer formed of second fibers that are interconnected with the first fibers to form a plurality of interconnections. One of the plurality of interconnections can differ from at least another one of the plurality of interconnections to provide a variable compression strength.

The plurality of interconnections can have a variety of configurations. For example, in some embodiments, the one of the plurality of interconnections that differs from the other one of the plurality of interconnections can differ in at least one of a lateral direction and a longitudinal direction relative to the longitudinal axis of the adjunct. In other embodiments, the plurality of interconnections can include a first plurality of interconnections and a second plurality of interconnections. In some embodiments, the first plurality of interconnections can each have a first tightness, and the second plurality of interconnections can each have a second tightness that is greater than the first tightness. In other embodiments, the first plurality of interconnections can be present in a first amount, and the second plurality of interconnections can be present in a second amount that is greater than the first amount.

In some embodiments, the cartridge can include a slot formed therein and extending along at least a portion of a longitudinal axis thereof, and the first plurality of interconnections can be proximate to the slot relative to the second plurality of interconnections.

The at least one knitted layer can have a variety of configurations. For example, in some embodiments, the at least one knitted layer can include third fibers that are interconnected with the first fibers and second fibers. In other embodiments, the at least one knitted layer can include a first knitted layer that is configured to contact the cartridge. In some embodiments, the at least one knitted layer can include a second knitted layer that is configured to contact tissue, and the at least one core layer can be positioned therebetween.

In some embodiments, the second fibers can be monofilament fibers.

In some embodiments, the core layer can also include third fibers that are interconnected with the second fibers.

In another exemplary embodiment, a stapling assembly for use with a surgical stapler includes a cartridge and a knitted adjunct. The cartridge has a plurality of staples disposed therein and configured to be deployed into tissue. The knitted adjunct is configured to be releasably retained on the cartridge such that the adjunct can be attached to tissue by the plurality of staples in the cartridge. The adjunct has a first end, a second end, and a longitudinal axis extending therebetween. The adjunct can include at least two different compression zones, and each compression zone can be formed of first fibers and second fibers that are interconnected to each other at knots. The knots of a first compression zone of the at least two different compression zones each have a first knot tightness and the knots of a second compression zone of the at least two different compression zones each have a second knot tightness that is greater than the first knot tightness such that the adjunct has a varying compression strength.

In some embodiments, the first compression zone can have a first fiber density and the second compression zone can have a second fiber density that is different than the first fiber density.

The second compression zone can have a variety of configurations. For example, in some embodiments, the second compression zone can be positioned about at least a portion of a perimeter of the adjunct, and the first compression zone can be internal to the perimeter. In other embodiments, the second compression zone can be configured to at least partially overlap with at least a portion of the plurality of staple when the adjunct is attached to the cartridge.

In some embodiments, at least one of the first compression zone and the second compression zone can include third fibers that are interconnected to the second fibers.

In some embodiments, the cartridge can include a slot formed therein and extending along at least a portion of a longitudinal axis thereof, and the first compression zone is configured to at least partially overlap with the slot when the adjunct is attached to the cartridge.

In some embodiments, the knots of the first compression zone can be present therein at a first frequency and the knots of the second compression zone can be present therein at a second frequency that is different than the first frequency.

In another exemplary embodiment, a stapling assembly for use with a surgical stapler includes a cartridge and a knitted adjunct. The cartridge has a plurality of staples disposed therein, in which the plurality of staples are configured to be deployed into tissue. The knitted adjunct is configured to be releasably retained on the cartridge such that the adjunct can be attached to tissue by the plurality of staples in the cartridge. The adjunct has a first end, a second end, and a longitudinal axis extending therebetween. The adjunct includes a tissue-contacting layer formed of at least first fibers, a cartridge-contacting layer formed of at least second fibers, and a core layer disposed between the tissue-contacting layer and the cartridge-contacting layer. The core layer can be formed of third fibers that are interconnected with the first fibers at a first tightness and with the second fibers at a second tightness that is different than the first tightness to allow the adjunct to compress in a first predetermined direction and to limit movement in a second direction that differs from the first predetermined direction.

In some embodiments, the first tightness can be greater than the second tightness. In other embodiments, the first tightness can be less than the second tightness.

In some embodiments, at least one of the tissue-contacting layer and the cartridge-contacting layer can include reinforcing fibers that are knotted to the second fibers to minimize lateral movement of the second fibers relative to the longitudinal axis of the adjunct.

BRIEF DESCRIPTION OF THE DRAWINGS

This invention will be more fully understood from the following detailed description taken in conjunction with the accompanying drawings, in which:

FIG. 2A is a top view of a staple cartridge for use with the surgical stapling and severing device of FIG. 1;

FIG. 2B is a side view of the staple cartridge of FIG. 2A;

FIG. 3 is a side view of a staple in an unfired (pre-deployed) configuration that can be disposed within the staple cartridge of the surgical cartridge assembly of FIG. 2A;

FIG. 4 is a perspective view of a knife and firing bar ("E-beam") of the surgical stapling and severing device of FIG. 1;

FIG. 5 is a perspective view of a wedge sled of a staple cartridge of the surgical stapling and severing device of FIG. 1;

FIG. 8A is a perspective view of an exemplary embodiment of a stapling assembly having a compressible knitted adjunct releasably retained on a staple cartridge;

FIG. 12 is a perspective view of another exemplary embodiment of stapling assembly having a compressible knitted adjunct;

DETAILED DESCRIPTION

Figure 1:
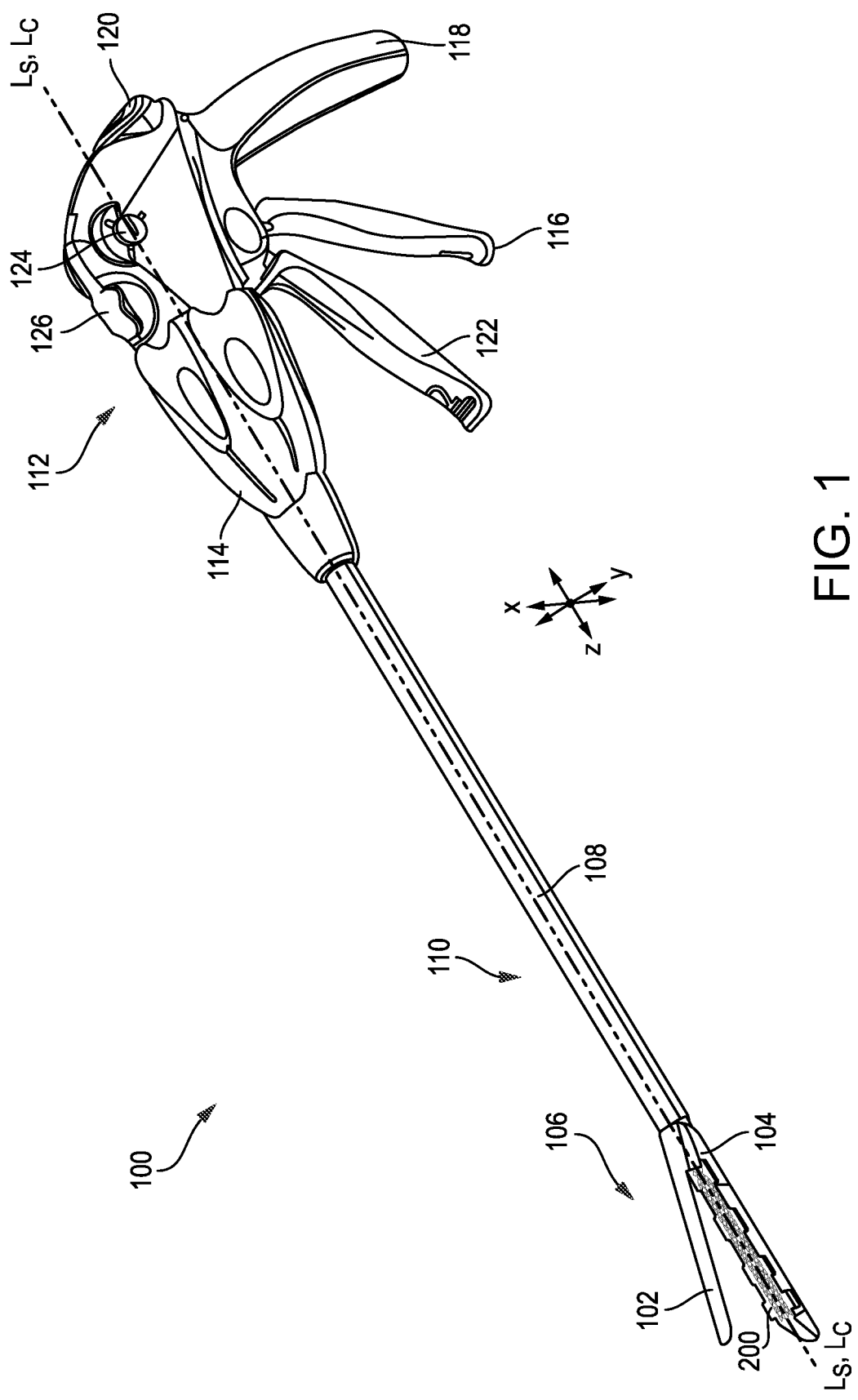
FIG. 1 is a perspective view of one exemplary embodiment of a conventional surgical stapling and severing device.

Certain exemplary embodiments will now be described to provide an overall understanding of the principles of the structure, function, manufacture, and use of the adjuncts, systems, and methods disclosed herein. One or more examples of these embodiments are illustrated in the accompanying drawings. Those skilled in the art will understand that the adjuncts, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Surgical stapling assemblies and methods for manufacturing and using the same are provided. In general, a surgical stapling assembly can include a staple cartridge having staples disposed therein and a compressible, knitted adjunct configured to be releasably retained on the staple cartridge. As discussed herein, the various adjuncts provided can be configured to compensate for variations in tissue properties, such as variations in tissue thickness, and/or to promote tissue ingrowth when the adjuncts are stapled to tissue. Further, the various adjuncts can be designed in such a way that inhibits the fraying and/or tearing thereof. This can improve the aesthetics and/or structural integrity of the adjunct.

An exemplary stapling assembly can include a variety of features to facilitate application of a surgical staple, as described herein and illustrated in the drawings. However, a person skilled in the art will appreciate that the stapling assembly can include only some of these features and/or it can include a variety of other features known in the art. Any stapling assembly known in the art can be used. The stapling assemblies described herein are merely intended to represent certain exemplary embodiments. Moreover, while the adjuncts are described in connection with surgical staple cartridge assemblies, the adjuncts can be used in connection with staple reloads that are not cartridge based or any type of surgical device.

FIG. 1 illustrates an exemplary surgical stapling and severing device 100 suitable for use with an implantable adjunct. The illustrated surgical stapling and severing device 100 includes a staple applying assembly 106 or end effector having an anvil 102 that is pivotably coupled to an elongate staple channel 104. As a result, the staple applying assembly 106 can move between an open position, as shown in FIG. 1, and a closed position in which the anvil 102 is positioned adjacent to the elongate staple channel 104 to engage tissue therebetween. The staple applying assembly 106 can be attached at its proximal end to an elongate shaft 108 forming an implement portion 110. When the staple applying assembly 106 is closed, or at least substantially closed, (e.g., the anvil 102 moves from the open position in FIG. 1 toward the elongate staple channel) the implement portion 110 can present a sufficiently small cross-section suitable for inserting the staple applying assembly 106 through a trocar. While the device 100 is configured to staple and sever tissue, surgical devices configured to staple but not sever tissue are also contemplated herein.

In various instances, the staple applying assembly 106 can be manipulated by a handle 112 connected to the elongate shaft 108. The handle 112 can include user controls such as a rotation knob 114 that rotates the elongate shaft 108 and the staple applying assembly 106 about a longitudinal axis of the elongate shaft 108, and a closure trigger 116 which can pivot relative to a pistol grip 118 to close the staple applying assembly 106. A closure release button 120 can be outwardly presented on the handle 112 when the closure trigger 116 is clamped such that the closure release button 120 can be depressed to unclamp the closure trigger 116 and open the staple applying assembly 106, for example.

A firing trigger 122, which can pivot relative to the closure trigger 116, can cause the staple applying assembly 106 to simultaneously sever and staple tissue clamped therein. In various instances, multiple firing strokes can be employed using the firing trigger 122 to reduce the amount of force required to be applied by the surgeon's hand per stroke. In certain embodiments, the handle 112 can include one or more rotatable indicator wheels such as, for example, rotatable indicator wheel 124 which can indicate the firing progress. A manual firing release lever 126 can allow the firing system to be retracted before full firing travel has been completed, if desired, and, in addition, the firing release lever 126 can allow a surgeon, or other clinician, to retract the firing system in the event that the firing system binds and/or fails.

Additional details on the surgical stapling and severing device 100 and other surgical stapling and severing devices suitable for use with the present disclosure are described, for example, in U.S. Pat. No. 9,332,984 and in U.S. Patent Publication No. 2009/0090763, the disclosures of which are incorporated herein by reference in their entireties. Further, the surgical stapling and severing device need not include a handle, but instead can have a housing that is configured to couple to a surgical robot, for example, as described in U.S. Patent Publication No. 2019/0059889, the disclosure of which is incorporated herein by reference in its entirety.

As further shown in FIG. 1, a staple cartridge 200 can be utilized with the device 100. In use, the staple cartridge 200 is placed within and coupled to the elongate staple channel 104. While the staple cartridge 200 can have a variety of configurations, in this illustrated embodiment, the staple cartridge 200, which is shown in more detail in FIGS. 2A-2B, has a proximal end 202a and a distal end 202b with a longitudinal axis $L_C$ extending therebetween. As a result, when the staple cartridge 200 is inserted into the elongate staple channel 104 (FIG. 1), the longitudinal axis $L_C$ aligns with the longitudinal axis Ls of the elongate shaft 108. Further, the staple cartridge 200 includes a longitudinal slot 210 defined by two opposing slot edges 210a, 210b and configured to receive at least a portion of a firing member of a firing assembly, like firing assembly 400 in FIG. 4, as discussed further below. As shown, the longitudinal slot 202 extends from the proximal end 202a toward the distal end 202b of the staple cartridge 200. It is also contemplated herein that in other embodiments, the longitudinal slot 202 can be omitted.

The illustrated staple cartridge 200 includes staple cavities 212, 214 defined therein and each staple cavity 212, 214 is configured to removably house at least a portion of a staple (not shown). The number, shape, and position of the staple cavities can vary and can depend at least on the size and shape of the staples to be removably disposed therein. In this illustrated embodiment, the staple cavities are arranged in two sets of three longitudinal rows, with the first set of staple cavities 212 positioned on a first side of the longitudinal slot 210 and the second set of staple cavities 214 positioned on a second side of the longitudinal slot 210. On each side of the longitudinal slot 210, and thus for each set of rows, a first longitudinal row of staple cavities 212a, 214a extends alongside the longitudinal slot 210, a second row of staple cavities 212b, 214b extends alongside the first row of staple cavities 212a, 214b, and a third row of staple cavities 212c, 214c extends alongside the second row of staple cavities 212b, 214b. For each set of rows, the first row of staple cavities 212a, 214b, the second row of staple cavities 212b, 214b, and the third row of staple cavities 214c, 214c are parallel to one another and the longitudinal slot 210. Further, as shown, for each set of rows, the second row of staple cavities 212b, 214b is staggered with respect to the first and third rows of staple cavities 212a, 212c, 214a, 214c. In other embodiments, the staple cavity rows in each set 212, 214 are not parallel to one another and/or the longitudinal slot 210.

The staples releasably stored in the staple cavities 212, 214 can have a variety of configurations. An exemplary staple 300 that can be releasably stored in each of the staple cavities 212, 214 is illustrated in FIG. 3 in its unfired (pre-deployed, unformed) configuration. The illustrated staple 300 includes a crown (base) 302 and two staple legs 304 extending from each end of the crown 302. In this embodiment, the crown 302 extends in a linear direction and the staple legs 304 have the same unformed height, whereas in other embodiments, the crown can be a step up crown, and/or the staple legs can have different unformed heights. Further, prior to the staples 300 being deployed, the crowns 302 can be supported by staple drivers that are positioned within the staple cartridge 200 and, concurrently, the staple legs 304 can be at least partially contained within the staple cavities 212, 214. Further, the staple legs 304 can extend beyond a top surface, like top surface 206, of the staple cartridge 200 when the staples 300 are in their unfired positions. In certain instances, as shown in FIG. 3, the tips 306 of the staple legs 304 can be pointed and sharp which can incise and penetrate tissue.

In use, staples 300 can be deformed from an unfired position into a fired position such that the staple legs 304 move through the staple cavities 212, 214, penetrate tissue positioned between the anvil 102 and the staple cartridge 200, and contact the anvil 102. As the staple legs 304 are deformed against the anvil 102, the staple legs 304 of each staple 300 can capture a portion of the tissue within each staple 300 and apply a compressive force to the tissue. Further, the staple legs 304 of each staple 300 can be deformed downwardly toward the crown 302 of the staple 300 to form a staple entrapment area in which the tissue can be captured therein. In various instances, the staple entrapment area can be defined between the inner surfaces of the deformed legs and the inner surface of the crown of the staple. The size of the entrapment area for a staple can depend on several factors such as the length of the legs, the diameter of the legs, the width of the crown, and/or the extent in which the legs are deformed, for example.

In some embodiments, all of the staples disposed within the staple cartridge 200 can have the same unfired (pre-deployed, unformed) configuration. In other embodiments, the staples can include at least two groups of staples each having a different unfired (pre-deployed, unformed) configuration, e.g., varying in height and/or shape, relative to one another, etc. For example, the staple cartridge 200 can include a first group of staples having a first height disposed within the first row of staple cavities 212a, 214a, a second group of staples having a second height disposed within the second row of staple cavities 212b, 214b, and a third group of staples having a third height disposed within the third row of staple cavities 212c, 214c. In some embodiments, the first, second, and third heights can be different, in which the third height is greater than the first height and the second height. In other embodiments, the first and second heights are the same, but the third height is different and greater than the first height and the second height. A person skilled in the art will appreciate that other combinations of staples are contemplated herein.

Further, the staples can include one or more external coatings, e.g., a sodium stearate lubricant and/or an antimicrobial agent(s). The antimicrobial agent(s) can be applied to the staples as its own coating or incorporated into another coating, such as a lubricant. Non-limiting examples of suitable antimicrobial agents include 5-Chloro-2-(2,4-dichlorophenoxy)phenol, chlorhexidine, silver formulations (e.g., nano-crystalline silver), lauric arginate ethyl ester (LAE), octenidine, polyhexamethylene biguanide (PHMB), taurolidine, lactic acid, citric acid, acetic acid, and their salts.

Referring back to FIGS. 2A-2B, the staple cartridge 200 extends from a top surface or deck surface 206 to a bottom surface 208. The top surface 206 is configured as a tissue-facing surface and the bottom surface 208 is configured as a channel-facing surface. As a result, when the staple cartridge 200 is inserted into the elongate staple channel 104, as shown in FIG. 1, the top surface 206 faces the anvil 102 and the bottom surface 208 (obstructed) faces the elongate staple channel 104. Further, the top surface 206 has two outer-most terminal longitudinal edges 207a, 207b that are positioned distal to the longitudinal slot 210 of the staple cartridge 200.

In some embodiments, the top surface 206 can include surface features defined therein. For example, the surface features can be recessed channels defined within the top surface 206. As shown in more detail in FIG. 2C, a first recessed channel 216 surrounds each first staple cavity 212a, 214a. Each first recessed channel 216 is defined by a substantially triangular wall 216a having a vertex pointing proximally, a vertex pointing distally, and a vertex pointing laterally outwardly. Further, each first recessed channel 216 includes a first floor 206a which is at a first height from the top surface 206. A second recessed channel 218 surrounds each second staple cavity 212b, 214b. Each second recessed channel 218 is defined by a wall 218a which is substantially diamond-shaped comprising a vertex pointing proximally, a vertex pointing distally, a vertex pointing laterally inwardly, and a vertex pointing laterally outwardly relative to the longitudinal axis. Further, each second recessed channel 218 includes a second floor 206b which is a second height from the top surface 206. A third recessed channel 220 surrounds each third staple cavity 212c, 214c. Each third recessed channel 220 is defined by a substantially triangular wall 220a comprising a vertex pointing proximally, a vertex pointing distally, and a vertex pointing laterally inwardly relative to the longitudinal axis. Further, each third recessed channel 220 includes a third floor 206c which is a third height from the top surface 206. In some embodiments, the first height of the first recessed channels 216, the second height of the second recessed channels 218, and the third height of the third recessed channels 220 can have the same height. In other instances, the first height, the second height, and/or the third height can be different. Additional details on the surface features and other exemplary surface features can be found in U.S. Publication No. 2016/0106427, which is incorporated by reference herein in its entirety.

With reference to FIGS. 4 and 5, a firing assembly such as, for example, firing assembly 400, can be utilized with a surgical stapling and severing device, like device 100 in FIG. 1. The firing assembly 400 can be configured to advance a wedge sled 500 having wedges 502 configured to deploy staples from the staple cartridge 200 into tissue captured between an anvil, like anvil 102 in FIG. 1, and a staple cartridge, like staple cartridge 200 in FIG. 1. Furthermore, an E-beam 402 at a distal portion of the firing assembly 400 may fire the staples from the staple cartridge. During firing, the E-beam 402 can also cause the anvil to pivot towards the staple cartridge, and thus move the staple applying assembly from the open position towards a closed position. The illustrated E-beam 402 includes a pair of top pins 404, a pair of middle pins 406, which may follow a portion 504 of the wedge sled 500, and a bottom pin or foot 408. The E-beam 402 can also include a sharp cutting edge 410 configured to sever the captured tissue as the firing assembly 400 is advanced distally, and thus towards the distal end of the staple cartridge. In addition, integrally formed and proximally projecting top guide 412 and middle guide 414 bracketing each vertical end of the sharp cutting edge 410 may further define a tissue staging area 416 assisting in guiding tissue to the sharp cutting edge 410 prior to being severed. The middle guide 414 may also serve to engage and fire the staples within the staple cartridge by abutting a stepped central member 506 of the wedge sled 500 that effects staple formation by the staple applying assembly 106.

In use, the anvil 102 in FIG. 1 can be moved into a closed position by depressing the closure trigger in FIG. 1 to advance the E-beam 402 in FIG. 4. The anvil can position tissue against at least the top surface 206 of the staple cartridge 200 in FIGS. 2A-2C. Once the anvil has been suitably positioned, the staples 300 in FIG. 3 disposed within the staple cartridge can be deployed.

To deploy staples from the staple cartridge, as discussed above, the wedge sled 500 in FIG. 5 can be moved from the proximal end toward a distal end of the cartridge body, and thus, of the staple cartridge. As the firing assembly 400 in FIG. 4 is advanced, the sled can contact and lift staple drivers within the staple cartridge upwardly within the staple cavities 212, 214. In at least one example, the sled and the staple drivers can each include one or more ramps, or inclined surfaces, which can co-operate to move the staple drivers upwardly from their unfired positions. As the staple drivers are lifted upwardly within their respective staple cavities, the staples are advanced upwardly such that the staples emerge from their staple cavities and penetrate into tissue. In various instances, the sled can move several staples upwardly at the same time as part of a firing sequence.

As indicated above, the stapling device can be used in combination with a compressible adjunct. A person skilled in the art will appreciate that, while adjuncts are shown and described below, the adjuncts disclosed herein can be used with other surgical devices, and need not be coupled to a staple cartridge as described. Further, a person skilled in the art will also appreciate that the staple cartridges need not be replaceable.

As discussed above, with some surgical staplers, a surgeon is often required to select the appropriate staples having the appropriate staple height for tissue to be stapled. For example, a surgeon will utilize tall staples for use with thick tissue and short staples for use with thin tissue. In some instances, however, the tissue being stapled does not have a consistent thickness and thus, the staples cannot achieve the desired fired configuration for every section of the stapled tissue (e.g., thick and thin tissue sections). The inconsistent thickness of tissue can lead to undesirable leakage and/or tearing of tissue at the staple site when staples with the same or substantially greater height are used, particularly when the staple site is exposed to intra-pressures at the staple site and/or along the staple line.

Accordingly, various embodiments of knitted adjuncts are provided that can be configured to compensate for varying thickness of tissue that is captured within fired (deployed) staples to avoid the need to take into account staple height when stapling tissue during surgery. That is, the adjuncts described herein can allow a set of staples with the same or similar heights to be used in stapling tissue of varying thickness (e.g., from thin to thick tissue) while also, in combination with the adjunct, providing adequate tissue compression within and between fired staples. Thus, the adjuncts described herein can maintain suitable compression against thin or thick tissue stapled thereto to thereby minimize leakage and/or tearing of tissue at the staple sites.

Alternatively or in addition, the knitted adjuncts can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

In general, the knitted adjuncts provided herein are designed and positioned atop a staple cartridge, like staple cartridge 200. When the staples are fired (deployed) from the cartridge, the staples penetrate through the adjunct and into tissue. As the legs of the staple are deformed against the anvil that is positioned opposite the staple cartridge, the deformed legs capture a portion of the adjunct and a portion of the tissue within each staple. That is, when the staples are fired into tissue, at least a portion of the adjunct becomes positioned between the tissue and the fired staple. While the adjuncts described herein can be configured to be attached to a staple cartridge, it is also contemplated herein that the adjuncts can be configured to mate with other device components, such as an anvil of a surgical stapler. A person of ordinary skill will appreciate that the adjuncts provided herein can be used with replaceable cartridges or staple reloads that are not cartridge based.

Figure 6:
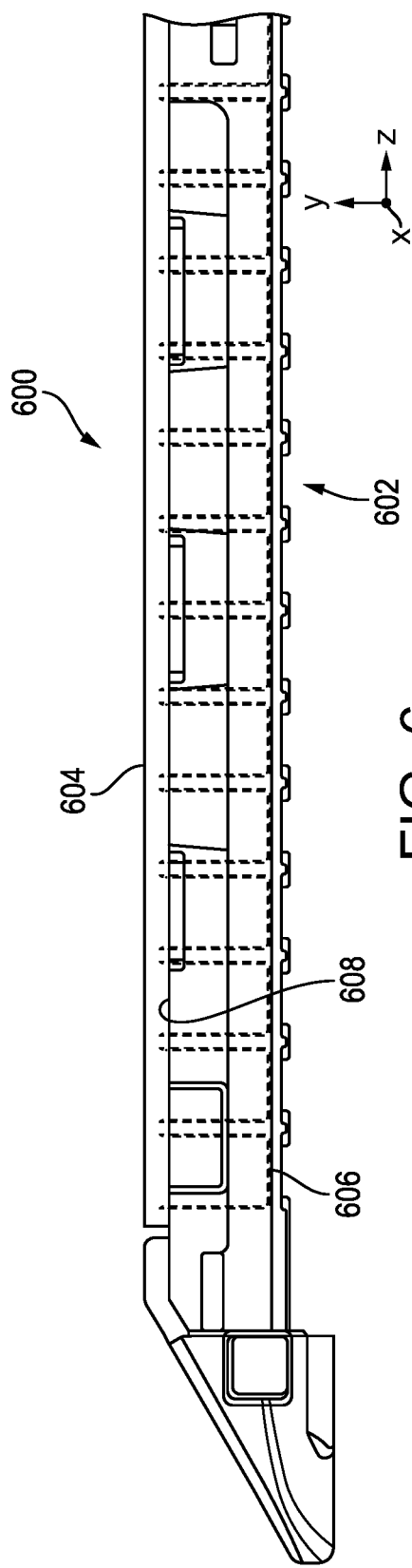
FIG. 6 is a longitudinal cross-sectional view of an exemplary embodiment of a surgical stapling assembly having a compressible knitted adjunct attached to a top or deck surface of a staple cartridge.

FIG. 6 illustrates an exemplary embodiment of a stapling assembly 600 that includes a staple cartridge 602 and an adjunct 604. For sake of simplicity, the adjunct 604 is generally illustrated in FIGS. 6A-6B, and various structural configurations of the adjunct are described in more detail below. Aside from the differences described in detail below, the staple cartridge 602 can be similar to staple cartridge 200 (FIGS. 1-3) and therefore common features are not described in detail herein. As shown, the adjunct 604 is positioned against the staple cartridge 602. While partially obstructed in FIG. 6, the staple cartridge 602 includes staples 606, which can be similar to staple 300 in FIG. 3, that are configured to be deployed into tissue. The staples 606 can have any suitable unformed (pre-deployed) height. For example, the staples 606 can have an unformed height between about 2 mm and 4.8 mm. Prior to deployment, the crowns of the staples can be supported by staple drivers (not shown).

Figure 2C:
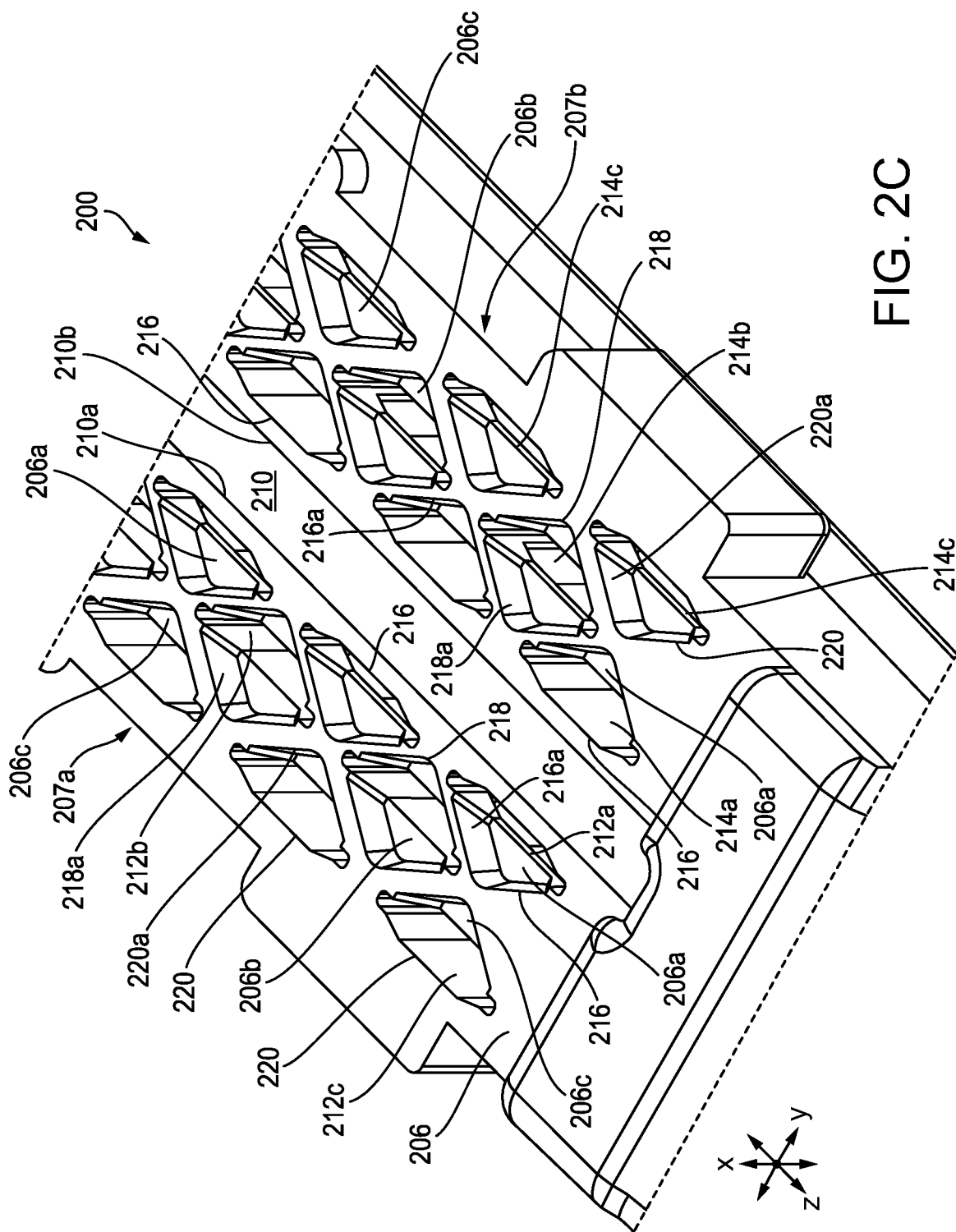
FIG. 2C is a perspective view of a portion of a tissue contacting surface of the staple cartridge of FIG. 2A.

In the illustrated embodiment, the adjunct 604 can be mated to at least a portion of the top surface or deck surface 608 of the staple cartridge 602. In some embodiments, the top surface 608 of the staple cartridge 602 can include one or more surface features, like recessed channels 216, 218, 220 as shown in FIGS. 2A and 2C. The one or more surface features can be configured to engage the adjunct 604 to avoid undesirable movements of the adjunct 604 relative to the staple cartridge 602 and/or to prevent premature release of the adjunct 604 from the staple cartridge 602. Exemplary surface features are described in U.S. Patent Publication No. 2016/0106427, which is incorporated by reference herein in its entirety.

The adjunct 604 is compressible to permit the adjunct to compress to varying heights to thereby compensate for different tissue thickness that are captured within a deployed staple. The adjunct 604 has an uncompressed (undeformed), or pre-deployed, height and is configured to deform to one of a plurality of compressed (deformed), or deployed, heights. For example, the adjunct 604 can have an uncompressed height which is greater than the fired height of the staples 606 disposed within the staple cartridge 602 (e.g., the height (H) of the fired staple 606a in FIG. 7). That is, the adjunct 604 can have an undeformed state in which a maximum height of the adjunct 604 is greater than a maximum height of a fired staple (e.g., a staple that is in a formed configuration). In one embodiment, the uncompressed height of the adjunct 604 can be about 10% taller, about 20% taller, about 30% taller, about 40% taller, about 50% taller, about 60% taller, about 70% taller, about 80% taller, about 90% taller, or about 100% taller than the fired height of the staples 606. In certain embodiments, the uncompressed height of the adjunct 604 can be over 100% taller than the fired height of the staples 606, for example.

In use, once the surgical stapling and severing device, like device 100 in FIG. 1, is directed to the surgical site, tissue is positioned between the anvil 612 and the stapling assembly 600 such that the anvil 612 is positioned adjacent to a first side of the tissue and the stapling assembly 600 is positioned adjacent to a second side of the tissue (e.g., the tissue can be positioned against the tissue-contacting surface 604a of the adjunct 604). Once tissue is positioned between the anvil 612 and the stapling assembly 600, the surgical stapler can be actuated, e.g., as discussed above, to thereby clamp the tissue between the anvil 612 and the stapling assembly 600 (e.g., between the tissue-compression surface 612a of the anvil 612 and the tissue-contacting surface 604a of the adjunct 604) and to deploy staples from the cartridge through the adjunct and into the tissue to staple and attach the adjunct to the tissue.

Figure 7:
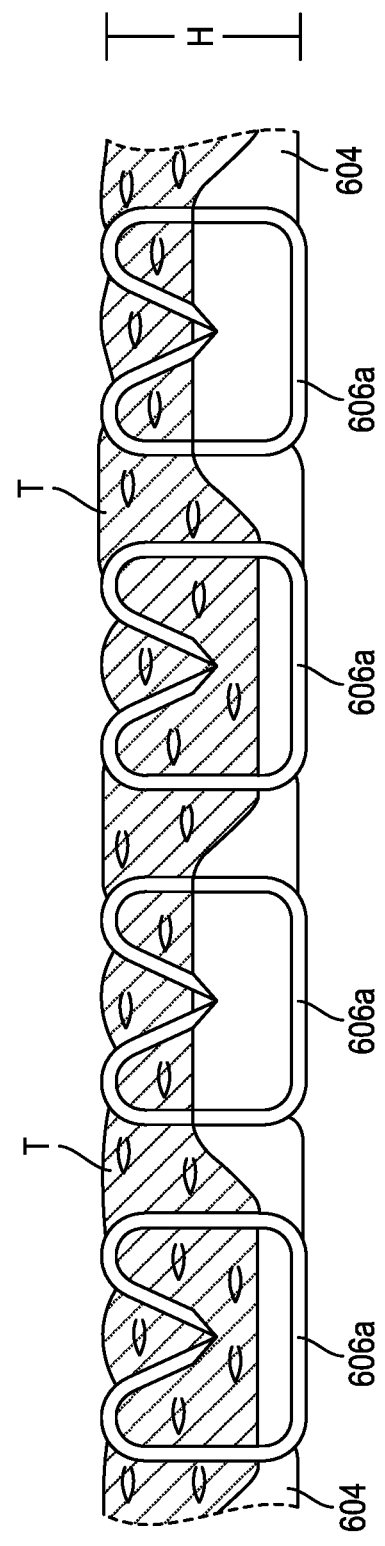
FIG. 7 is a partial-schematic illustrating the adjunct of FIGS. 6A-6B in a tissue deployed condition.

As shown in FIG. 7, when the staples 606 are fired, tissue (T) and a portion of the adjunct 604 are captured by the fired (formed) staples 606a. The fired staples 606a each define the entrapment area therein, as discussed above, for accommodating the captured adjunct 604 and tissue (T). The entrapment area defined by a fired staple 606a is limited, at least in part, by a height (H) of the fired staple 606a. For example, the height of a fired staple 606a can be about 0.160 inches or less. In some embodiments, the height of a fired staple 606a can be about 0.130 inches or less. In one embodiment, the height of a fired staple 606a can be from about 0.020 inches to 0.130 inches. In another embodiment, the height of a fired staple 606a can be from about 0.060 inches to 0.160 inches.

As described above, the adjunct 604 can be compressed within a plurality of fired staples whether the thickness of the tissue captured within the staples is the same or different within each fired staple. In at least one exemplary embodiment, the staples within a staple line, or row can be deformed such that the fired height is about 2.75 mm, for example, where the tissue (T) and the adjunct 604 can be compressed within this height. In certain instances, the tissue (T) can have a compressed height of about 1.0 mm and the adjunct 604 can have a compressed height of about 1.75 mm. In certain instances, the tissue (T) can have a compressed height of about 1.50 mm and the adjunct 604 can have a compressed height of about 1.25 mm. In certain instances, the tissue (T) can have a compressed height of about 1.75 mm and the adjunct 604 can have a compressed height of about 1.00 mm. In certain instances, the tissue (T) can have a compressed height of about 2.00 mm and the adjunct 604 can have a compressed height of about 0.75 mm. In certain instances, the tissue (T) can have a compressed height of about 2.25 mm and the adjunct 604 can have a compressed height of about 0.50 mm. Accordingly, the sum of the compressed heights of the captured tissue (T) and adjunct 604 can be equal, or at least substantially equal, to the height (H) of the fired staple 606a.

The knitted adjuncts can have a variety of configurations. In general, and as described in more detail below, the knitted adjuncts are formed of fibers that are knitted or woven (e.g., intertwined) together.

The knitted adjuncts can be formed of the same fibers, whereas in other embodiments, the knitted adjuncts can be formed of different fibers. The fibers can differ by material, dimensions (e.g., height and/or diameter), and/or structural configuration (e.g., monofilament or multifilament). In certain embodiments, the knitted adjuncts can include monofilament and/or multifilament fibers. As used herein, the term "monofilament fibers" has its own ordinary and customary meaning and can include fibers formed of a single filament. As used herein, the term "multifilament fibers" has its own ordinary and customary meaning and can include fibers formed of two or more filaments that are associated with one another (e.g., twisted or braided) to form a unitary structure.

The multifilament fibers can have a variety of configurations. For example, in some embodiments, each multifilament fiber includes from about 6 to 40 filaments. In one embodiment, each multifilament fiber includes from about 14 to 28 filaments. The increased surface area and voids that exist between the filaments of the multifilament fibers can facilitate improved tissue ingrowth within the adjunct.

The multifilament fibers can be formed of filaments formed of the same material or filaments of different materials. For example, in some embodiments, the multifilament fibers can include first filaments of a first material and second filaments of a second material. In one embodiment, the second material degrades at a faster rate than a degradation rate of the first material. In this way, the degradation of the second material can activate, and thus encourage accelerated attraction of, macrophages and accelerate the inflammation phase of healing while not substantially affecting the variable stiffness profile of the adjunct over time following implantation. The activation of macrophages can in turn cause increases in myofibroblast population and neovascularization. Further, the degradation of the second material can encourage tissue ingrowth within the adjunct. The first material, for example, can be at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. Non-limiting examples of suitable first materials can be formed of polyglactin 910, Lactomer™ 9-1, 75:25 or 50:50 lactic acid/glycolic acid, Polygytone™ 6211, or Caprosyn™. The second material, for example, can be a copolymer of glycolide and L-lactide, such as Vicryl Rapide™.

While the multifilament fibers can include the second filaments at various percentage ranges, in some embodiments, the multifilament fibers can each include second filaments at a range of about 15% to 85% or at a range of about 25% to 45%. The second filaments can have various fiber diameters. For example, in some embodiments, the second filaments can have a fiber diameter from about 0.0005 mm to 0.02 mm. In one embodiment, the second filaments have a fiber diameter of about 0.015 mm.

The monofilament fibers can have a variety of sizes. For example, the monofilaments can have a diameter of about 0.2 mm to 0.35 mm. In some embodiments, the monofilament fibers can each have a diameter that is less than an average fiber diameter of the multifilament fibers. The average fiber diameter (D) of a multifilament fiber can be calculated using the following formula:

$$D = \sqrt{\frac{4W}{N\rho\pi}}$$

wherein:
W=weight of multifilament fiber (fiber bundle) per unit length
N=number of filaments
ρ=density of fiber.

The multifilament fibers can have a variety of sizes. For example, each multifilament fiber can have an average fiber diameter of about 0.02 mm to 0.2 mm, of about 0.05 mm to 0.2 mm, or of about 0.15 mm to 0.2 mm. In some embodiments, each filament of the multifilament fibers has a diameter that is less than a fiber diameter of the monofilament fibers. For example, where the adjunct includes first fibers that are multifilament fibers and second fibers that are monofilament fibers, each filament of the multifilament fibers can have a diameter that is about ⅕ to ½₀ the diameter of the monofilament fibers. In certain embodiments, each filament of the multifilament fibers can have a diameter that is about ½₀ the diameter of the monofilament fibers.

As discussed above, a portion of the adjunct is captured with tissue within the fired staple and therefore it is desirable that the adjunct be formed of suitable bioabsorbable materials. As such, the fibers can each be formed of bioabsorbable material(s). Non-limiting examples of suitable bioabsorbable materials include poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide, polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate.

In some embodiments, a knitted adjunct can include at least two different types of fibers. Non-limiting examples of suitable materials for the first type of fibers include at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. For example, the first type of fibers can be formed of polyglactin 910, Lactomer™ 9-1, 75:25 or 50:50 lactic acid/glycolic acid, Polygytone™ 6211, or Caprosyn™. Non-limiting examples of suitable materials for the second type of fibers include at least one of polydioxanone, a copolymer of polydioxanone and polyglycolide, a copolymer of lactide and polycaprolactone), a copolymer of glycolide, dioxanone, and trimethylene carbonate, poly (trimethylene carbonate), polyhydroxyalkanoate, and polyglyconate. For example, the second type of fibers can be formed of 92:8 polydioxanone/Polyglycolide, 25:75 lactide/polycaprolactone, Glycomer™ 631, or Maxon™. In one embodiment, the first type of fibers is formed of polyglactin 910 and the second type of fibers is formed of polydioxanone.

The knitted adjuncts can have various sizes, shapes, and configurations. In general, an adjunct includes at least core or intermediate layer and at least one outer layer. For example, the adjunct can include a first outer layer (e.g. a top or tissue-contacting layer) formed of at least first fibers that are knitted or woven together (e.g., a knitted layer) and a second outer layer (e.g., a bottom or cartridge-contacting layer) formed of at least second fibers that are knitted or woven together (e.g., a knitted layer). The first and second fibers can be the same or different. The adjunct can also include spacer fibers that can be the same or different than the first and second fibers. The spacer fibers intertwine with and extend between the first and second outer layers to thereby connect these layers together such that the portions of the spacer fibers extending between the two outer layers form at least one of the at least one core or intermediate layer of the adjunct.

Each layer of the adjunct extends from a first surface (e.g., a top surface) to a second surface (e.g., a bottom surface). Depending on the overall structural configuration of the adjunct, at least a portion of the first surface of one layer can serve as a tissue-contacting surface, and at least a portion of the second surface of another layer can serve as a cartridge-contacting surface. A person skilled in the art will appreciate that the adjunct can have additional tissue-contacting surfaces (e.g., one or more lateral side surfaces relative to the top surface).

In some embodiments, the spacer fibers interconnect with the first and second fibers of the outer layers in a manner in which the spacers fibers are non-fixedly attached and slidably interconnected. As such, the fibers can move relative to each other, thereby allowing for movement and for expansion of the knitted adjunct in the x-direction (e.g., stretch) and the y-direction (e.g., compression). Additionally, the interconnection between the spacer fibers and the first and second fibers of the outer layers can affect, at least in part, the stiffness of the adjunct. For example, the tighter the interconnections, the stiffer the adjunct.

The first and second outer layers can each include a plurality of openings formed therein. The perimeter of the openings of the first outer layer can be defined by portions of the first fibers and of the spacer fibers, whereas the perimeter of the openings of the second outer layer can be defined by portions of the second fibers and of the spacer fibers. In certain embodiments, the openings of the second outer layer can have a size that is less than about ¼ of a width of a crown of a staple, like staple 300 in FIG. 3. In such embodiments, the crown of the fired staple can therefore span over at least four openings in the second outer layer. In one embodiment, the openings can have a size that is about ⅛ of the width of the crown. While the crown of a staple can have a variety of widths, in some embodiments, the width of the crown can be about 0.080 inches to 0.140 inches. In one embodiment, the width of the crown is about 0.12 inches.

In certain embodiments, the portions of the spacer fibers that extend between the first and second outer layers can be arranged to form standing fibers and a plurality of voids therebetween. The standing fibers are non-fixedly attached to each other. Further, the standing fibers are non-fixedly and slidably interconnected to the first type of fibers of the first and second outer layers. In some implementations, the plurality of voids can be larger than the plurality of openings in the first and second outer layers.

The standing fibers can be configured to bend under force being applied to the adjunct (e.g., when stapled to tissue). The resilience of the standing fibers permits the adjunct, at least in part, to compress at various heights to thereby accommodate tissue (T) with tissue portions of different thicknesses. That is, independent of the particular tissue thickness, the sum of the compressed heights of the captured tissue and adjunct within the fired staple can be maintained, and thus can remain equal, or at least substantially equal, to the height of the fired staple. In this way, at least in part, the knitted adjunct can be configured to apply a stress of at least about 3 gf/mm$^2$ to the captured tissue for at least a predetermined period (e.g., at least about 3 days).

Generally, the material composition, the height, and/or the transverse cross-sectional area of each standing fiber controls, at least in part, its stiffness or ability to bend under compression which, in turn, controls, at least in part, the overall compressibility of the adjunct. Accordingly, the standing fibers can be configured to tune the compressibility of the adjunct to one or more desired values. For example, in some embodiments, the standing fibers can be formed of the same material, whereas in other embodiments, at least a portion of the standing fibers can be formed of different materials with different stiffnesses. Alternatively or in addition, the standing fibers, or at least a portion thereof, can have different heights and/or transverse cross-sectional areas.

The amount of the standing fibers within a certain region or section of the adjunct can also affect, among other things, the compressibility of such section, and thus the overall compressibility of the adjunct. In certain instances, the standing fibers can be strategically concentrated in certain regions of adjunct to provide greater compression strength in such regions, for example. In at least one instance, the standing fibers can be concentrated in regions of the core or intermediate layer that are configured to receive staples when the staples are fired. Alternatively, the standing fibers can be concentrated in regions of the adjunct that do not receive staples when the staples are fired (e.g., regions that overlap with the intended cut-line of the adjunct).

The ratio of the voids to the standing fibers can vary. In some embodiments, this ratio can be in the range of at least about 3:1. In other embodiments, the ratio of voids to the standing fibers can in the range of at least about 5:1 or of at least about 12:1. Further, at least a portion of the voids can each have a different size. In this way, the variable void sizes throughout the cross-section of the adjunct 804 can promote extracellular remodeling. That is, the variable void sizes can facilitate revascularization as well as mobility of cells within the adjunct when the adjunct is implanted, thereby encouraging both tissue and cellular ingrowth. Further the variable void sizes can also facilitate extraction of byproducts and cellular waste from the implanted adjunct, and thus the implantation site.

Edges Conditions

As discussed above, the knitted adjuncts are formed of fibers that are knitted or woven together. In certain embodiments, the knitted adjuncts can be designed such that the free ends of at least a portion of the fibers are connected together so as to form one or more finished edges of the adjunct. The one or more finished edges are configured to substantially, or completely, prevent fraying or fiber separation therealong. As a result, the structural integrity of the adjunct can be maintained when exposed to forces that would otherwise cause the fibers to fray or separate from each other. The one or more finished edges can also provide an aesthetic effect and/or decrease the variability in both the structure and attendant properties of the present adjuncts, as compared to conventional adjuncts (e.g., adjuncts that do not have finished edges).

The one or more finished edges can be formed in a variety of ways. For example, in some embodiments, additional fiber(s) (e.g., fibers different than those used to form the main body of the adjunct) can be used to interconnect the terminal edges of opposing layers of the adjunct together (see FIGS. 8A-10D). In such embodiments, the additional fiber(s) can be knitted or woven into the terminal edges in a variety of configurations (e.g., as an overcast stitch, an overedge stitch, a zizzag stitch, and the like).

Figure 8B:
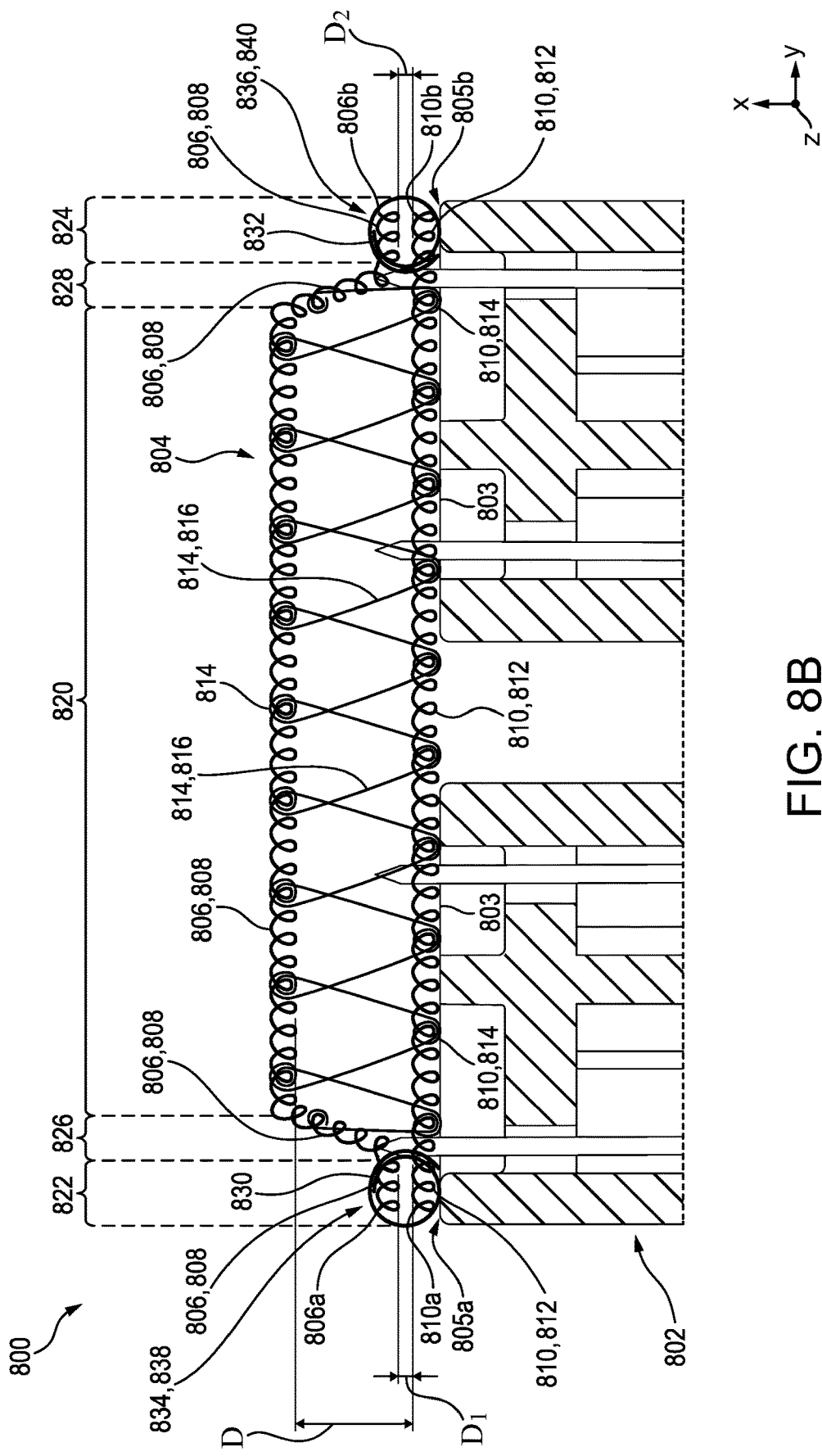
FIG. 8B is a cross-sectional view of the portion of the stapling assembly of FIG. 8A taken at line 8B-8B.

FIGS. 8A-8B illustrate one exemplary embodiment of a stapling assembly 800 that includes a staple cartridge 802 and a knitted adjunct 804 disposed on a top or deck surface 803 of the staple cartridge 802. The staple cartridge 802 is similar to staple cartridge 200 in FIGS. 1-2C, and therefore common features are not described in detail herein.

In this illustrated embodiment, as shown in more detail in FIG. 8B, the adjunct 804 includes a top layer 806 (e.g., a tissue-contacting layer) formed of at least first fibers 808, a bottom layer 810 (e.g., a cartridge-contacting layer) formed of at least second fibers 812, and spacer fibers 814 that are intertwined with and extending between the top and bottom layers 806, 810 to thereby connect the top and bottom layers 806, 810 together. In this illustrated embodiment, the spacer fibers 814 are multi-looped about the first fibers 808 and about second fibers 812. The portions of the spacer fibers 814 that extend between the top and bottom layers 806, 810 form an intermediate or core layer 816 of the adjunct 804. For sake of simplicity, only one first fiber 808, second fiber 812, and spacer fiber 814 is illustrated in FIG. 8B. A person skilled in the art will appreciate that the following discussion is also applicable to the remaining first, second, and spacer fibers of the adjunct.

The top and bottom layers 806, 810 can have a variety of structural configurations. As shown, the top layer 806 has two outer-most longitudinal terminal edges 806a, 806b, and the bottom layer has two outer-most longitudinal terminal edges 810a, 810b. In some embodiments, the first fibers 808 of the top layer 806 can be knitted or woven into a first predetermined pattern and/or the second fibers 812 of the bottom layer 810 can be knitted or woven into a second predetermined pattern. In certain embodiments, the first and second predetermined patterns can be generally identical (e.g., nominally identical within manufacturing tolerances), whereas in other embodiments, the first and second predetermined patterns can be different. While the first fibers 808 and the second fibers 812 can be knitted or woven in various patterns, in certain embodiments, the first fibers 808 can be knitted into a first Raschel knit pattern and the second fibers 812 can be knitted into a second Raschel knit pattern that is the same or different than the first Raschel knit pattern. Further, in some embodiments, the fiber density of the top layer 806 can be different than the fiber density of the bottom layer 810. A person skilled in the art will appreciate that the first fibers 808 and the second fibers 812 can be randomly or repeatedly knitted or woven within the top and bottom layers 806, 810, respectively. As such, and for sake of simplicity, the top and bottom layers 806, 810 are generally illustrated, and thus the specific structural configurations of the top and bottom layers 806, 810 are not limited to what is depicted in the figures.

The first fibers 808, the second fibers 812, and the spacer fibers 814 can have a variety of configurations. For example, in some embodiments, the first fibers 808, the second fibers 812, and the spacer fibers 814 can be generally identical (e.g., nominally identical within manufacturing tolerances) in material and/or structural configuration. In other embodiments, the first and second fibers 808, 812 can be generally identical (e.g., nominally identical within manufacturing tolerances) in material and/or structural configuration relative to each other and the spacer fibers 814 can be different relative thereto. For example, in certain embodiments, the first and second fibers 808, 812 can be multifilament fibers, and the spacer fibers 814 can be monofilament fibers. As such, aside from the general overall shape, the specific structural configuration of each of the first fibers 808, the second fibers 812, and the spacer fibers 814 is not shown.

While the adjunct 804 can have a variety of configurations, in the embodiment shown in FIG. 8B, the adjunct 804 includes an inner-most segment 820 that includes the first fibers 808, the second fibers 812, and the spacer fibers 814, and first and second outer-most segments 822, 824 that are positioned on opposite sides (e.g., longitudinal sides) of the inner-most segment 820 and along the longitudinal axis $L_A$ of the adjunct (e.g., in the z-direction). As a result, when the adjunct 804 is releasably coupled to the top or deck surface 803 of the staple cartridge 802, the first outer-most segment 822 is adjacent to and extends along the first outer-most longitudinal edge 805a of the top surface 803 and the second outer-most segment 824 is adjacent to and extends along the second outer-most longitudinal edge 805b of the top surface 803 of the cartridge 802.

While the first and second outer-most segments 822, 824 can have different structural configurations, in this illustrated embodiment, the first and second outer-most segments 822, 824 are generally identical (e.g., nominally identical within manufacturing tolerances). The first and second outer-most segments 822, 824 each include only the first fibers 808 and the second fibers 812, and thus only portions of the top and bottom layers 806, 810. That is, in this illustrated embodiment, the spacer fibers 814 are not present within the first and second outer-most segments 822, 824, and as a result, the mechanical behavior of the adjunct 804 can be predominately controlled by the inner-most segment 820, and consequently, by the mechanical behavior of the spacer fibers 814. In other embodiments, the first outer-most segment 822 and/or the second outer-most segment 824 can include the spacer fibers 814. Further, as shown, the first outer-most segment 822 includes the first outer-most longitudinal terminal edges 806a, 810a of the top and bottom layers 806, 810, each of which includes a portion of the free ends of the first fibers 808 and of the second fibers 812. Similarly, the second outer-most segment 824 includes the second outer-most longitudinal terminal edges 806b, 810b of the top and bottom layers 806, 810, each of which includes a portion of the free ends of the first fibers 808 and of the second fibers 812.

As shown in more detail in FIG. 8B, the portions of the top and bottom layers 806, 810 within the inner-most segment 820 extend parallel to one another along the longitudinal axis $L_A$ (e.g., extending in the z-direction) of the adjunct 804 and are spaced apart at a distance D. Similarly, the respective portions of the top layer 806 and bottom layer 810 within the first and second outer-most segments 822, 824 extend parallel to one another along the longitudinal axis $L_A$ of the adjunct 804 (e.g., extending in the z-direction) and are spaced apart at a respective distance $D_1$, $D_2$. As such, the portions of the top and bottom layers 806, 810 within the first outer-most segment 822 at least partially overlap with each other and the portions of the top and bottom layers 806, 810 within the second outer-most segment 824 at least partially overlap with each other. While in certain embodiments the distances D, $D_1$, $D_2$ can be all the same or all different, in this illustrated embodiment, distance D is different than distance $D_1$ and distance $D_2$, with distance $D_1$ and distance $D_2$ being generally identical (nominally identical within manufacturing tolerances).

The difference between distance D and distances $D_1$, $D_2$ is due to the tapering transition between the inner-most segment 820 and the first and second outer-most segments 822, 824 of the adjunct 804 via first and second intermediate segments 826, 828. The first intermediate segment 826 extends from the inner-most segment 820 to the first outer-most segment 822 and the second intermediate segment 828 extends from the inner-most segment 820 to the second outer-most segment 824. The first and second intermediate segments 826, 828 are tapered in which respective portions of the top layer 806 extend at an angle relative to respective portions of the bottom layer 810. As shown, the respective portions of the top layer 806 extend towards respective portions of the bottom layer 810 within the first and second intermediate segments 826, 828. As a result, the distance D between the portion of the top and bottom layers 806, 810 of the inner-most segment 820 is greater than the distances $D_1$, $D_2$ between the portion of the top and bottom layers 806, 810 of the first outer-most segment and of the second outer-most segment, respectively. This relationship between distance D and distances $D_1$, $D_2$ can allow additional fiber(s), like first and second additional fibers 830, 832, to be used to interconnect the one or more terminal edges of the top and bottom layers 806, 810 without adversely affecting the overall mechanical behavior of the adjunct 804.

As further shown, the adjunct 804 includes first additional fiber 830 (FIG. 8B) and second additional fiber 832 (FIGS. 8A-8B). The first and second additional fibers 830, 832 form respective first and second finished edges 834, 836, in which each finished edge is configured to prevent fraying of the top and bottom layers 806, 810 therealong, and thus fraying and/or fiber separation of the first fibers 808 and the second fibers 812.

The first and second additional fibers 830, 832 can have a variety of configurations. In some embodiments, the first additional fiber 830 and the second additional fiber 832 can be generally identical (nominally identical within manufacturing tolerances) in compositional makeup (e.g., formed of the same material(s)), dimension(s) (e.g., height and/or diameter) and/or in structural configuration (e.g., monofilament or multifilament). In certain embodiments, the first additional fiber 830 and/or the second additional fiber 832 can be a monofilament fiber. In other embodiments, the first additional fiber 830 and/or the second additional fiber 832 can be a multifilament fiber. As such, aside from the general overall shape, the specific structural configuration of the first and second additional fibers 830, 832 is not shown. Further, while only one first additional fiber and one second additional fiber are illustrated in FIGS. 8A-8B, a person skilled in the art will appreciate that more than one first additional fiber and/or more than one second additional fiber and/or other additional fiber(s) can be used to form the finished edges of the adjunct.

The first and second additional fibers 830, 832 can be incorporated into the adjunct 804 in a variety of ways to form the first and second finished edges 834, 836. In this illustrated embodiment, the first additional fiber 830 interconnects the top and bottom layers 806, 810 along their first outer-most longitudinal terminal edges 806a, 810a to form the first finished edge 834. As a result, the first finished edge 834 is formed of the first fibers 808, the second fibers 812, and the first additional fiber 830 and is positioned along, and thus defines, at least a portion of a first outer-most longitudinal edge 838 of the adjunct 804. The second additional fiber 832 interconnects the top and bottom layers 806, 810 along their respective second outer-most longitudinal terminal edges 806b, 810b to form the second finished edge 836. As a result, the second finished edge 836 is formed of the first fibers 808, the second fibers 812, and the second additional fiber 832 and is positioned along, and thus defines, at least a portion of a second outer-most longitudinal edge 840 of the adjunct 804. Thus, at least a portion of the outer-most perimeter of the adjunct is defined by the first and second finished edges 834, 836.

Further, the first additional fiber 830 and/or the second additional fiber 832 can be configured as an overcast stitch. For example, as shown in greater detail in FIG. 8B, the first additional fiber 830 and the second additional fiber 832 are wrapped around the first outer-most longitudinal terminal edges 806a, 810a and the second outer-most longitudinal terminal edges 806b, 810b, respectively, in the form of loops (e.g., in a spiral-type or zig-zag configuration). As a result, the portion of free ends of the first and second fibers 808, 812 at the first outer-most longitudinal terminal edges 806a, 810a are secured together by the first additional fiber 830 and the portion of free ends of the first and second fibers 808, 812 at the second outer-most longitudinal terminal edges 806b, 810b are secured together by the second additional fiber 832. In other embodiments, the first and second additional fibers 830, 832 can be configured as other suitable stitch forms. Further, in certain embodiments, the first and second additional fibers 830, 832 can configured as different stitch forms.

Figure 9A:
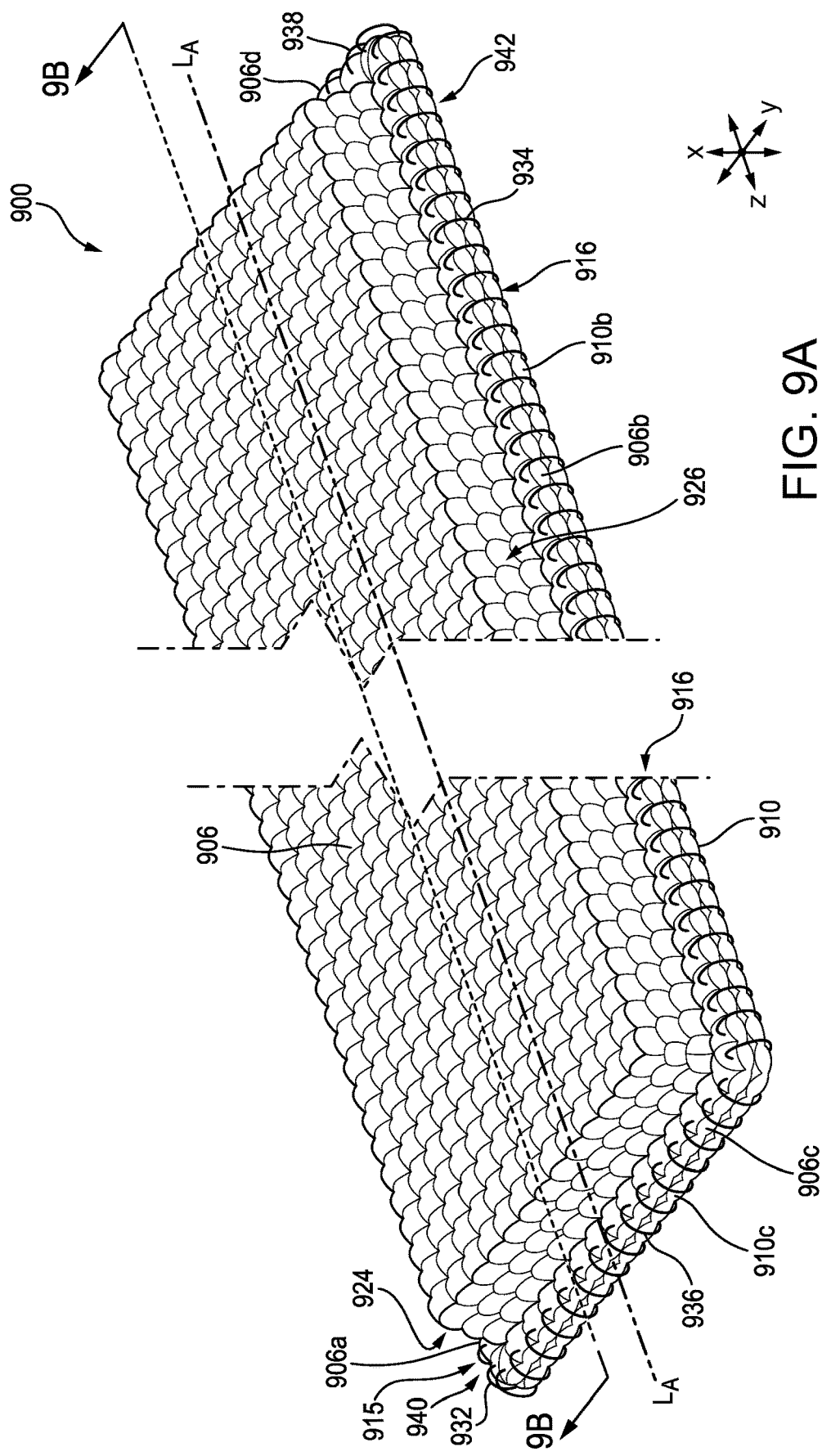
FIG. 9A is a perspective view of another exemplary embodiment of compressible knitted adjunct.
Figure 9B:
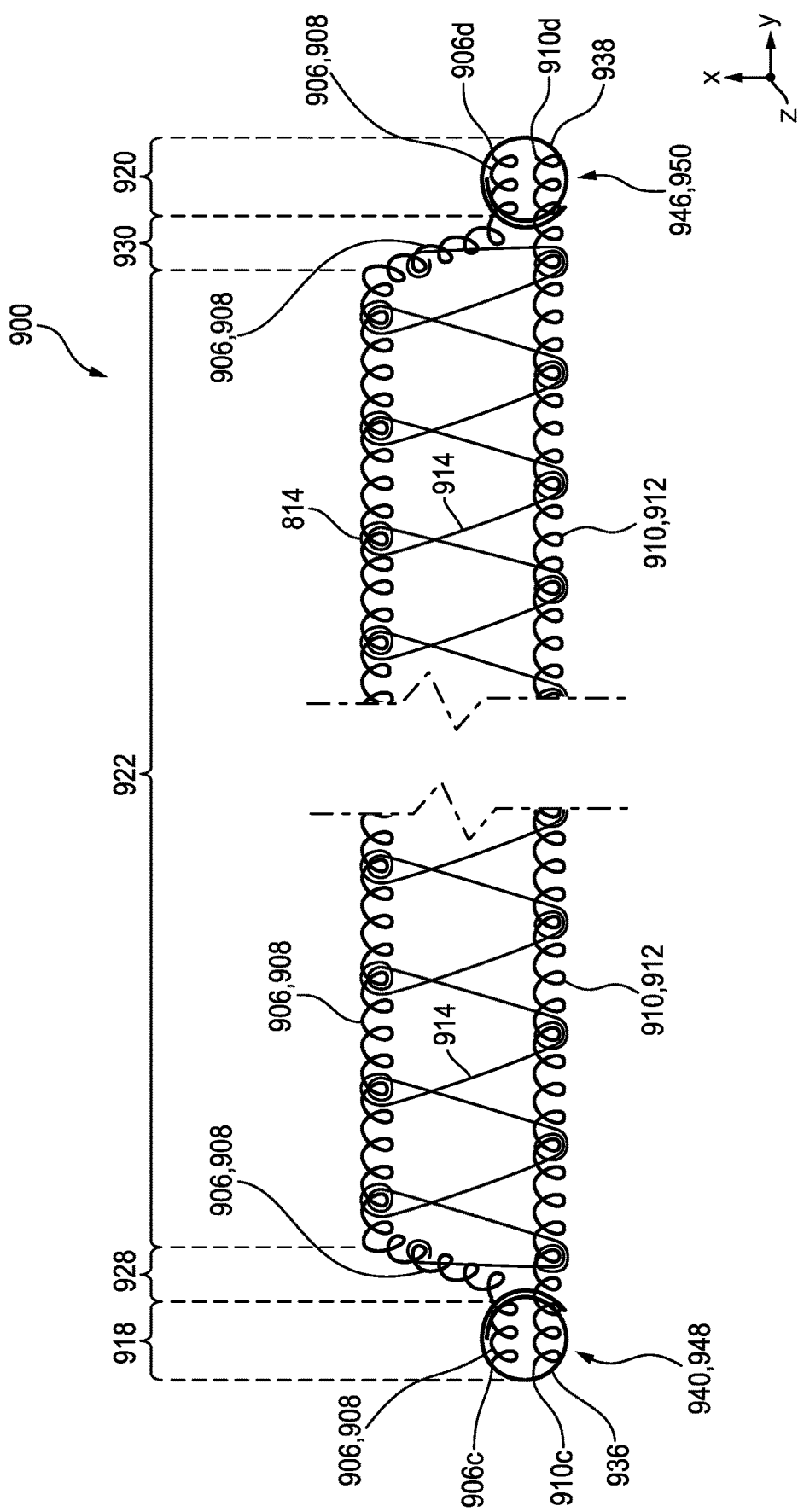
FIG. 9B is a cross-sectional view of the adjunct of FIG. 9A taken at line 9B-9B.
Figure 10A:
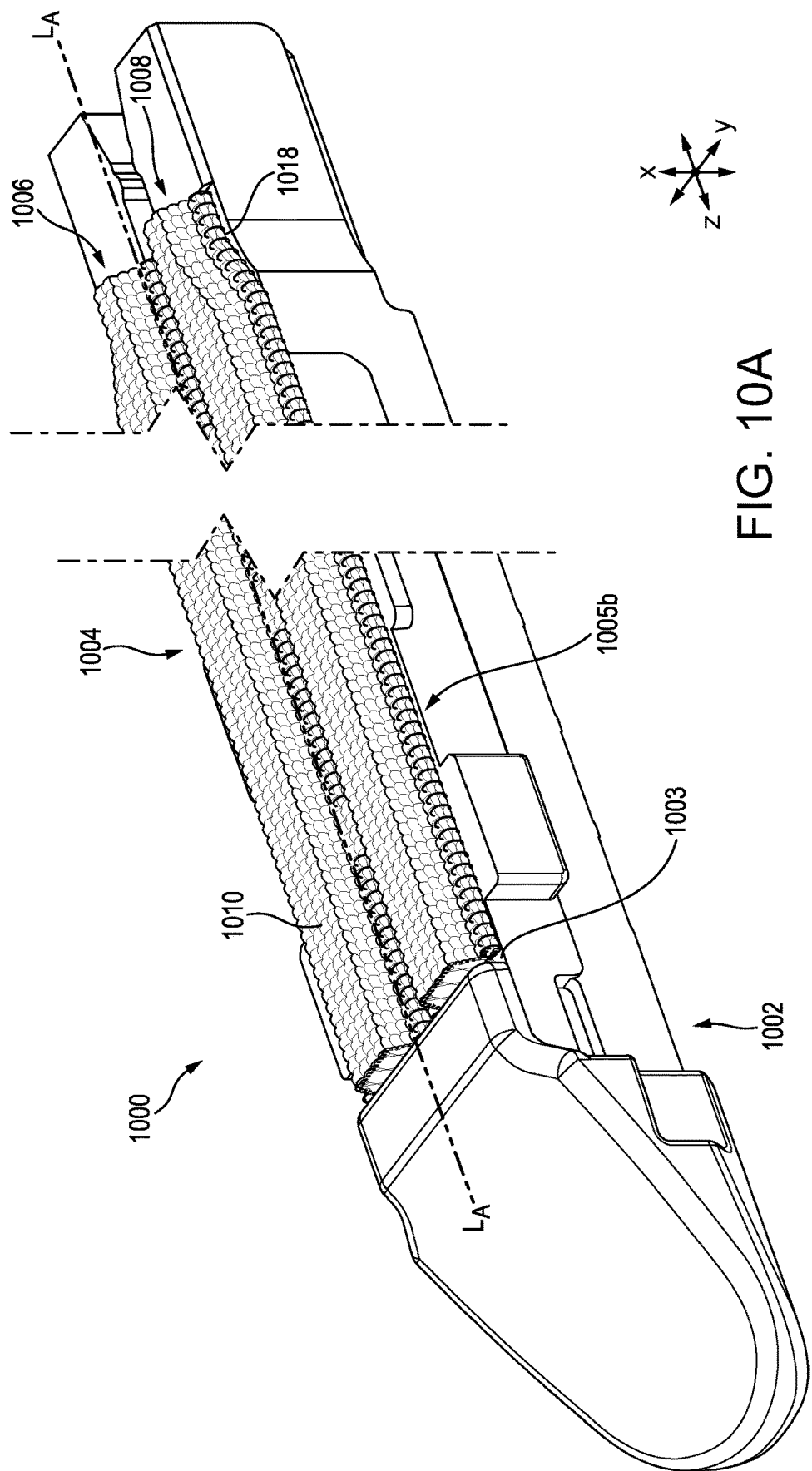
FIG. 10A is a perspective view of another exemplary embodiment of a stapling assembly having a compressible knitted adjunct releasably retained on a staple cartridge.
Figure 10B:
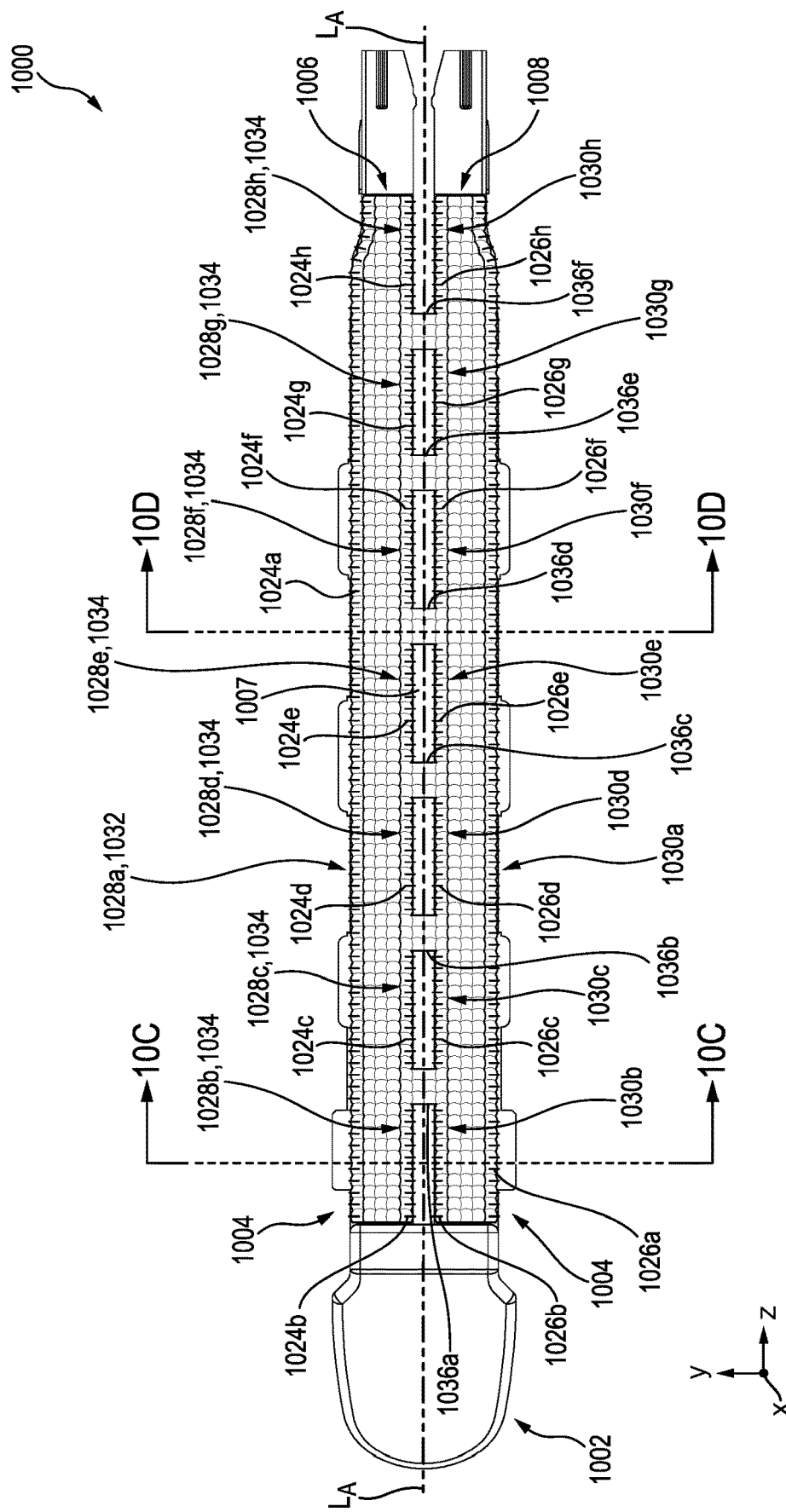
FIG. 10B is a top view of the stapling assembly of FIG. 10A.
Figure 10C:
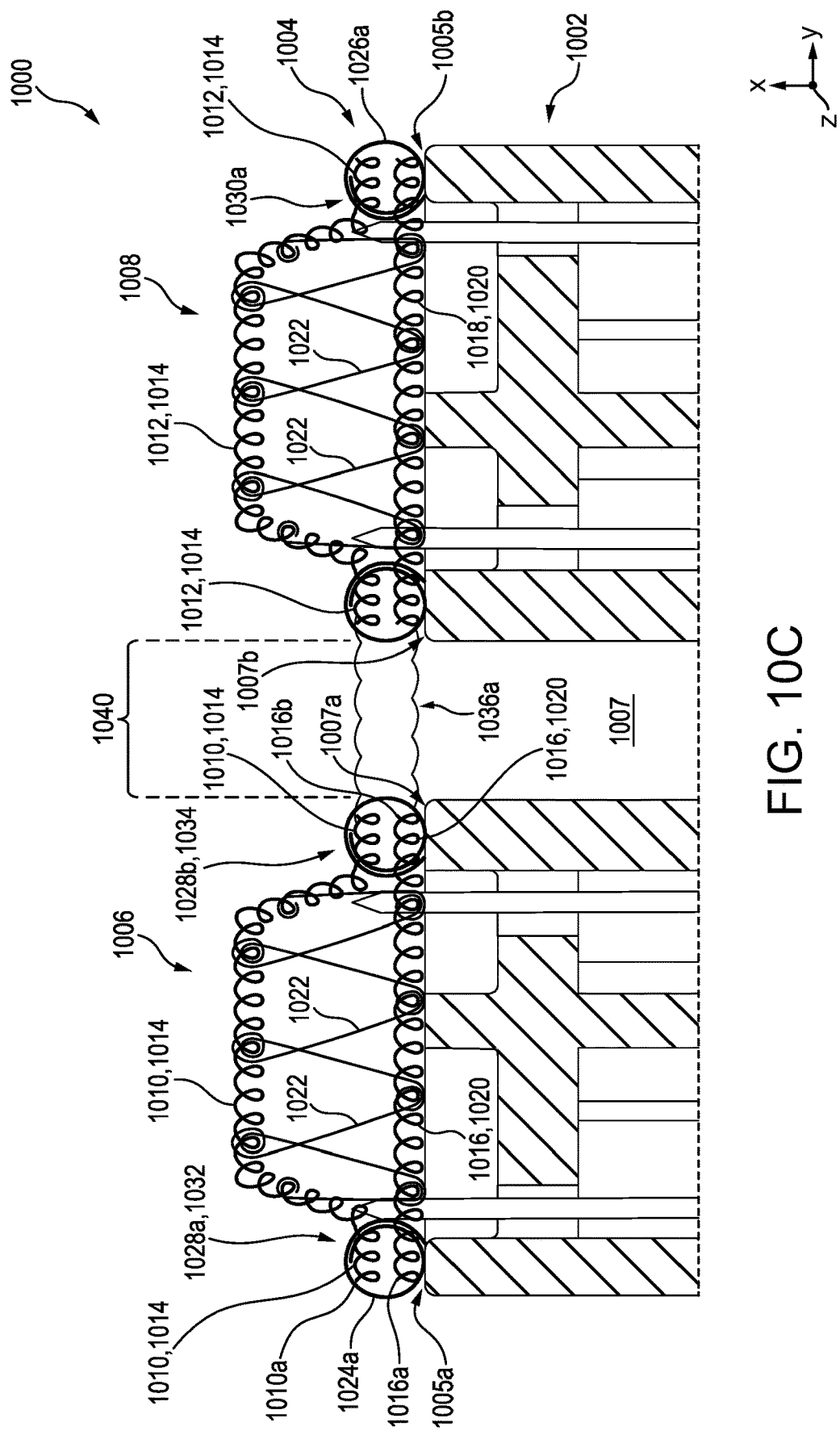
FIG. 10C is a cross-sectional view of the stapling assembly of FIG. 10B taken at line 10C-10C.
Figure 10D:
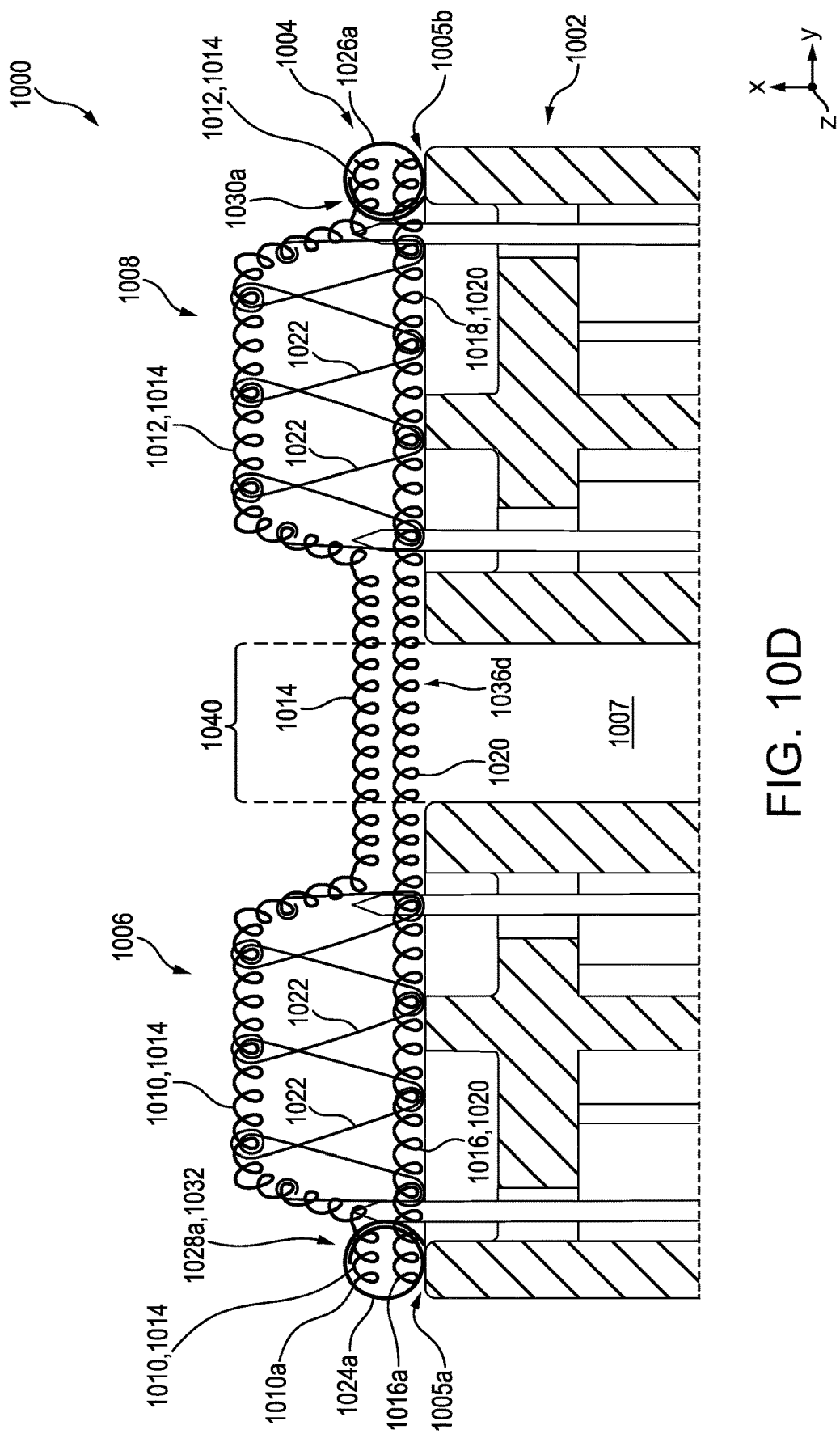
FIG. 10D is a cross-sectional view of the stapling assembly of FIG. 10B taken at line 10D-10D.

FIGS. 9A-9B illustrate another exemplary embodiment of a knitted adjunct 900 having one or more finished edges formed by respective additional fibers. Aside from the differences discussed below, the adjunct 900 is similar to adjunct 804 in FIGS. 8A-8B, and therefore common features are not described in detail herein.

The adjunct 900 includes a top layer 906 (e.g., a tissue-contacting layer) formed of first fibers 908, a bottom layer 910 (e.g., a cartridge-contacting layer) formed of second fibers 912, and spacer fibers 914 that are intertwined with and that extend between the top and bottom layers 906, 910 to thereby connect the top and bottom layers 906, 910 together. As shown in FIG. 9A, the top layer 906 has at least two outer-most longitudinal terminal edges 906a, 906b and at least two outer-most lateral terminal edges 906c, 906d. The bottom layer 910 has at least two outer-most longitudinal terminal edges (only one outer-most longitudinal terminal edge 910b being illustrated in FIG. 9A) and at least two outer-most lateral terminal edges 910c, 910d.

In addition to the first and second outer-most segments 915, 916 (see FIG. 9A), which are similar to the first and second outer-most segments 822, 824 in FIGS. 8A-8B, the adjunct 900 includes third and fourth outer-most segments 918, 920 (see FIG. 9B). The third and fourth outer-most segment 918, 920 are positioned on opposite sides (e.g., lateral sides) of the inner-most segment 922 and extend orthogonal (e.g., in the y-direction) to the longitudinal axis $L_A$ of the adjunct (e.g., extending the z-direction). Aside from their position within the adjunct 900, the third and fourth outer-most segments 918, 920 are structurally similar to the first and second outer-most segments 915, 916.

Further, in addition to the first and second intermediate segments 924, 926 (see FIG. 9A), which are similar to the first and second intermediate segments 826, 828 in FIGS. 8A-8B, the adjunct 900 includes third and fourth intermediate segments 928, 930 (see FIG. 9B). As shown, the third intermediate segment 928 extends from the inner-most segment 922 to the third outer-most segment 918 and the fourth intermediate segment 930 extends from the inner-most segment 922 to the fourth outer-most segment 920. Aside from their position within the adjunct 900, the third and fourth intermediate segments 928, 930 are structurally similar to first and second intermediate segments 924, 926.

As further shown in FIGS. 9A-9B, the adjunct 900 includes first, second, third, and fourth additional fibers 932, 934, 936, 938 that form respective first, second, third, and fourth finished edges 940, 942, 944, 946 that are configured to prevent fraying of the top and bottom layers 906, 910 therealong, and thus fraying and/or fiber separation of the first fibers 908 and the second fibers 912. Each additional fiber 932, 934, 936, 938 can be incorporated into the adjunct in a variety of ways to form respective finished edges 940, 942, 944, 946. The first and second finished edges 940, 942 are similar to first and second finished edges 834, 836 in FIGS. 8A-8B and therefore not described in detailed herein.

The third and fourth additional fibers 936, 938 can be incorporated into the adjunct 900 in a variety of ways to form the third and fourth finished edges 944, 946. In this illustrated embodiment, the third additional fiber 936 interconnects the top and bottom layers 906, 910 along their first outer-most lateral terminal edges 906c, 910c to form the third finished edge 944. As a result, the third finished edge 944 is formed of the first fibers 908, the second fibers 912, and the third additional fiber 936 and is positioned along, and thus defines, at least a portion of a first outer-most lateral edge 948 of the adjunct 900. The fourth additional fiber 938 interconnects the top and bottom layers 906, 910 along their respective second outer-most lateral terminal edges 906d, 910d to form the fourth finished edge 946. As a result, the fourth finished edge 946 is formed of the first fibers 908, the second fibers 912, and the fourth additional fiber 938 and is positioned along, and thus defines, at least a portion of a second outer-most lateral edge 950 of the adjunct 900. Thus, at least a portion of the outer-most perimeter of the adjunct 900 is defined by the first, second, third, and fourth finished edges 940, 942, 944, 946. In certain embodiments, for example, as shown in FIG. 9A, the outer-most perimeter of the adjunct 900 can be entirely defined by finished edges.

Further, the third additional fiber 936 and/or the fourth additional fiber 938 can be configured as an overcast stitch. For example, as shown, the third additional fiber 936 and the fourth additional fiber 938 are wrapped around the first outer-most lateral terminal edges 906c, 910c and the second outer-most lateral terminal edges 906d, 910d, respectively, in the form of loops (e.g., in a spiral-type configuration). As a result, the portion of free ends of the first and second fibers 908, 912 at the first outer-most lateral terminal edges 906c, 910c are secured together by the third additional fiber 936 and the portion of free ends of the first and second fibers 908, 912 at the second outer-most lateral terminal edges 906d, 910d are secured together by the fourth additional fiber 938. In other embodiments, the third and fourth additional fibers 936, 938 can be configured as other suitable stitch forms.

Further, in certain embodiments, the third and fourth additional fibers 936, 938 can be configured as different stitch forms.

Alternatively, or in addition, the adjunct can include inner-most longitudinal terminal edge(s) relative to its outer-most longitudinal terminal edges (e.g., first and second outer-most longitudinal terminal edges 806*a*, 806*b*, 810*a*, 810*b* in FIGS. 8A-8B). In such embodiments, the adjunct can include additional fibers that are incorporated into the adjunct such that finished edge(s) can also be formed along, and thus define, at least a portion of the inner-most longitudinal terminal edge(s). For example, an adjunct can include inner-most longitudinal terminal edges that are configured to border a longitudinal slot, like longitudinal slot 210 in FIGS. 2A-2C, of a staple cartridge. In such embodiments, the adjunct can include at least one bridging element that extends between and tethers spaced apart portions of the adjunct together (e.g., portions that are configured to be positioned on opposite sides of the longitudinal slot when the adjunct is coupled to the cartridge). In certain embodiments, the at least one bridging element can be designed to overlap with at least a portion of a cut-line of the adjunct, and thus at least a portion of the longitudinal slot. As a result, the at one least bridging element is severed by the advancement of the cutting element through the longitudinal slot.

In some embodiments, the at least one bridging element can include two or more bridging elements that are spaced apart relative to each other to provide discrete attachments between portions of the adjunct. In embodiments where such portions are configured to be positioned on opposite sides of the longitudinal slot of the cartridge, the discrete attachments can reduce the amount of adjunct material positioned within the advancement path of the cutting element. This material reduction can help to minimize the resistance of the adjunct to the advancement of the cutting element which, among other things, can improve the life of the cutting element and/or reduce the force required to advance the cutting element through the adjunct. In certain embodiments, the at least one bridging element can be formed of a portion of at least one of the top and bottom layers of the adjunct, whereas in other embodiments, the at least bridging element can be formed of separate material. Alternatively, one or more of the at least one bridging element can be positioned outside the advancement path of the cutting element, and thus, can continue to tether the portions of the adjunct after the cutting element is advanced through the longitudinal slot.

FIGS. 10A-10D show another exemplary embodiment of a stapling assembly 1000 having a staple cartridge 1002 and a knitted adjunct 1004 that is disposed on a top or deck surface 1003 of the staple cartridge 1002 and that has one or more finished edges. The staple cartridge 1002 is similar to staple cartridge 200 in FIGS. 1-2C, and therefore common features are not described in detail herein. Further, aside from the differences described below, the adjunct 1004 is similar to adjunct 804 in FIGS. 8A-8B, and therefore common features are not described in detail herein.

The adjunct 1004 can have a variety of configurations. For example, in this illustrated embodiment, the adjunct 1004 includes first and second longitudinal portions 1006, 1008, each having a respective top layer 1010, 1012 (e.g., a tissue-contacting layer) formed of first fibers 1014, a bottom layer 1016, 1018 (e.g., a cartridge-contacting layer) formed of second fibers 1020, and spacer fibers 1022 that are intertwined with and that extend between the respective top and bottom layers 1010, 1012, 1016, 1018 to thereby connect the top and bottom layers. The top and bottom layers 1010, 1012 are similar in structure to the top and bottom layers 806, 810 in FIGS. 8A-8B and the spacer fibers 1022 are similar to the spacer fibers 814 in FIGS. 8A-8B, and therefore comment features are not described in detail herein. Further, at least of a portion of the fibers in the first longitudinal portion 1006 can be the same or different than at least a portion of the fibers of the second longitudinal portion 1008. In this illustrated embodiment, the first fibers 1014 in the first and second longitudinal portions 1006, 1008 are the same type of fibers, the second fibers 1020 in the first and second longitudinal portions 1006, 1008 are the same type of fibers, and the spacer fibers 1022 in the first and second longitudinal portions 1006, 1008 are the same type of fibers.

The first and second longitudinal portions 1006, 1008 can each include additional fibers that form a respective finished edge configured to prevent fraying of the respective top and bottom layers 1010, 1012 therealong, and thus fraying and/or fiber separation of the first fibers 1014 and the second fibers 1020. As shown in greater detail in FIG. 10B, the first longitudinal portion 1006 includes eight additional third fibers 1024*a*, 1024*b*, 1024*c*, 1024*d*, 1024*e*, 1024*f*, 1024*g*, 1024*h*, and the second longitudinal portion 1008 includes eight additional fourth fibers 1026*a*, 1026*b*, 1026*c*, 1026*d*, 1026*e*, 1026*f*, 1026*g*, 1026*h*. Consequently, the first longitudinal portion 1006 includes finished edges 1028*a*, 1028*b*, 1028*c*, 1028*d*, 1028*e*, 1028*f*, 1028*g*, 1028*h*, and the second longitudinal portion 1008 includes finished edges 1030*a*, 1030*b*, 1030*c*, 1030*d*, 1030*e*, 1030*f*, 1030*g*, 1030*h*. While the first and second longitudinal portions 1006, 1008 are each illustrated as having eight additional third and fourth fibers 1024*a*, 1024*b*, 1024*c*, 1024*d*, 1024*e*, 1024*f*, 1024*g*, 1024*h*, 1026*a*, 1026*b*, 1026*c*, 1026*d*, 1026*e*, 1026*f*, 1026*g*, 1026*h*, respectively, and consequently eight respective finished edges 1028*a*, 1028*b*, 1028*c*, 1028*d*, 1028*e*, 1028*f*, 1028*g*, 1028*h*, 1030*a*, 1030*b*, 1030*c*, 1030*d*, 1030*e*, 1030*f*, 1030*g*, 1030*h*, a person skilled the art will appreciate that the amount of additional fibers can depend at least upon the size and shape of the staple cartridge and/or anvil to which the adjunct will be applied, and therefore, the first and second longitudinal portions 1006, 1008 are not limited to the number of additional fibers illustrated in the figures.

The additional third and fourth fibers 1024*a*, 1024*b*, 1024*c*, 1024*d*, 1024*e*, 1024*f*, 1024*g*, 1024*h*, 1026*a*, 1026*b*, 1026*c*, 1026*d*, 1026*e*, 1026*f*, 1026*g*, 1026*h* can have a variety of configurations. In some embodiments, two or more of the additional fibers can be generally identical (nominally identical within manufacturing tolerances) in compositional makeup (e.g., formed of the same material (s)), dimension(s) (e.g., height and/or diameter), and/or in structural configuration (e.g., monofilament or multifilament). In certain embodiments, at least one of the additional fibers can be a monofilament fiber. Alternatively, or in addition, at least one of the additional fibers can be a multifilament fiber. In one embodiment, one portion of the additional fibers are monofilament fibers and the other portion is multifilament fibers. As such, aside from the general overall shape, the specific structural configuration of each of the additional third and fourth fibers 1024*a*, 1024*b*, 1024*c*, 1024*d*, 1024*e*, 1024*f*, 1024*g*, 1024*h*, 1026*a*, 1026*b*, 1026*c*, 1026*d*, 1026*e*, 1026*f*, 1026*g*, 1026*h* is not shown.

Further, as shown, the additional third fibers 1024*a*, 1024*b*, 1024*c*, 1024*d*, 1024*e*, 1024*f*, 1024*g*, 1024*h* are similar in structure and stitch form to the additional fourth fibers 1026*a*, 1026*b*, 1026*c*, 1026*d*, 1026*e*, 1026*f*, 1026*g*, 1026*h*, and therefore for sake of simplicity, the following description is with respect to the additional third fibers 1024*a*, 1024*b*, 1024*c*, 1024*d*, 1024*e*, 1024*f*, 1024*g*, 1024*h*. A person skilled in the art will understand, however, that the following discussion is also applicable to the additional fourth fibers 1026*a*, 1026*b*, 1026*c*, 1026*d*, 1026*e*, 1026*f*, 1026*g*, 1026*h*.

The additional third fibers 1024*a*, 1024*b*, 1024*c*, 1024*d*, 1024*e*, 1024*f*, 1024*g*, 1024*h* can be incorporated into the first longitudinal portion 1006 in a variety of ways to form respective finished edges 1028*a*, 1028*b*, 1028*c*, 1028*d*, 1028*e*, 1028*f*, 1028*g*, 1028*h*. In this illustrated embodiment, as shown in more detail in FIG. 10C, the first additional third fiber 1024*a* is configured as an overcast stitch and interconnects the top and bottom layers 1010, 1016 along their first outer-most longitudinal terminal edges 1010*a*, 1016*a* to form the first finished edge 1028*a*. As a result, the first finished edge 1028*a* of the first longitudinal portion 1006 is formed of the first fibers 1014, the second fibers 1020, and the first additional third fiber 1024*a* and is positioned along, and thus defines, at least a portion of an outer-most longitudinal edge 1032 of the first longitudinal portion 1006. Each remaining additional third fiber 1024*b*, 1024*c*, 1024*d*, 1024*e*, 1024*f*, 1024*g*, 1024*h* is also configured as an overcast stitch and interconnects the top and bottoms layers 1010, 1016 along a respective portion of a second outer-most longitudinal terminal edge 1010*b*, 1014*b* of the top and bottom layers 1010, 1016 to form respective and discrete finished edges 1028*b*, 1028*c*, 1028*d*, 1028*e*, 1028*f*, 1028*g*, 1028*h*. As a result, each remaining finished edge 1028*b*, 1028*c*, 1028*d*, 1028*e*, 1028*f*, 1028*g*, 1028*h* is formed of the first fibers 1014, the second fibers 1020, and respective additional third fiber 1024*b*, 1024*c*, 1024*d*, 1024*e*, 1024*f*, 1024*g*, 1024*h*, and is positioned along, and thus defines, a respective portion of an inner-most longitudinal edge 1034 of the first longitudinal portion 1006.

As further shown, the adjunct 1004 includes bridging elements 1036*a*, 1036*b*, 1036*c*, 1036*d*, 1036*e*, 1036*f* that extend between and connect the first and second longitudinal portions 1006, 1008 of the adjunct 1004 together. While the adjunct 1004 is illustrated as having six bridging elements 1036*a*, 1036*b*, 1036*c*, 1036*d*, 1036*e*, 1036*f*, a person skilled the art will appreciate that the number and structural configuration of the bridging element(s) of the adjunct can depend at least upon the size and shape of the staple cartridge and/or anvil to which the adjunct will be applied and/or the size and shape of a longitudinal slot (e.g., a knife slot) within the cartridge, and therefore, the adjunct 1004 is not limited to the number and/or structural configuration of the bridging elements illustrated in the figures.

The bridging elements 1036*a*, 1036*b*, 1036*c*, 1036*d*, 1036*e*, 1036*f* can have a variety of configurations. For example, in illustrated embodiment, discrete portions of the first and second fibers 1014, 1020 extend between the first and second longitudinal portions 1006, 1008, and as a result, these portions serve as the bridging elements 1036*a*, 1036*b*, 1036*c*, 1036*d*, 1036*e*, 1036*f*. This creates a centralized zone 1040 within the adjunct that is formed of only the first and second fibers 1014, 1020. This results in a lesser amount of material along the cut-line of the adjunct compared to the other portions of the adjunct. In some embodiments, a portion of the spacer fibers can be present within the centralized zone (e.g., the spacer fiber density within the centralized zone is less than the spacer fiber densities within other portions of the adjunct).

As shown in FIGS. 10A-10D, when the adjunct 1004 is releasably secured to the cartridge 1002, the first longitudinal portion 1006 is positioned on a first side of the longitudinal slot 1007 of the cartridge 1002 and the second longitudinal portion 1008 is positioned on a second, opposite side of the longitudinal slot 1007. With respect to the first longitudinal portion 1006, the first finished edge 1028*a* is positioned proximate to and along a portion of a first outer-most longitudinal edge 1005*a* of the top surface 1003 of the cartridge 1002, and each of the remaining finished edges 1028*b*, 1028*c*, 1028*d*, 1028*e*, 1028*f*, 1028*g*, 1028*h* are positioned proximate to and along a respective portion of a first slot edge 1007*a* of the longitudinal slot 1007. Similarly, with respect to the second longitudinal portion 1008, the first finished edge 1030*a* is positioned proximate to and along a portion of a second outer-most longitudinal edge 1005*b* of the top surface 1003 of the cartridge 1002, and each of the remaining finished edges 1030*b*, 1030*c*, 1030*d*, 1030*e*, 1030*f*, 1030*g*, 1030*h* are positioned proximate to and along a respective portion of a second slot edge 1007*b* of the longitudinal slot 1007. Further, as shown in more detail in FIGS. 10B and 10D, the bridging elements at least partially overlap with the longitudinal slot 1007 of the cartridge 1002.

While not shown in FIGS. 10A-10D, in certain embodiments, the adjunct can also include one or more attachment features that extend at least partially along the length of adjunct (e.g., extending in the z-direction) and that are configured to engage the staple cartridge to thereby retain the adjunct on the cartridge prior to staple deployment. The one or more attachment features can have a variety of configurations. For example, the one or more attachment features can be channel attachments that are configured to engage (e.g., press-fit or snap into) the longitudinal slot (e.g., knife slot) formed between opposing longitudinal slot edges in the staple cartridge.

Figure 11A:
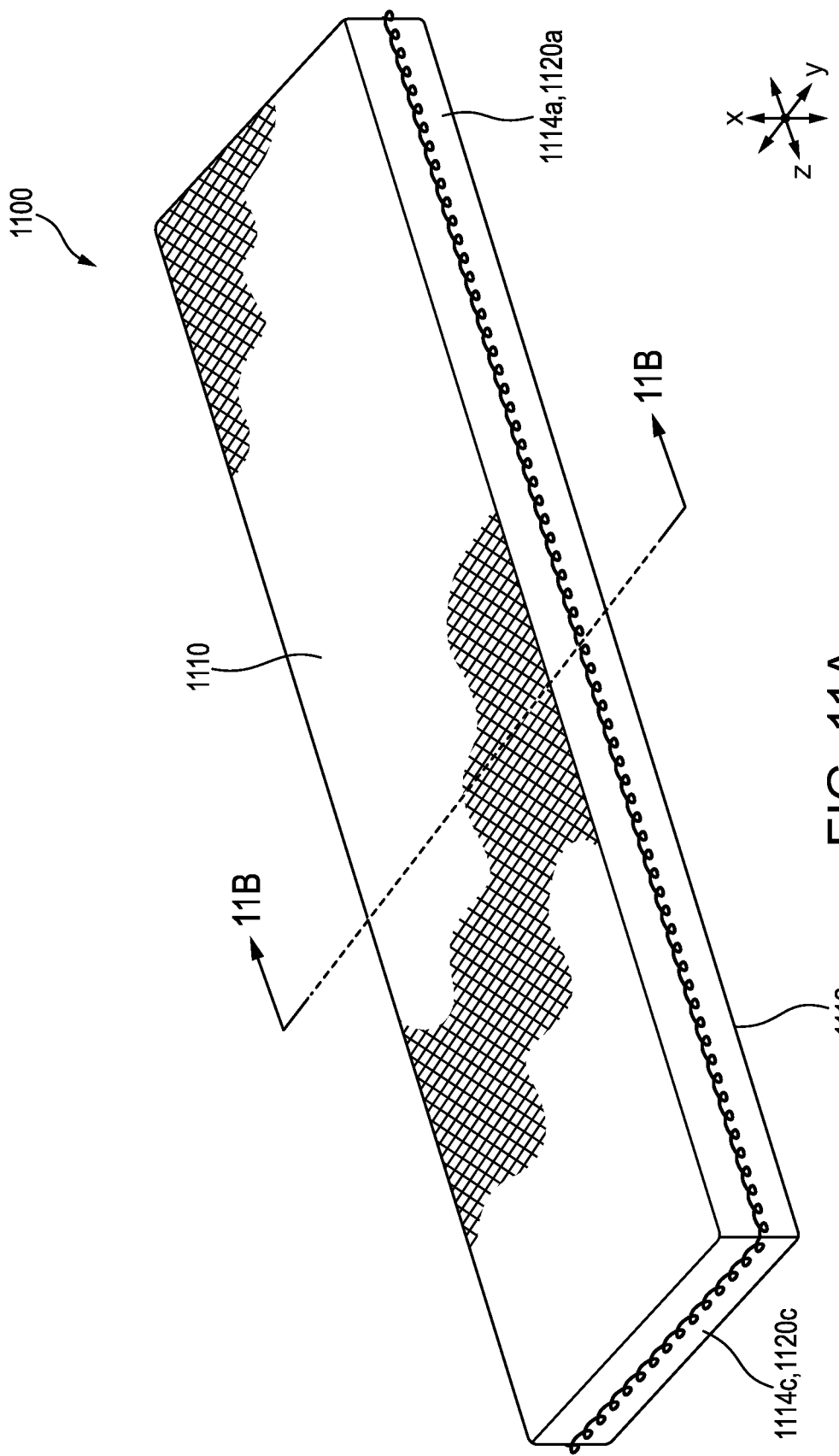
FIG. 11A is a perspective view of another exemplary embodiment of compressible knitted adjunct.
Figure 11B:
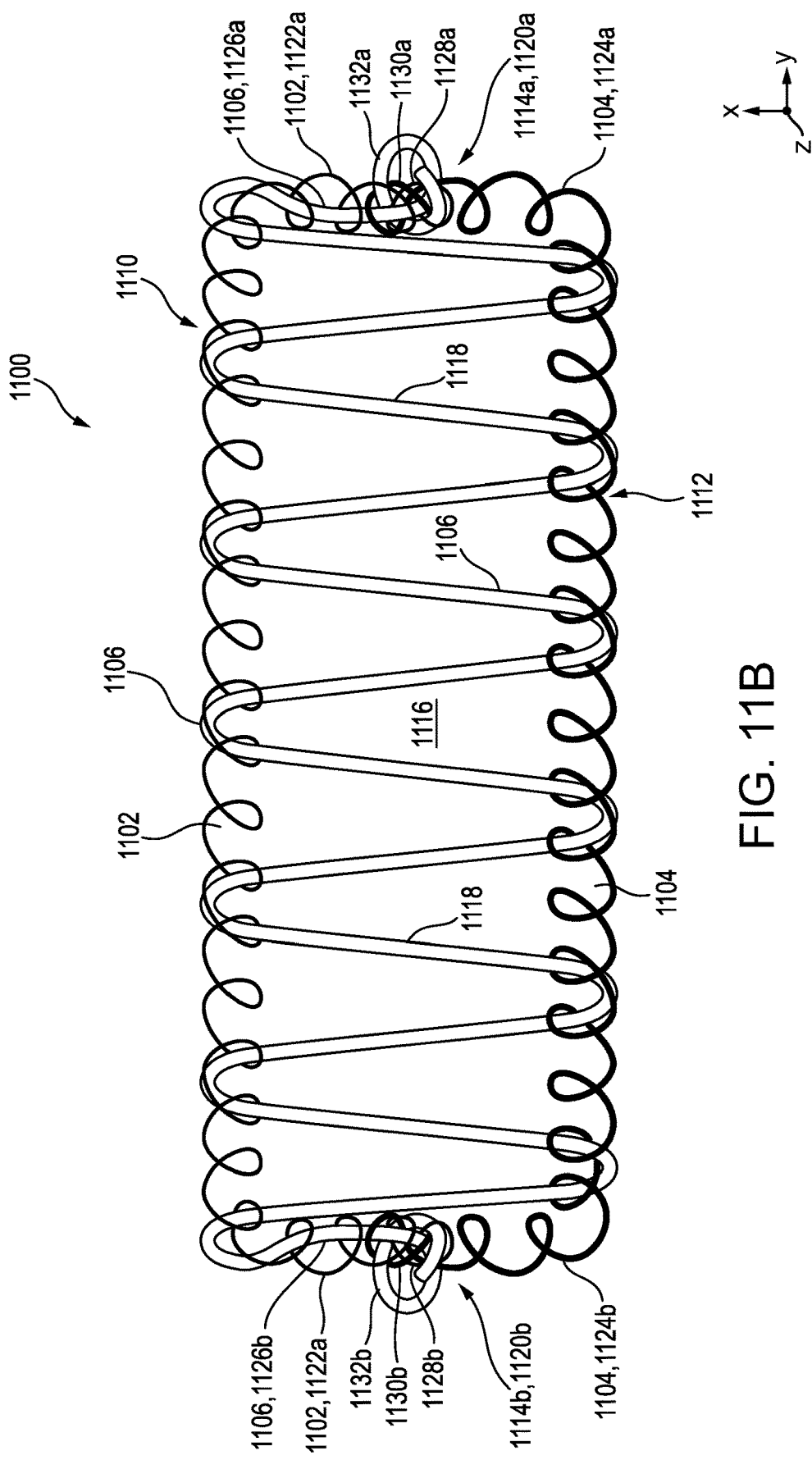
FIG. 11B is a cross-sectional view of the adjunct of FIG. 11A taken at line 11B-11B.

In other embodiments, instead of incorporating additional fiber(s) into the adjunct (e.g., additional fibers 830, 832 in FIGS. 8A-8B) for creating one or more finished edges of the adjunct, the existing fibers of the adjunct (e.g., first fibers 1102, second fibers 1104, and spacer fibers 1106 in FIGS. 11A-11B) can be intertwined together. Alternatively, or in addition, heat can be applied to at least a portion of the existing fibers. For example, a hot blade could be used to melt, and thus fuse, at least a portion of the existing fibers, e.g., along at least a portion of the perimeter of the adjunct. This can avoid the need for additional material (e.g., additional fiber(s) other than the fibers needed to form the top, bottom, and core layers of the adjunct), and thus, among other things, can decrease the overall material cost and/or manufacturing cost of the adjunct.

FIGS. 11A-11B is one exemplary embodiment of a knitted adjunct 1100 having at least one finished edge formed of fibers that also form other portions of the adjunct. In this illustrated embodiment, the adjunct 1100 includes first fibers 1102, second fibers 1104, and spacer fibers 1106 that are intertwined to form a top layer 1110 (e.g., a tissue-contacting layer), a bottom layer 1112 (e.g., a cartridge-contacting layer), and at least one finished edge (only three finished edges 1114*a*, 1114*b*, 1114*c* are illustrated) extending between the top and bottom layers 1110, 1112. For sake of simplicity, only one first fiber 1102, second fiber 1104, and spacer fiber 1106 is illustrated in FIG. 11B. A person skilled in the art will appreciate that the following discussion is also applicable to the remaining first, second, and spacer fibers of the adjunct.

The first fibers 1102, the second fibers 1104, and the spacer fibers 1106 can have a variety of configurations. For example, in some embodiments, the first fibers 1102, the second fibers 1104, and the spacer fibers 1106 can be generally identical (e.g., nominally identical within manufacturing tolerances) in compositional makeup (e.g., formed of the same material(s)), dimension(s) (e.g., height and/or diameter), and/or in structural configuration (e.g., monofilament or multifilament), whereas in other embodiments, they can be different. In certain embodiments, the first and second fibers 1102, 1104 can be generally identical (e.g., nominally identical within manufacturing tolerances) and the spacer fibers 1106 can be different. For example, in certain embodiments, the first and second fibers 1102, 1104 are multifilament fibers, and the spacer fibers 1106 are monofilament fibers. As such, aside from the general overall shape, the specific structural configuration of each of the first fibers 1102, the second fibers 1104, and the spacer fibers 1106 is not shown.

The top and bottom layers 1110, 1112 can have a variety of structural configurations. As shown in more detail in FIG. 11B, the first fibers 1102 and the spacer fibers 1106 are intertwined to form the top layer 1110 and the second fibers 1104 and the spacer fibers 1106 are intertwined to form the bottom layer 1112. Thus, in this illustrated embodiment, the first fibers 1102 are not present in the bottom layer 1112 and the second fibers 1104 are not present in the top layer 1110. In other embodiments, at least a portion of the first fibers 1102 can be present within the bottom layer 1112 and/or at least a portion of the second fibers 1104 can be present within the top layer 1110.

In some embodiments, the first fibers 1102 of the top layer 1110 and/or second fibers 1104 of the bottom layer 1112 can be knitted in a respective predetermined pattern. In certain embodiments, the predetermined pattern of the first fibers 1102 within the top layer 1110 and the predetermined pattern of the second fibers 1104 of the bottom layer 1112 can be generally identical (e.g., nominally identical within manufacturing tolerances), whereas in other embodiments, the predetermined patterns can be different. While the first fibers 1102 of the top layer 1110 and the second fibers 1104 of the bottom layer 1112 can each be knitted in various patterns, in certain embodiments, the first fibers 1102 can be knitted into a first Raschel knit pattern and the second fibers 1104 can be knitted into a second Raschel knit pattern that is the same or different than the first Rachel knit pattern. Further, in some embodiments, the fiber density of the top layer 1110 can be different than the fiber density of the bottom layer 1112. A person skilled in the art will appreciate that the first fibers 1102 and the second fibers 1104 can be randomly or repeatedly knitted or woven within the top and bottom layers 1110, 1112, respectively. As such, and for sake of simplicity, the top and bottom layers 1110, 1112 are generally illustrated, and thus the specific structural configurations of the top and bottom layers 1110, 1112 are not limited to what is depicted in the figures.

The portions of the spacer fibers 1106 that extend between the top and bottom layers 1110, 1112 can form an intermediate layer 1116, and thus, are positioned between the top and bottom layers 1110, 1112. While these portions can have a variety of configurations, in this illustrated embodiment, as shown in FIG. 11B, they are arranged in such a manner that form standing fibers 1118. The standing fibers 1118 can be configured to bend or compress in response to force being applied to the adjunct 1100.

The standing fibers 1118 can have a variety of orientations within the intermediate layer. For example, in some embodiments, as shown in FIG. 11B, the standing fibers 1118 have a general columnar configuration, meaning they are generally oriented in adjacent columns. In other embodiments, the standing fibers 1118 can be angled or slanted to favor an organized collapse or bend in a first direction in response to force(s) applied to the adjunct (e.g., compressive forces through tissue (T) positioned against the top layer 1110). Alternatively, the standing fibers 1118 can be angled or slanted to favor an organized collapse in a second direction opposite the first direction in response to the applied force(s). Alternatively, the standing fibers 1118 can include a first group that are angled or slanted to favor bending in the first direction and a second group of the standing fibers that are angled or slanted to favor bending in the second direction.

As further shown in FIGS. 11A-11B, the adjunct 1100 includes four finished edges (only three finished edges 1114a, 1114b, 1114c are illustrated) in which each finished edge extends between the top and bottom layers 1110, 1112. Further, one or more of the finished edges 1114a, 1114b, 1114c can be positioned at least partially along, and thus at least partially define, an outer-edge of the adjunct 1100. For example, in this illustrated embodiment, the adjunct 1100 has four outer-most edges (only three outer-most edges 1120a, 1120b, 1120c) in which the first finished edge 1114a is positioned entirely along the first outer-most edge 1120a, the second finished edge 1114b is positioned entirely along the second outer-most edge 1120b, the third finished edge 1114c is positioned entirely along the third outer-most edge 1120c, and the fourth finished edge (obstructed) is positioned entirely along the fourth outer-most edge (obstructed). As a result, the four finished edges define the entire outer-most perimeter of the adjunct 1100.

Each finished edge is formed of respective portions of the first fibers 1102, the second fibers 1104, and the spacer fibers 1106. The first fibers 1102, the second fibers 1104, and the spacer fibers 1106 can interact in a variety of ways to effect the finished edges. In this illustrated embodiment, each finished edge is structurally similar and includes respective portions of the first fibers, the second fibers, and the spacer fibers intertwined together. While only the first and second finished edges are illustrated in detail, a person skilled in the art will appreciate the following discussion is also applicable to the third finished edge 1114c and the fourth finished edge.

As shown in greater detail in FIG. 11B, the first finished edge 1114a includes a first portion 1122a of the first fibers 1102, a first portion 1124a of the second fibers 1104, and a first portion 1126a of the spacer fibers 1106 that are intertwined together. In addition, the free ends 1128a of the first portion 1122a of the first fibers 1102, the free ends 1130a of the first portion 1124a of the second fibers 1104, and the free ends 1132a of the first portion 1126a of the spacer fibers 1106 can be knotted together, as shown in FIG. 11B. Similarly, as shown in FIG. 11B, the second finished edge 1114b includes a second portion 1122b of the first fibers 1102, a second portion 1124b of the second fibers 1104, and a second portion 1126b of the spacer fibers 1106 that are intertwined together. In addition, the free ends 1128b of the second portion 1122b of the first fibers 1102, the free ends 1130b of the second portion 1124b of the second fibers 1104, and the free ends 1132b of the second portion 1126b of the spacer fibers 1106 can be knotted together, as shown in FIG. 11B.

While not shown, in certain embodiments, the adjunct 1100 can also include additional finished edge(s) that are configured to be positioned adjacent to and along a respective slot edge of a longitudinal slot formed within a cartridge to which the adjunct is intended to be releasably attached thereto. In such embodiments, for example, at least one additional finished edge can be formed of respective portions of the first fibers 1102, the second fibers 1104, and the spacer fibers 1106.

While the adjuncts 804, 900, 1004 in FIGS. 8A-10D each include finished edges that are formed by additional fibers, and the adjunct 1100 in FIGS. 11A-11B includes finished edges that are formed by existing fibers, in other embodiments, an adjunct can have a combination of different types of finished edges. For example, in certain embodiments, an adjunct can have at least one finished edge that is formed by an additional fiber(s) (e.g., first finished edge 34 in FIG. 8B) and at least one finished edge that is formed by a portion of existing fibers otherwise present in the adjunct (e.g., first finished edge 1114a in FIGS. 11A-11B).

Alternatively, or in addition, the adjunct can include an absorbable film that is disposed over at least a portion of a tissue-facing surface of an outer layer and/or inner layer. The absorbable film can substantially protect the fibers of the underlying layer(s) from being exposed to forces that would otherwise lead to fraying, pulling, and/or separating. For example, in certain embodiments, an absorbable film can be used to form at least a portion of one or more finished edges of the adjunct. Further, the absorbable film can substantially prevent tissue from causing the adjunct to prematurely detach from the cartridge while the tissue slides across the adjunct. That is, the absorbable film can minimize edge conditions, and thus decrease the friction that would otherwise be present on the tissue-contacting surface(s) of the adjunct.

The absorbable film can have a variety of configurations. In some embodiments, the absorbable film can have a thickness that is less than or equal to about 15 microns, e.g., from about 5 microns to 15 microns, or from about 8 microns to 11 microns. In one embodiment, the absorbable film can be formed of polydioxanone. The absorbable film can be attached to a knitted structure in a variety of ways. For example, in one embodiment, the absorbable film can be attached by heating the film (e.g., equal to or above a glass transition temperature of the film material) and then pressing the film onto the knitted structure to thereby create a bond therebetween. Alternatively, at least a portion of the knitted structure (e.g., a portion of the fibers of the bottom layer) can be heated (e.g., above 85° C.) and then pressed against the film.

FIG. 12 illustrates one exemplary embodiment of a stapling assembly 1200 that includes a staple cartridge 1202 and a knitted adjunct 1204 disposed on a top or deck surface 1203 of the cartridge 1202. The staple cartridge 1202 is similar to staple cartridge 200 in FIGS. 1-2C, and therefore common features are not described in detail herein.

The adjunct 1204 includes a knitted structure 1206 with an absorbable film 1208 disposed on at least a portion thereof. The knitted structure includes a top layer 1210, a bottom layer 1212, and a core layer 1214 extending therebetween. The top layer 1210, the bottom layer 1212, and the core layer 1214 are similar to the top layer 1110, the bottom layer 1112, and the intermediate layer 1116 in FIGS. 11A-11B, and therefore common features are not described herein. As shown, the absorbable film 1208 is disposed on all tissue-facing surfaces of the knitted structure 1206, which, in this illustrated embodiment, includes a top-tissue facing surface 1216 (e.g., extending in the YZ plane), a first longitudinal side surface 1218a (e.g., extending in the XZ plane), a second opposing longitudinal side surface 1218b, a first lateral side surface 1220a (e.g., extending in the XY plane), and a second opposing lateral side surface (obstructed). In other embodiments, the absorbable film is not disposed on all tissue-facing surfaces of the knitted structure, e.g., the first lateral side surface and/or the second lateral side surface.

Attachment Features

In general, the knitted adjuncts described herein are designed and positioned atop a staple cartridge for use in a stapling procedure. When the staples are fired (deployed) from the cartridge, the staples penetrate through the adjunct and into tissue. Prior to the adjunct being penetrated by the staples, the adjunct may become dislodged or misaligned from the staple cartridge. That is, when the staple cartridge is being placed into position, the adjunct may be dislodged by coming into contact with a portion of a surgical site. In order to keep the adjunct aligned and secured on the staple cartage prior to firing the staples, one or more surfaces features may be arranged within the adjunct. The one or more surface features (e.g., one or more recesses) may be woven, thermoformed, or mechanically positioned within the adjunct.

As discussed above, the knitted adjuncts are formed of fibers that are knitted or woven together. In certain embodiments, the adjuncts can be designed such that one or more surface features can be formed within the adjunct. The one or more surface features are configured to substantially, or completely, align and secure the adjunct to the cartridge deck prior to staple deployment. As a result, the adjunct can remain secured to the cartridge deck when exposed to forces that would otherwise cause the adjunct to separate from the cartridge deck prior to stapling of the adjunct to tissue. The one or more surface features can also decrease the likelihood of misalignment of the adjunct prior to stapling, as compared to conventional adjuncts (e.g., adjuncts without one or more surface features).

The one or more surface features can be formed in a variety of ways. For example, in some embodiments, the surface features can be created in the adjunct after fabrication. For example, using a solvent, a knitting operation, a heat operation, a die cutting operation, a laser cutting operation, an ultrasonic cutting operation, a stamping or punching operation (e.g., a mechanical pressing), or a combination of these techniques. In some embodiments, the surface features can be knitted into the bottom-most layer (e.g., cartridge-contacting layer) of the adjunct. In other embodiments, the surface features can be thermoformed in the adjunct using a heated mold. Alternatively, or in addition to, the surface features can be thermoformed in the adjunct by heating the stapling cartridge and positioning the adjunct onto the heated cartridge deck so that the adjunct conforms to the shape of the cartridge deck, including any one or more attachment features (e.g., projections) of the cartridge deck.

In some embodiments, the one or more surface features can have a minimum diameter that is smaller than the diameter of the staple legs. Alternatively, or in addition, the one or more surface features a can have maximum diameter that is greater than the circumference (e.g., outer diameter) of the one or more attachment features of the cartridge to form a friction or press-fit. In certain embodiments, the one or more surface features can be sized so as to receive two or more attachment features of the cartridge.

Figure 13A:
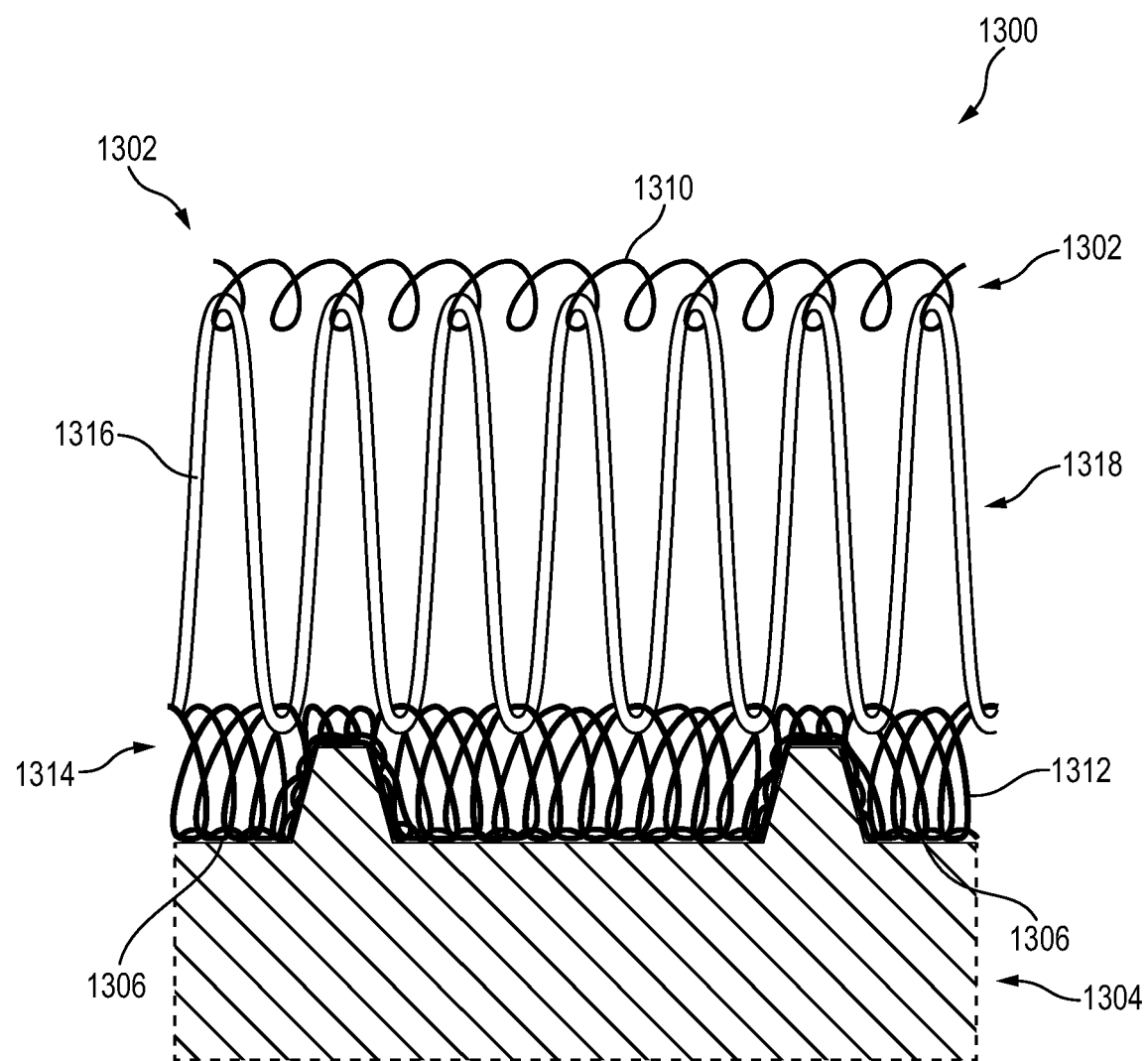
FIG. 13A is a cross-sectional view of another exemplary embodiment of a stapling assembly having a compressible knitted adjunct releasably retained on a staple cartridge.
Figure 13B:
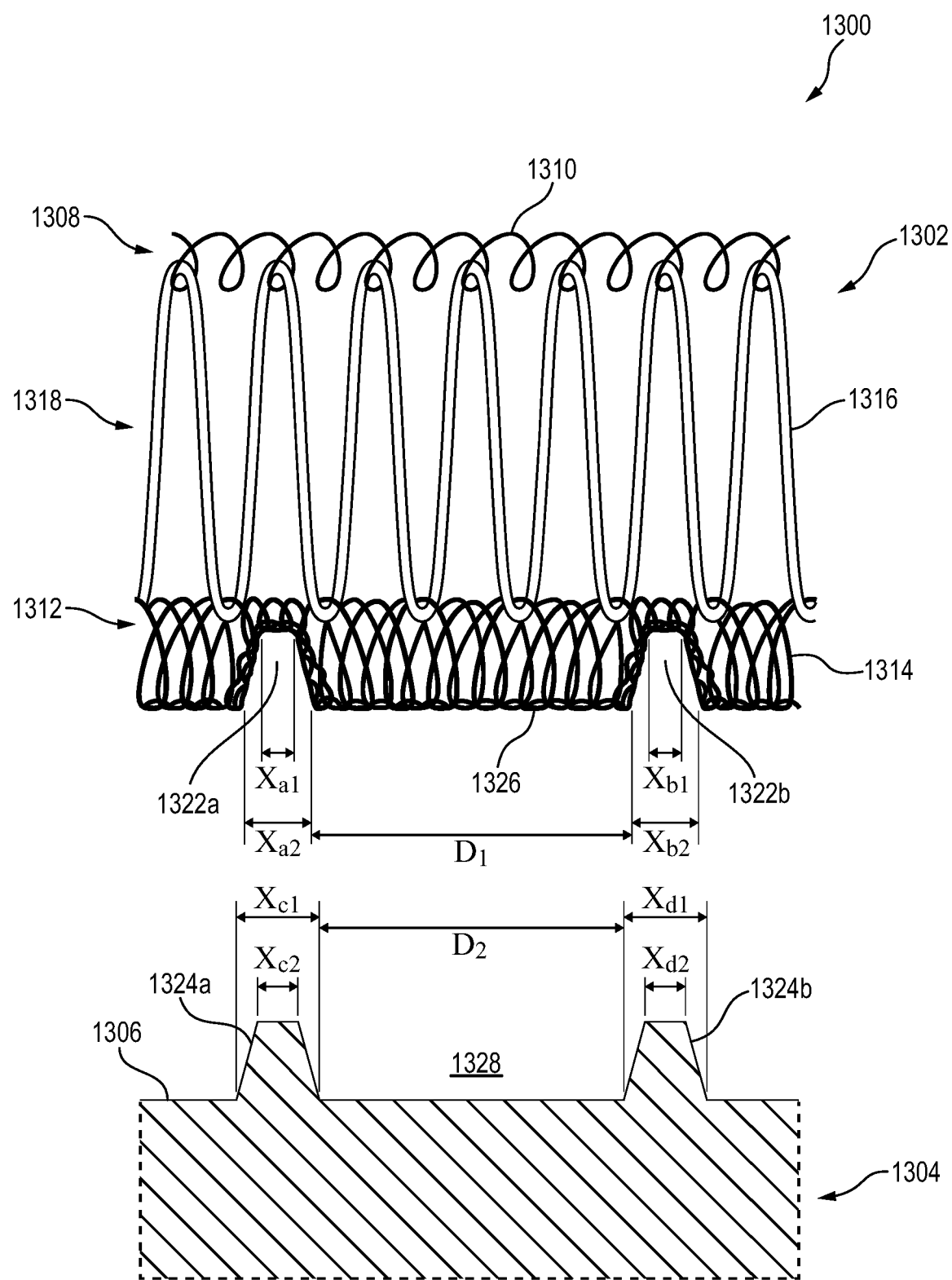
FIG. 13B is a cross-sectional view of the compressible knitted adjunct and staple cartridge of FIG. 13A in a detached configuration prior to being releasably retained.

FIG. 13A illustrates a portion of another exemplary embodiment of a stapling assembly 1300 that includes a knitted adjunct 1302 disposed on a top or deck surface 1306 of a staple cartridge 1304, with FIG. 13B illustrating the adjunct and the cartridge prior to being releasably coupled together. The adjunct 1302 includes a first knitted layer 1308 (e.g., a top or tissue-contacting layer) formed of at least first fibers 1310, a second knitted layer 1312 (e.g., a bottom or cartridge-contacting layer) formed of at least second fibers 1314, and spacer fibers 1316 intertwined with and extending between the first and second knitted layers 1308, 1312 to thereby connect the first and second knitted layers 1308, 1312 together. The portions of the spacer fibers 1316 that extend between the first and second knitted layers 1308, 1312 form a core layer 1318 of the adjunct 1302. For sake of simplicity, only one first fiber 1310, second fiber 1314, and spacer fiber 1316 is being illustrated. A person skilled in the art will appreciate that the following discussion is also applicable to the remaining first, second, and spacer fibers of the adjunct.

In some embodiments, the first fibers 1310 of the first knitted layer 1308 can be knitted or woven into a first predetermined pattern and/or the second fibers 1314 of the second knitted layer 1312 can be knitted or woven into a second predetermined pattern. In certain embodiments, the first and second predetermined patterns can be generally identical (e.g., nominally identical within manufacturing tolerances), whereas in other embodiments, the first and second predetermined patterns can be different. Further, in some embodiments, the fiber density of the first knitted layer 1308 can be different than the fiber density of the second knitted layer 1312. While the first fibers 1310 and the second fibers 1314 can be knitted or woven in various patterns, in certain embodiments, the first fibers 1310 can be knitted into a first Raschel knit pattern and the second fibers 1314 can be knitted into a second Raschel knit pattern that is the same or different than the first Raschel knit pattern. A person skilled in the art will appreciate that the first fibers 1310 and the second fibers 1314 can be randomly or repeatedly knitted or woven within the first and second knitted layers 1308, 1312, respectively. As such, and for sake of simplicity, the first and second knitted layers 1308, 1312 are generally illustrated, and thus the specific structural configurations of the first and second knitted layers 1308, 1312 are not limited to what is depicted in the figures.

The first fibers 1310, the second fibers 1314, and the spacer fibers 1316 can have a variety of configurations. For example, in some embodiments, the first fibers 1310, the second fibers 1314, and the spacer fibers 1316 can be generally identical (e.g., nominally identical within manufacturing tolerances) in compositional makeup (e.g., formed of the same material(s)), dimension(s) (e.g., height and/or diameter), and/or in structural configuration (e.g., monofilament or multifilament), whereas in other embodiments they are different. In other embodiments, the first and second fibers 1310, 1314 can be generally identical (e.g., nominally identical within manufacturing tolerances) and the spacer fibers 1316 can be different. For example, in certain embodiments, the first and second fibers 1310, 1314 can be multifilament fibers, and the spacer fibers 1316 can be monofilament fibers. As such, aside from the general overall shape, the specific structural configuration of each of the first fibers 1310, the second fibers 1314, and the spacer fibers 1316 is not shown.

As further shown in FIG. 13B, which the adjunct includes one or more surface features formed within the second knitted layer 1312, which in this illustrated embodiment are in the form of recesses (only two recesses 1322a, 1322b are being illustrated). The one or more recesses are configured to receive and engage respective attachment features of the cartridge 1304, as shown in FIG. 13A, which in this illustrated embodiment are in the form of projections 1324a, 1324b that each extend outward from the top or deck surface 1306 of the cartridge 1304. The recesses 1322a, 1322b can be formed by manipulating portions of the second fibers 1314 within the second knitted layer 1312 (e.g., melting or further knitting). In this illustrated embodiment, the perimeter of the recesses 1322a, 1322b are defined by melted portions of the second fibers 1314.

The recesses 1322a, 1322b and projections 1324a, 1324b can have variety of configurations. For example, in this illustrated embodiment, the recesses 1322a, 1322b have an inverted conical-shape, and therefore a varying diameter that decreases as the recesses 1322a, 1322b extends into the second knitted layer 1312. As such, each recess 1322a, 1322b extends from a maximum diameter $X_{1a}$, $X_{2a}$ to a minimum diameter $X_{1b}$, $X_{2b}$. Further, the projections 1324a, 1324b have a conical-shaped with a varying diameter that decreases as the projections 1324a, 1324b extend outward from the top or deck surface 1306. As such, each projection extends 1324a, 1324b from a maximum diameter $X_{1c}$, $X_{1c}$ to a minimum diameter $X_{2c}$, $X_{2d}$. While the recesses 1322a, 1322b and projections 1324a, 1324b are illustrated as having complementary conical-shapes, a person skilled in the art will appreciate that the recesses can have other complementary shapes, such as squares, half-circles, triangles, etc. Further, while the recesses 1322a, 1322b are illustrated as being generally uniform (e.g., uniform within manufacturing tolerances), in other embodiments, at least a portion of the recesses can differ.

The difference between the maximum diameters $X_{1a}$, $X_{1b}$ and the maximum diameters $X_{2a}$, $X_{2b}$ can allow for a friction fit to be formed between the recesses 1322a, 1322b and the projections 1324a, 1324b. In this illustrated embodiment, the maximum diameters of the recesses 1322a, 1322b are smaller than the maximum diameters of the projections 1324a, 1324b prior to the engagement. As a result, an interference fit can be created between the portions of the second fibers 1314 that contact the projections 1324a, 1324b. This friction force can aid in securing the adjunct 1302 to the staple cartridge 1304. In other embodiments, the maximum diameters of the recesses 1322a, 1322b can be larger than the maximum diameters of the projections 1324a, 1324b prior to the engagement.

Further, while not shown, the minimum diameters $X_{1a}$, $X_{1b}$ of the recesses 1322a, 1322b within the adjunct 1302 can be smaller than the diameter of staple legs (e.g. maximum diameter of the wire that forms the staple legs) that at least partially disposed within the staple cartridge 1304. As a result, when the adjunct 1302 is releasably coupled to the cartridge 1304, and the recesses 1322a, 1322b are also configured to overlap with the staple cavities of the cartridge 1304, like staple cavities 212, 214 in FIGS. 2A-2C, the portions of the staple legs extending beyond the top or deck surface 1306 of the cartridge 1304 can also engage the recesses of the adjunct 1302. This can also create a friction fit therebetween and further secure the adjunct to the staple cartridge prior to staple deployment.

As further shown in FIG. 13B, due to the spaced apart arrangement of the recesses 1322a, 1322b in the second knitted layer 1312, a projection 1326 is formed between the recesses 1322a, 1322b with a maximum diameter of $D_1$. Additionally, due to the spaced arrangement of the projections 1324a, 1324b on the top surface 1306 of the cartridge 1304, a complementary recess 1328 is formed between the projections 1326a, 1326b with a maximum diameter of $D_2$. As shown in FIG. 13A, the projection 1326 is received within and engages the recess 1328 when the adjunct 1302 is coupled to the cartridge 1304. In this illustrated embodiment, the maximum diameter $D_1$ of the projection 1326 is larger than the maximum diameter $D_2$ of the recess 1328 prior to engagement. As a result, this can create an additional interference fit between the adjunct 1302 and the cartridge 1304. This can also increase the friction between the recesses 1322a, 1322b and the projections 1324a, 1324b as the different in diameter will push the second fibers 1314 at the perimeter of the recesses 1322a, 1322b further towards and against the projections 1324a, 1324b (e.g., in a y-direction).

In certain embodiments, the recesses are formed in the second knitted layer of the adjunct by thermoforming the second knitted layer on a heated mold having mold features, which are the inverse shape of the desired shape for the recesses. The mold features are similar in shape to the attachment features, but can be either larger or smaller than the dimensions of the attachment features. If the mold features have smaller dimensions than the attachment features, this will ensure a snug, friction fit between the adjunct and the staple cartridge.

In order to form the recesses in the adjunct, the heated mold is heated to a specific temperature (e.g., at or above the glass transition temperature of the second fibers of the second knitted layer) and then the adjunct is pressed onto, into, and/or against the heated mold. In some embodiments, the mold features can be the same or different compared to one another.

Upon engagement with the heated mold, the adjunct forms, or molds, into the mold features of the heated mold, creating the recesses within the second knitted layer. The portion of the second knitted layer which comes into contact with the mold features of the heated mold are thermoformed into the shape of the mold features. Once the heated mold is released from the second knitted layer, the second knitted layer retains the shape of the mold features. The recesses are configured to permit the progressive release of the adjunct from the staple cartridge. One advantage of the thermoformed recesses may include having an adjunct with a more complex shape which custom fits with a corresponding staple cartridge while sustaining a simpler manufacturing process, for example. In certain embodiments, the cartridge deck and the mold features correspond to the shape of the attachment features of the staple cartridge.

In other embodiments, thermoforming of the adjunct can occur by heating the staple cartridge deck. The cartridge can be heated to a temperature above, at, or close to the glass transition temperature of the material, or materials, of the bottom layer (e.g., cartridge-contacting layer) of the adjunct. The adjunct can then be placed over and pushed down onto the staple cartridge and staples disposed therein. Since the adjunct is heated to a temperature above, at, or slightly below the glass transition temperature of material the adjunct is formed from, the adjunct can take a new permanent shape around the attachment features of the staple cartridge and/or around any of the staple legs extending from the top surface of the cartridge.

For example, the staple cartridge can include projections extending from the cartridge deck and, when the adjunct is pushed onto the heated cartridge deck and attachment features, the adjunct can be permanently deformed around the attachment features. In such instances, the adjunct tightly grips the attachment features until the adjunct is pushed off the attachment features by the staples. Similarly, the adjunct can permanently deform around and tightly grip the heated staple legs. In one embodiment, the minimum diameter of the newly-formed recesses within the adjunct can be smaller than the diameter of the staple legs. During the forming process of the recesses, the pressure is applied to the adjunct until the temperature of the staple cartridge, the staples, and/or the adjunct is well below, or at least below, the glass transition temperature of the materials comprising the adjunct. Alternatively, the pressure can be removed when the temperature of the stapling assembly is at or above the glass transition temperature of the materials comprising the adjunct.

In other embodiments, an adjunct can include knitted recesses that are configured to receive and engaged with one or more attachment features of a staple cartridge. For example, the as the adjunct is knitted, portions of the second fibers of the second knitted layer can be knitted in such a way to define a perimeter of the recesses within the second knitted layer. Alternatively, or in addition, additional fibers can be incorporated into the bottom layer so as to at least partially define the perimeter of the recesses Fiber Interconnectivity and Adjunct Compressibility An adjunct is stapled to tissue under various stapling conditions (e.g., tissue thickness, height of formed staple, intra-tissue pressure). Depending on the stapling condition, one can determine an effective amount of stress that the adjunct needs to be able to apply to the tissue to prevent tissue tearing and leakage. For example, in one embodiment, an effective amount of stress is at least about 3 $gf/mm^2$. In order for the adjunct to provide an effective amount of stress to the tissue, the adjunct can be designed to effectively compensate for the various stapling conditions. As such, the adjunct can be tailored to assume different compressed heights when stapled to tissue.

The compressibility profile of the adjunct can therefore be controlled by at least the structural configuration of the fibers and the interconnectivity between them. As a result, the structural configuration of the fibers can be tailored to effect an adjunct with desirable mechanical properties for stapling tissue. As there is a finite range of intra-tissue pressures, tissue thicknesses, and formed staple heights, one can determine appropriate material and/or geometric structures for the adjunct that can be effective in applying a substantially continuous desired stress to the tissue (e.g., 3 $gf/mm^2$) when stapled thereto for a given amount of time (e.g., at least 3 days) over a range of stapling conditions. That is, as described in more detail below, the present adjuncts are formed of compressible materials and geometrically configured so as to allow the adjunct to compress to various heights in predetermined planes when stapled to tissue. Further, this varied response by the adjunct can also allow the adjunct to maintain its application of a continuous desired stress to the tissue when exposed to fluctuations in intra-tissue pressure that can occur when the adjunct is stapled to tissue (e.g., a spike in blood pressure).

As discussed above, the spacer fibers are intertwined with the first and second fibers of the top and bottom layers, respectfully, to thereby connect the top and bottom layers in a spaced apart relation. As such, the spacer fibers are interconnected with the first fibers at first interconnections and with the second fibers at second interconnections. The portions of the spacers fibers that extend between the top and bottom layers thereby form an intermediate layer of the adjunct. While these portions can have a variety of configurations, these portions can be arranged in such a manner that form standing fibers. The standing fibers can be configured to bend or compress in response to force being applied to the adjunct. As a result, the manner in which the spacer fibers interact with the first and second fibers (e.g., the first and second interconnections) can control, at least in part, the standing fibers stiffness or ability to bend under compression which, in turn, controls, at least in part, the overall compressibility of the adjunct. Thus, in some embodiments, the number, location, and tightness of the interconnections can be varied laterally, longitudinally, or thru the thickness of the adjunct to effect different stiffnesses within the adjunct.

In some embodiments, the first and second interconnections have a generally uniform structure (e.g., nominally identical within manufacturing tolerances), whereas in other embodiments, the first and second interconnections are different. The first and second interconnections can have a variety of configurations. For example, in some embodiments, the first interconnections and/or the second interconnection can be single-looped knots. In other embodiments, the first interconnections and/or the second interconnections can be multi-looped knots, for example, as shown in FIGS. 14A-17B. In certain embodiments, the first interconnections can be single-looped knots and the second interconnections can be multi-looped knots (see FIG. 20).

The first and/or second interconnections can be in the form of any suitable knot type. The type of knots that are used can affect the stiffness of the intermediate layer, and consequently, the compression behavior of the adjunct. For example, if loose knots are used, the intermediate layer can be less stiff or can have a lower modulus of elasticity. Alternatively, if tight knots are used, the intermediate layer can be stiffer or have a higher modulus of elasticity. The intermediate layer can utilize any suitable type, or types, of knots.

Figure 14A:
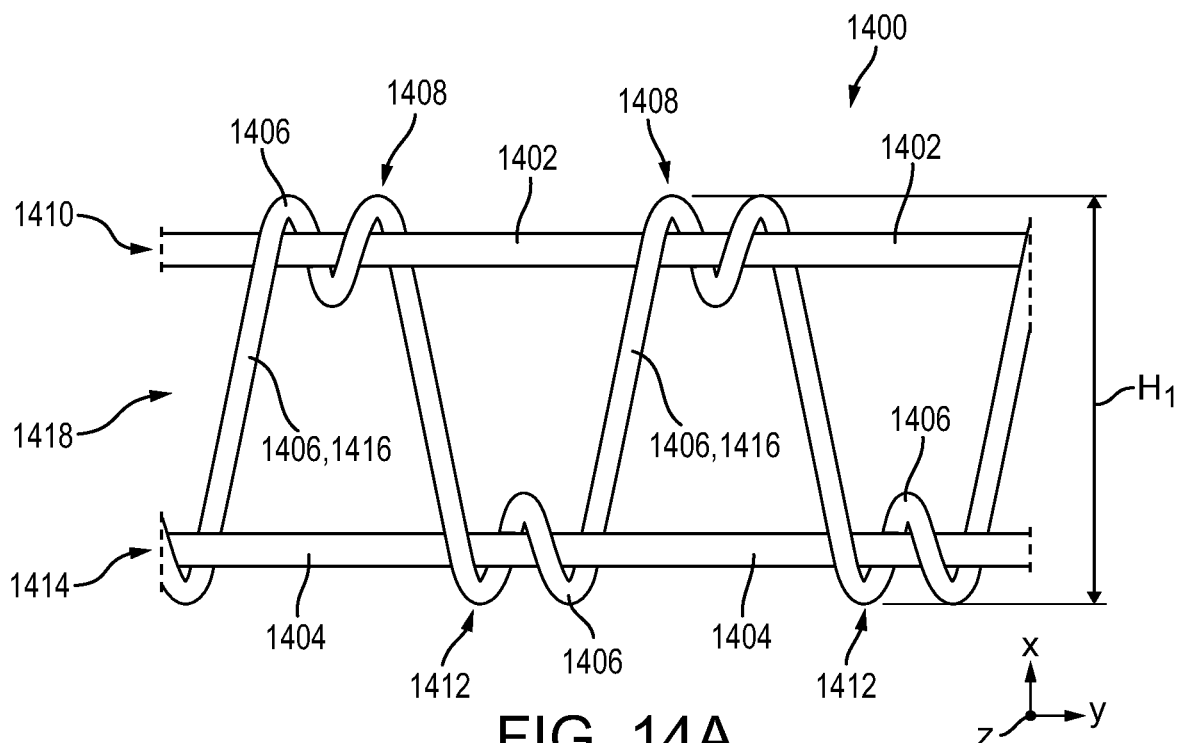
FIG. 14A is a cross-sectional view of an exemplary embodiment of a compressible knitted adjunct in an uncompressed state.
Figure 14B:
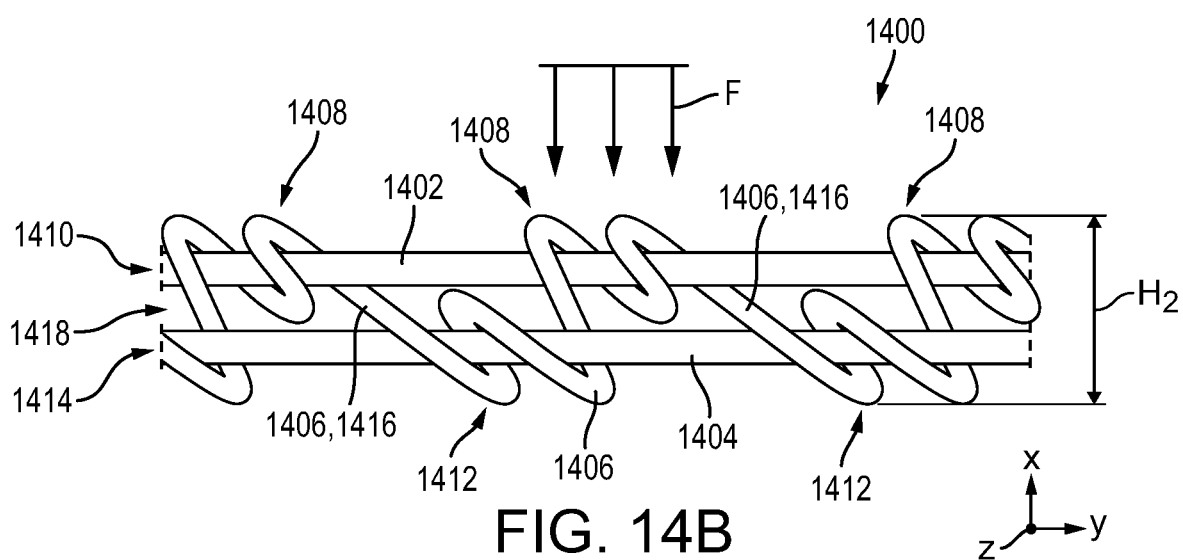
FIG. 14B is a cross-sectional view of the adjunct of FIG. 14A in a first compressed state.

FIGS. 14A-14B is another exemplary embodiment of a knitted adjunct 1400 that includes first fibers 1402, second fibers 1404, and spacer fibers 1406. For sake of simplicity, only one first fiber 1402, second fiber 1404, and spacer fiber 1406 is being illustrated. A person skilled in the art will appreciate that the following discussion is also applicable to the remaining first, second, and spacer fibers of the adjunct.

The spacer fibers 1406 and the first fibers 1402 are interconnected at first interconnections 1408 to form a top layer 1410. The spacer fibers 1406 and the second fibers 1404 are interconnected at second interconnections 1412 to form a bottom layer 1414. The first and second interconnections 1408, 1412 can have a variety of configurations. For example, as shown, the first interconnections 1408 are in the form of first knots having the spacer fibers 1406 multi-looped about the first fibers 1402 and the second interconnections 1412 are each in the form of second knots having the spacer fibers 1406 multi-looped about the second fibers 1404. While the first and second knots 1408, 1412 are illustrated as being structurally similar, in other embodiments, the first and second knots can be different. Further, as described in more detail below, the first knots 1408 and the second knots 1412 are schematically illustrated as having a loose knot configuration.

Further, the portions of the spacer fibers 1406 that extend between the top and bottom layers 1410, 1414 form an intermediate layer 1418 that is positioned between the top and bottom layers 1410, 1414. While these portions can have a variety of configurations, in this illustrated embodiment, they are arranged in such a manner that form standing fibers 1416. The standing fibers 1416 can be have a variety of orientations within the intermediate layer 1418, such as a generally columnar configuration, as shown, meaning they are generally oriented in adjacent columns. The standing fibers 1416 can be configured to bend or compress in response to force being applied to the adjunct 1400, as schematically illustrated in FIG. 14B.

As depicted in FIG. 14B, when a given force F is applied to the adjunct 1400 (e.g., in an x-direction), the spacer fibers 1406 slide along the first and second fibers 1402, 1404 (e.g., in a ±y-direction). This sliding action is due to the loose knot configuration of the first and second knots 1408, 1412. Consequently, the standing fibers 1416 slide and causes the top layer 1410 to move towards the bottom layer 1414. As a result, the adjunct 1400 compresses from an uncompressed state (FIG. 14A) with an uncompressed height $H_1$ to a first compressed state (FIG. 14B) with a first compressed height $H_2$. Thus, under a given force, the sliding of the spacer fibers 1406, and consequently, the standing fibers 1416, primarily effects the compression of the adjunct 1400 from the uncompressed height H to the first compressed height $H_2$.

Figure 15A:
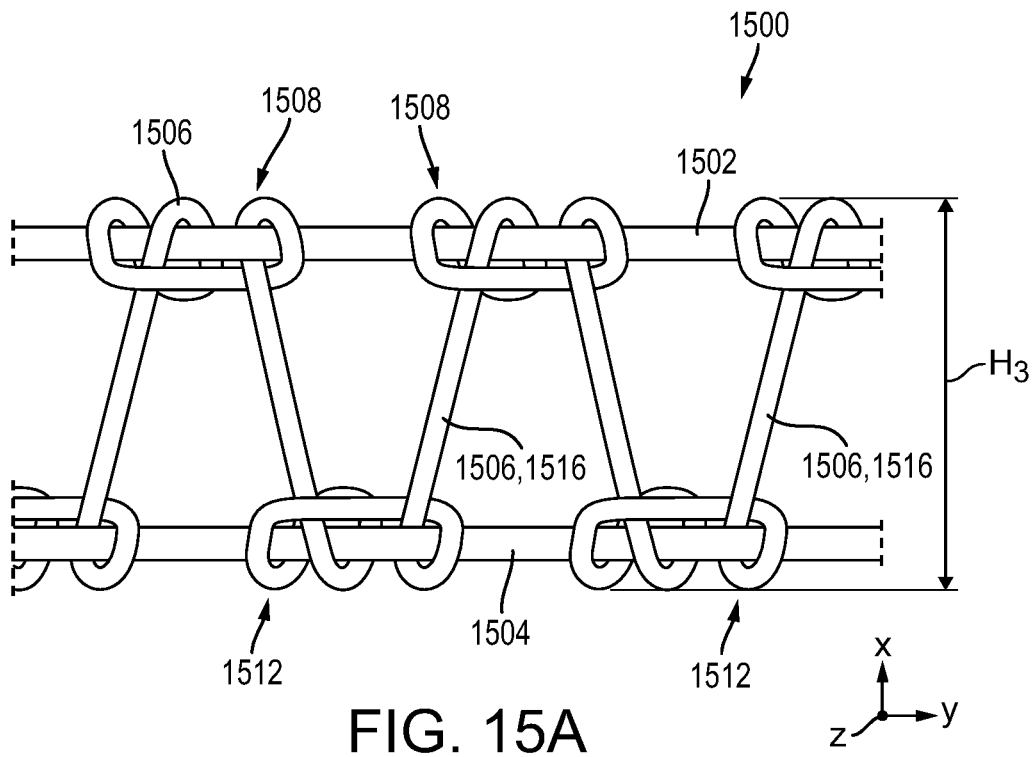
FIG. 15A is a cross-sectional view of an exemplary embodiment of a compressible knitted adjunct in an uncompressed state.
Figure 15B:
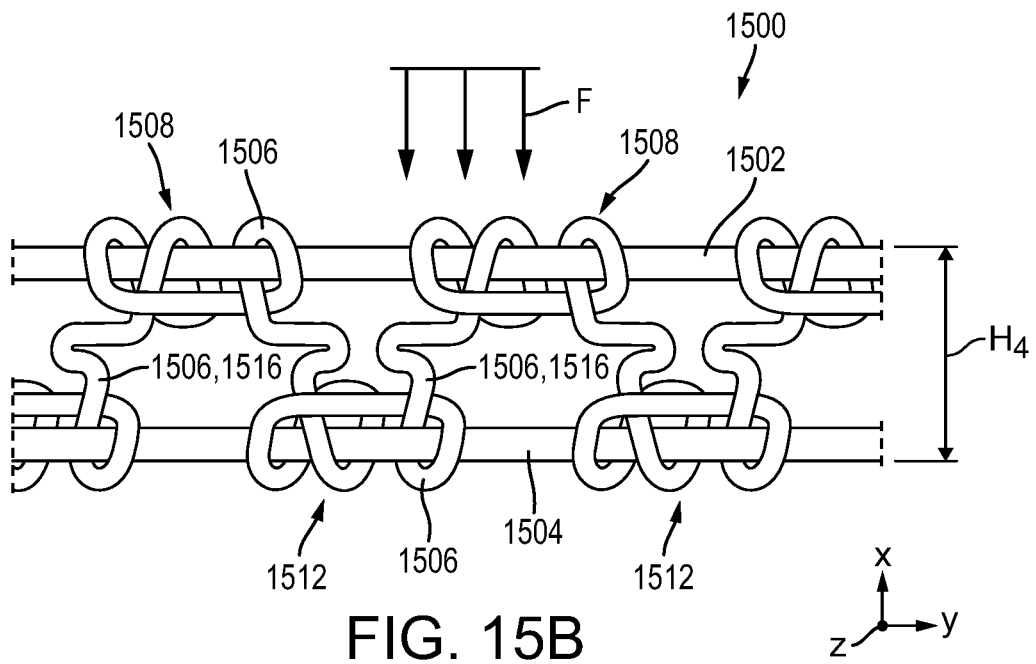
FIG. 15B is a cross-sectional view of the adjunct of FIG. 15A in a first compressed state.

In some embodiments, tighter knots can be used to interconnect the spacer fibers with the first fibers and the seconds second fibers, for example, as shown in FIGS. 15A-15B, to thereby increase the stiffness of the standing fibers, and thus the stiffness of the adjunct. Adjunct 1500 is similar to adjunct 1400 in FIGS. 14A-14B except that the first and second knots 1508, 1512 have a tighter knot configuration, and therefore common features are not described in detail herein.

As depicted in FIG. 15B, when a given force F is applied to the adjunct 1500 (e.g., in an x-direction), the tighter configuration of the knots 1508, 1512 inhibit the spacer fibers 1506 from sliding along the first and second fibers 1502, 1504, and thus prevent the standing fibers 1516 from respectively sliding. This imparts more rigidity to the standing fibers 1516, thereby increasing their stiffness. As a result, the standing fibers 1516 are stiffer compared to the standing fibers 1416 of FIGS. 14A-14B, and therefore this leads to a stiffer adjunct 1500 when compared to the adjunct 1400 of FIGS. 14A-14B. For example, when the same amount of force is applied to the adjunct 1500, the adjunct 1500 compresses from an uncompressed state (FIG. 14A) with an uncompressed height $H_3$ that is similar to uncompressed $H_1$ of adjunct 1400 to a second compressed state (FIG. 14B) with a second compressed $H_4$ that is larger than the first compressed height $H_2$ of adjunct 1400. This illustrates the impact that knot tightness can have on the compression of an adjunct.

Figure 16A:
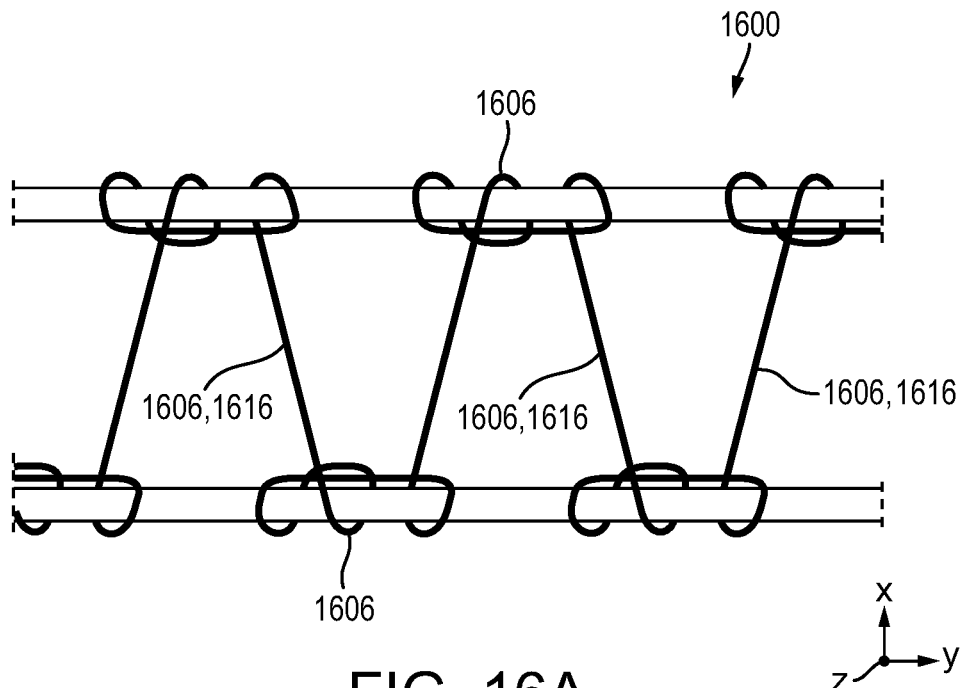
FIG. 16A is a cross-sectional view of an exemplary embodiment of a compressible knitted adjunct in an uncompressed state.
Figure 16B:
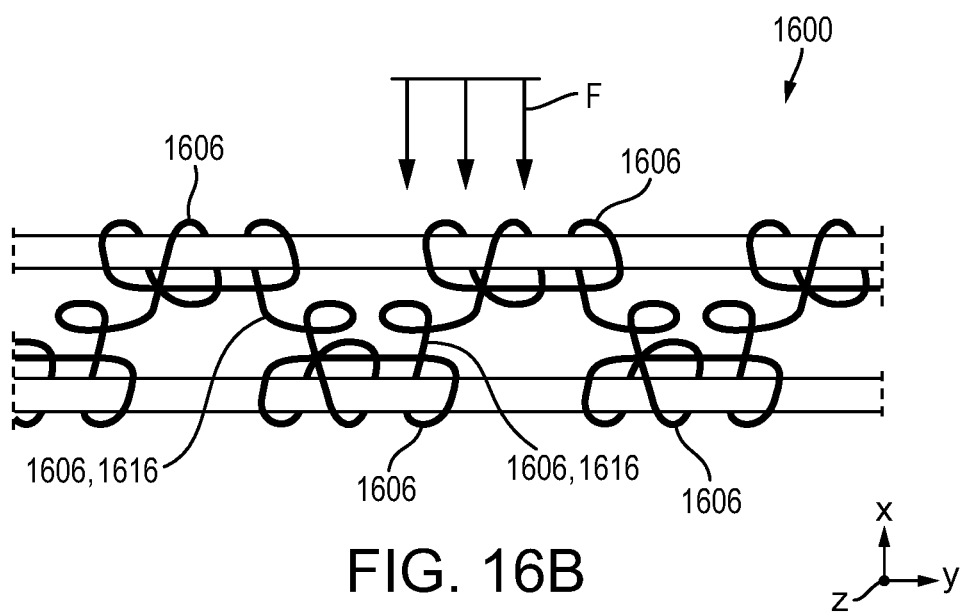
FIG. 16B is a cross-sectional view of the adjunct of FIG. 16A in a first compressed state.

Similarly, knot tightness can impart can impart partial rigidity to thinner spacer fibers, and thus, increase the overall stiffness of an adjunct, like adjunct 1600 in FIGS. 16A-16C. Adjunct 1600 is similar to adjunct 1500 in FIGS. 15A-15B except that the spacer fibers 1606 are thinner compared to spacer fibers 1506.

Figure 17A:
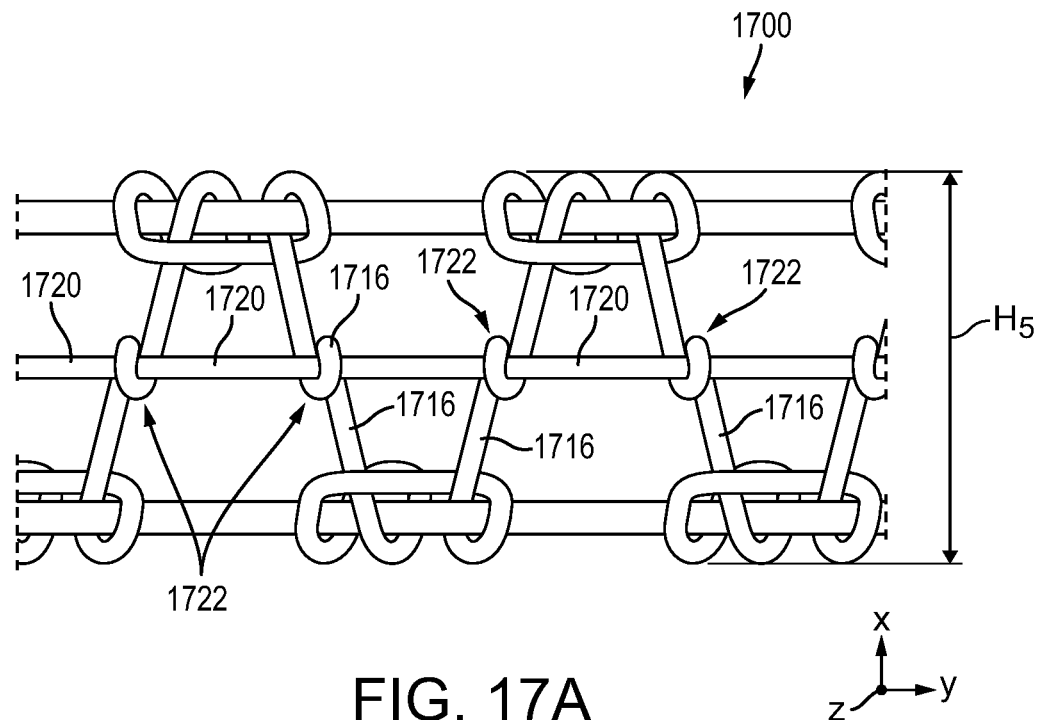
FIG. 17A is a cross-sectional view of an exemplary embodiment of a compressible knitted adjunct in an uncompressed state.
Figure 17B:
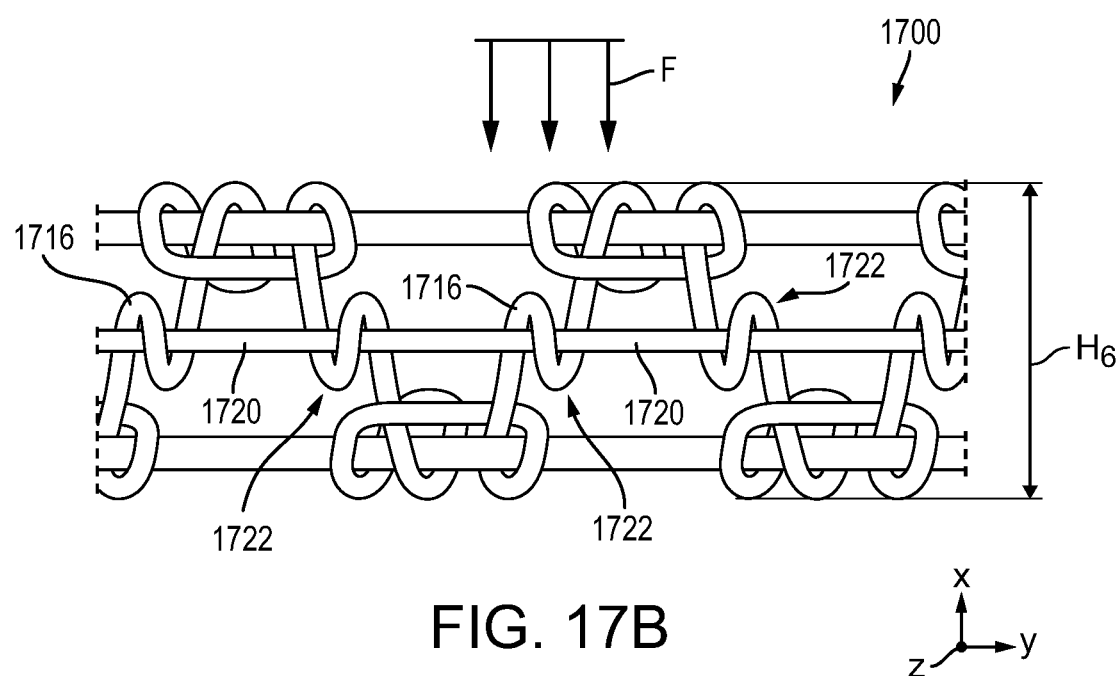
FIG. 17B is a cross-sectional view of the adjunct of FIG. 17A in a first compressed state.

In some embodiments, the intermediate layer of an adjunct can include reinforcing fibers that are interconnected with the standing fibers, which can further increase the stiffness of the adjunct, for example, as shown in FIGS. 17A-17B. Adjunct 1700 is similar to adjunct 1500 in FIGS. 15A-15B except that the standing fibers 1716 are multi-looped about reinforcing fibers 1720 at third interconnections 1722, in which the reinforcing fibers 1720 each extend mid-way through the intermediate layer 1718 (e.g., extending in the y-direction). As a result, for a given amount of force F, as shown in FIG. 17B, the adjunct 1700 will compress from an uncompressed state (FIG. 17A) with an uncompressed height $H_5$ that is similar to uncompressed $H_3$ of adjunct 1500 to a second compressed state (FIG. 17B) with a third compressed height $H_6$, which is larger than the second compressed height $H_4$ of adjunct 1500.

Figure 18A:
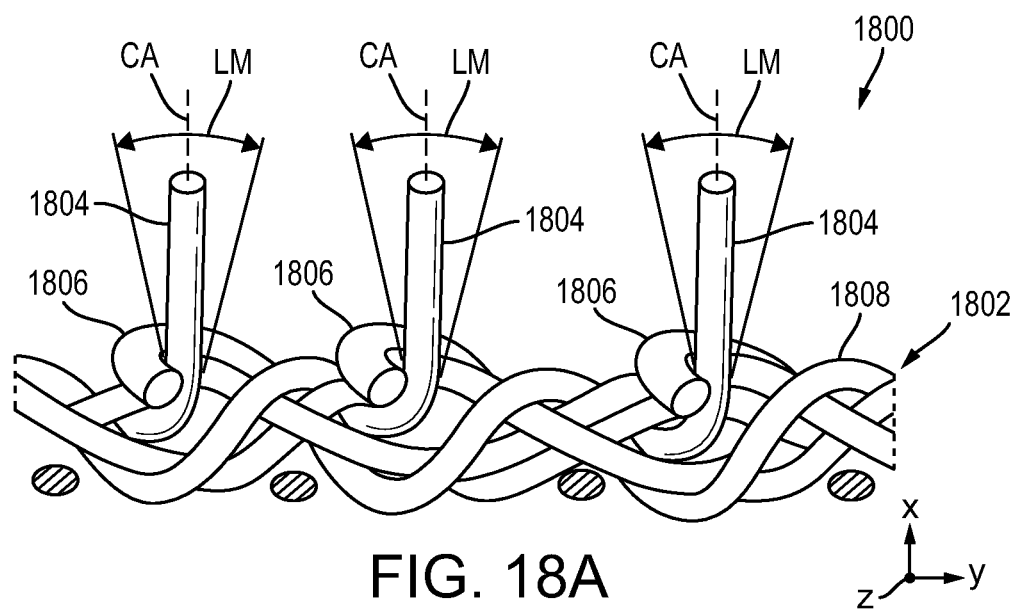
FIG. 18A is a side view of an exemplary embodiment of a compressible knitted adjunct having reinforcing knots.
Figure 18B:
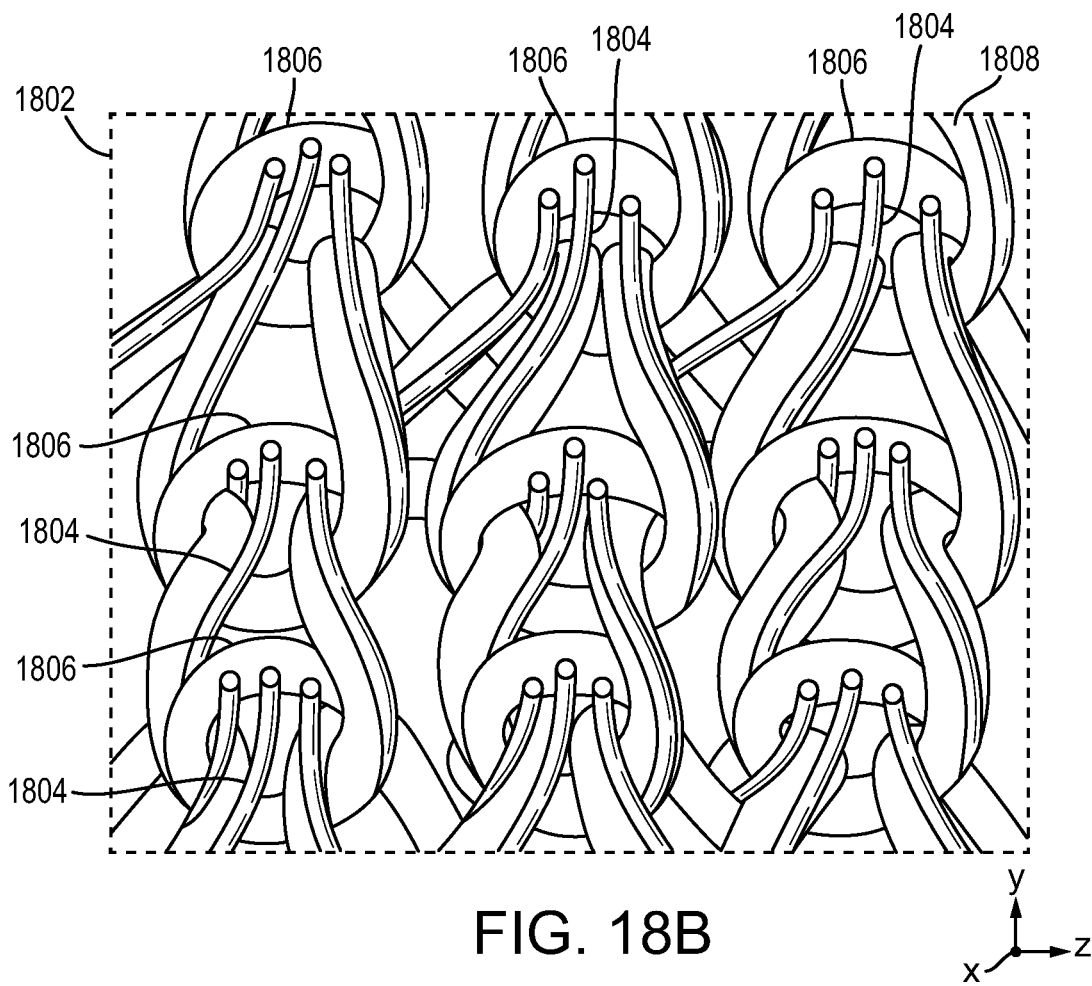
FIG. 18B is a bottom view of the knitted adjunct of FIG. 18A.

FIGS. 18A-18B illustrate another exemplary embodiment of a knitted adjunct 1800. The adjunct 1800 includes a layer 1802 formed of at least first fibers 1808, and a core layer formed of spacer fibers 1804 intertwined with and extending from the layer 1802. The layer 1802 can be a top layer (e.g., a tissue-contacting layer) or a bottom layer (e.g., a cartridge-contacting layer) of the adjunct 1800, with portions of the spacer fibers 1804 forming the core layer arranged between the top and bottom layers. In this illustrate embodiment, the portions of the spacer fibers 1804 that form the core layer extend between the top and bottom layers in a generally columnar configuration, meaning they are generally oriented in adjacent columns. For sake of simplicity, only a portion of the first fibers 1808 and of the spacer fibers 1804 is being illustrated. A person skilled in the art will appreciate that the following discussion is also applicable to the remaining first fibers and spacer fibers of the adjunct.

As shown in FIGS. 18A-18B, the spacer fibers 1804 extend along a central axis CA, outward from the layer 1802. The layer 1802 includes reinforcing fibers 1806, which are knotted to the spacer fibers 1804 and the first fibers 1808. The knotting of the reinforcing fibers 1806 can limit the lateral movement LM of the spacer fibers 1804 from the central axis CA of each spacer fiber 1804. This interaction between the spacer fibers 1804 and the reinforcing fibers 1806 affects the stiffness of the adjunct 1800. Since the spacer fibers 1804 have limited lateral movement LM, the spacer fibers 1804 have limited deformation abilities when the adjunct 1800 is compressed.

Figure 19A:
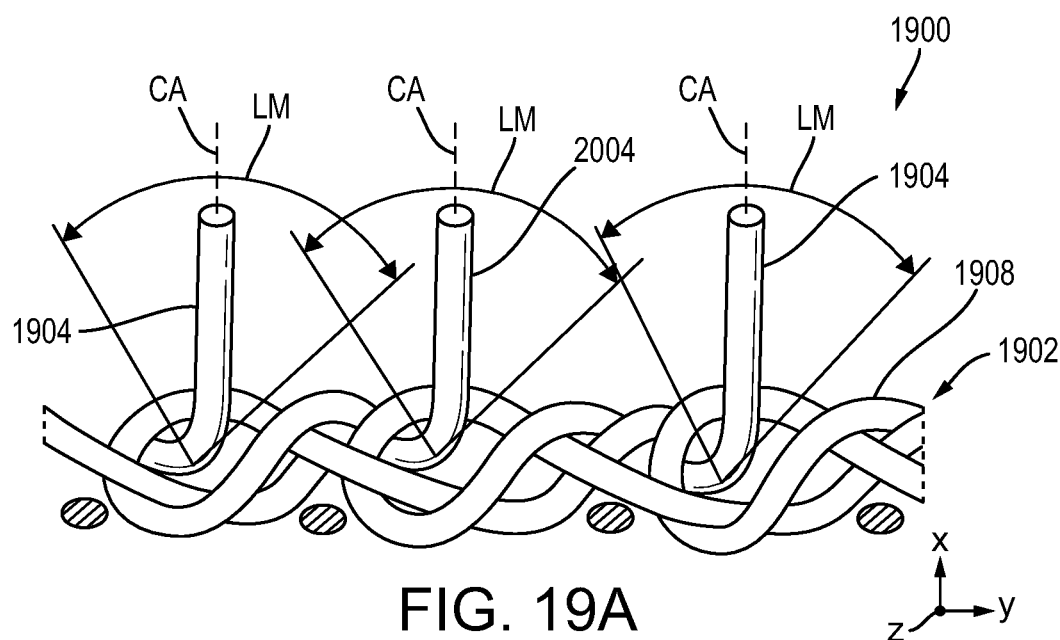
FIG. 19A is a side view of an exemplary embodiment of a compressible knitted adjunct without reinforcing knots.
Figure 19B:
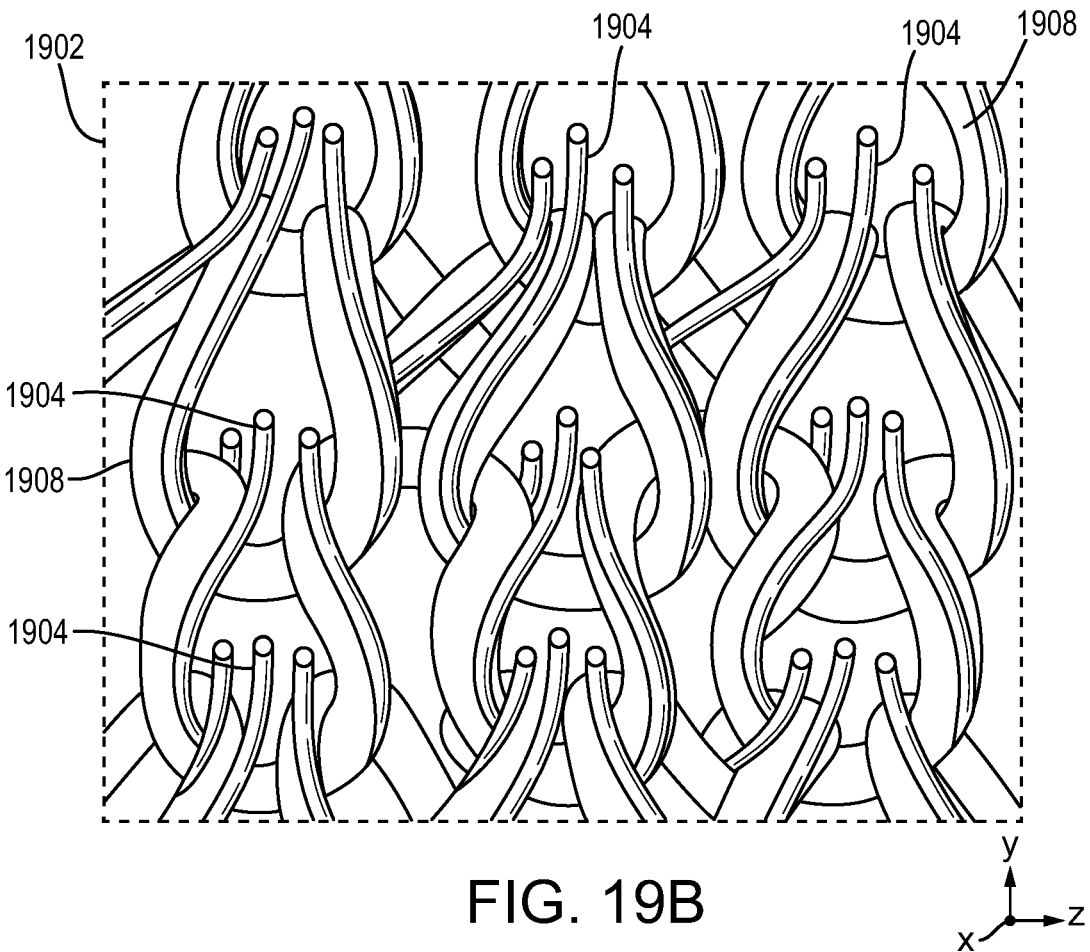
FIG. 19B is a bottom view of the knitted adjunct of FIG. 19A.

FIGS. 19A-19B illustrate another exemplary embodiment of a knitted adjunct 1900. The adjunct 1900 can be disposed on a top or deck surface of a staple cartridge. The adjunct 1900 includes a layer 1902 formed of at least first fibers 1908, and a core layer formed of spacer fibers 1904 intertwined with and extending from the layer 1902. The layer 1902 can be a top layer (e.g., a tissue-contacting layer) or a bottom layer (e.g., a cartridge-contacting layer) of the adjunct 1900, with the spacer fibers 1904 forming the core layer arranged between the top and bottom layers. In this illustrated embodiment, the portions of the spacer fibers 1904 that form the core layer extend between the top and bottom layers in a generally columnar configuration, meaning they are generally oriented in adjacent columns. For sake of simplicity, only a portion of the first fibers 1908 and of the spacer fibers 1904 is being illustrated. A person skilled in the art will appreciate that the following discussion is also applicable to the remaining first fibers and spacer fibers of the adjunct.

As shown in FIGS. 19A-19B, the spacer fibers 1904 extend along a central axis CA, outward from the layer 1902. The layer 1902 does not include any reinforcing fibers in contact with the spacer fibers 1904. Due to the lack of reinforcing fibers, the spacer fibers are less limited in their lateral movement LM from the central axis CA of each spacer fiber 1904 when compared to the adjunct 1800 of FIG. 18A. This interaction between the spacer fibers 1904 and the first fibers 1908, with any reinforcing fibers, affects the stiffness of the adjunct 1900. Since the spacer fibers 1904 have extended lateral movement LM, the spacer fibers 1904 have greater deformation abilities when compared to the adjunct 1800 of FIG. 18A when the adjunct 1900 is compressed.

Figure 20:
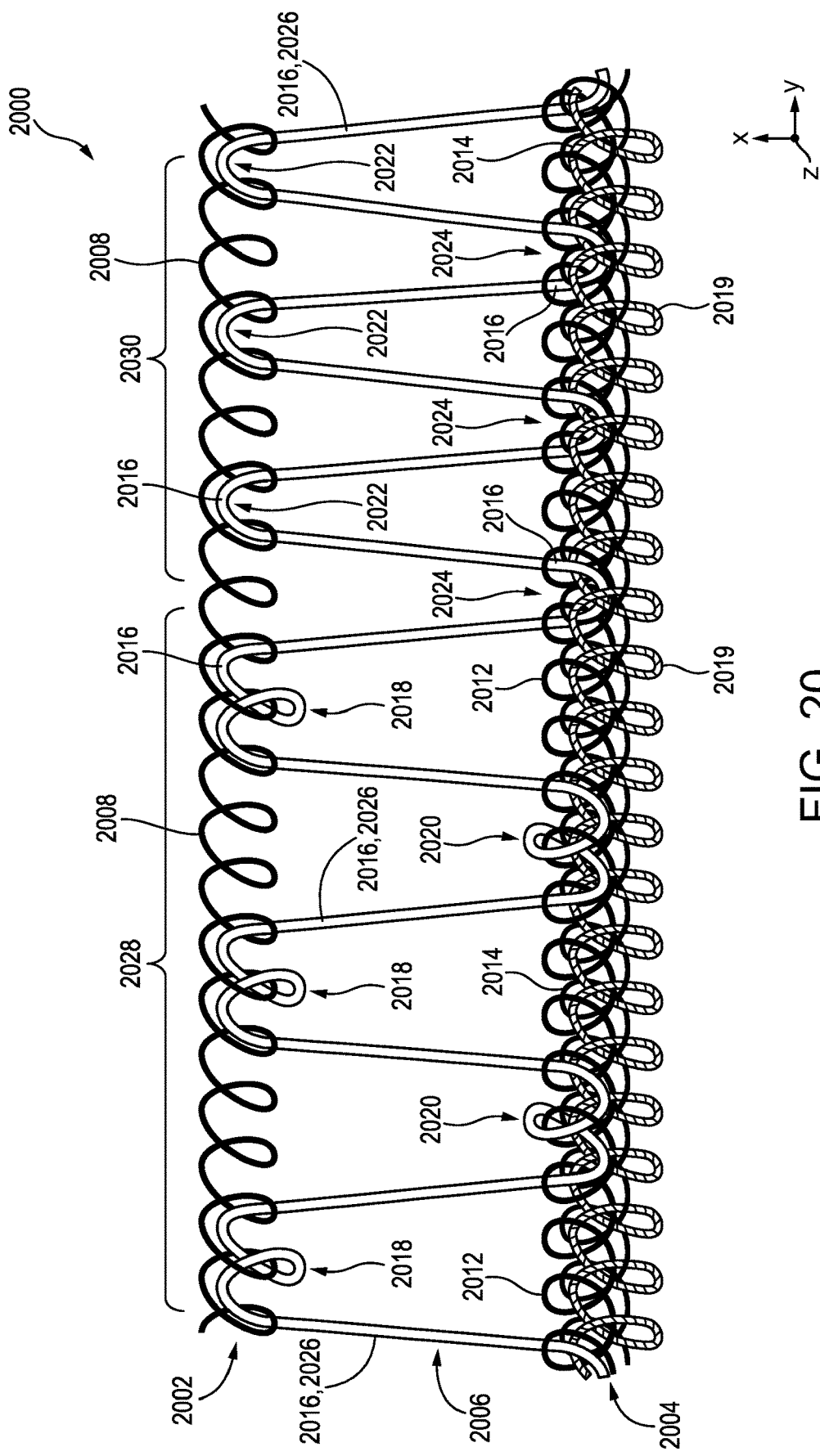
FIG. 20 is a cross-sectional view of another exemplary embodiment of a compressible knitted adjunct.

FIG. 20 illustrates another exemplary embodiment of a knitted adjunct 2000. The adjunct 2000 includes a top layer 2002 (e.g., a tissue-contacting layer) formed of at least first fibers 2008, a bottom layer 2004 (e.g., a cartridge-contacting layer) formed of at least second and third fibers 2012, 2014 and spacer fibers 2016 intertwined with and extending between the top and bottom layers 2002, 2004 to thereby connect the top and bottom layers 2002, 2004. The portions of the spacer fibers 2016 that extend between the top and bottom layers 2002, 2004 form a core layer 2006. For sake of simplicity, only one first fiber 2008, second fiber 2012, third fiber 2014, and spacer fiber 2016 is being illustrated. A person skilled in the art will appreciate that the following discussion is also applicable to the remaining first, second, third, and spacer fibers of the adjunct.

The top and bottom layers 2002, 2004 can have a variety of configurations. For example, as shown in FIG. 20, the bottom layer 2004 has a fiber density that is greater than the fiber density of the top layer 2002. In other embodiments, the top layer 2002 can have a greater fiber density than the bottom layer 2004. In some embodiments, the first fibers 2008 of the top layer 2002 can be knitted or woven into a first predetermined pattern and/or the second and third fibers 2012, 2014 of the bottom layer 2004 can be knitted or woven into a second predetermined pattern. In certain embodiments, the first and second predetermined patterns can be generally identical (e.g., nominally identical within manufacturing tolerances), whereas in other embodiments, the first and second predetermined patterns can be different. A person skilled in the art will appreciate that the first fibers 2008 and the second and third fibers 2012, 2014 can be randomly or repeatedly knitted or woven within the top and bottom layers 2002, 2004, respectively. As such, and for sake of simplicity, the top and bottom layers 2002, 2004 are generally illustrated, and thus the specific structural configurations of the top and bottom layers 2002, 2004 are not limited to what is depicted in the figures.

The first fibers 2008, the second fibers 2012, the third fibers, 2014 and the spacer fibers 2016 can have a variety of configurations. For example, in some embodiments, the first fibers 2008, the second fibers 2012, the third fibers 2014, and the spacer fibers 2016 can be generally identical (e.g., nominally identical within manufacturing tolerances) in material and/or structural configuration. In other embodiments, the first, second, and third fibers 2008, 2012, 2014 can be generally identical (e.g., nominally identical within manufacturing tolerances) in material and/or structural configuration relative to each other and the spacer fibers 2016 can be different relative thereto. For example, in certain embodiments, the first, second, third fibers 2008, 2012, 2014, can be multifilament fibers, and the spacer fibers 2016 can be monofilament fibers. As such, aside from the general overall shape, the specific structural configuration of each of the first fibers 2008, the second fibers 2012, the third fibers 2014, and the spacer fibers 2016 is not shown.

In certain embodiments, the first fibers 2008 can be formed of low friction fibers (e.g., monofilament fibers) that are knitted or woven to effect a substantiality smooth pattern to help retain the adjunct 2000 on a top or deck surface on a cartridge when tissue slides across the adjunct 2000, for example, when the adjunct 2000 is being placed at the stapling site. As such, employing low friction fibers within a top layer (e.g., tissue-contacting layer) of an adjunct can minimize the friction that would otherwise be created between the tissue and adjunct as the tissue slides across the adjunct prior to staple deployment.

As further shown, the bottom layer 2004 includes fourth fibers 2019 that can be configured to increase the friction between the adjunct 2000 and a top or deck surface of a cartridge. This can help retain the adjunct 2000 to the cartridge prior to staple deployment. The fourth fibers 2019 can have a variety of configurations. For example, in some embodiments, the fourth fibers can be multifilament fibers. As such, aside from the general overall shape, the specific structural configuration of the fourth fibers 2019 is not shown. Further, for sake of simplicity, only one fourth fiber 2019 is being illustrated.

The spacer fibers 2016 are interconnected within the first fibers 2008 at first and second interconnections 2018, 2022 within the top layer 2002, and the spacer fibers 2016 are interconnected with at least the second and third fibers 2012, 2014 at third and fourth interconnections 2020, 2024 within the bottom layer 2004. As such, this interaction between the top and bottom layers 2002, 2004 with that of the core layer 2006 secures the top layer 2002 to the bottom layer 2004. Further, the portions of spacer fibers that form the core layer 2006 are arranged in such a manner to form standing fibers 2026. The standing fibers 2026 can be have a variety of orientations within the core layer 2006, such as a generally columnar configuration, as shown, meaning they are generally oriented in adjacent columns. The standing fibers 2026 can be configured to bend or compress in response to force being applied to the adjunct 2000.

As shown in FIG. 20, the interconnections 2018, 2020, and 2022, 2024 can be identical between the top layer 2002 and the bottom layer 2004. The interconnections 2018, 2020 are represented as tight knots, with the spacer fibers 2016 wrapping around the first fibers 2008 of the top layer 2002 multiple times, while also wrapping around the second and third fibers 2012, 2014 of the bottom layer 2004. In some embodiments, even though the interconnections 2018, 2020 are depicted as tight knots formed by wrapping the spacer fibers 2016 around the first, second, and third fibers 2008, 2012, 2014, other types of tight knots for the interconnections 2018, 2020 can be used, such as any knot that prevents sliding of the spacer fibers 2016 to slide along the first, second, and third fibers 2008, 2012, 2014.

Additionally, the interconnections 2022, 2024 are represented as loose knots, with the spacer fibers 2016 passing through the first fibers 2008 of the top layer 2002 for a single pass, while also passing through the second and third fibers 2012, 2014 of the bottom layer 2004 for a single pass. In some embodiments, even though the interconnections 2022, 2024 are depicted as loose knots formed by wrapping the spacer fibers 2016 around the first, second, and third fibers 2008, 2012, 2014, other types of loose knots for the interconnections 2022, 2024 can be used, such as any knot that prevents sliding of the spacer fibers 2016 to slide along the first, second, and third fibers 2008, 2012, 2014.

Due to the presence of two different types of interconnections, the adjunct 2000 can have a first compression zone 2028 and a second compression zone 2030. Each compression zone can have a different stiffness when compressed, even though both compression zones are manufactured from the same fibers. This is because when the adjunct 2000 is compressed, the interconnections 2018, 2020 inhibit the spacer fibers 2016 from sliding along the first, second, and third fibers 2008, 2012, 2014, whereas, in contrast, the interconnections 2022, 2024 allow the spacer fibers 2016 to slide along the first, second, and third fibers 2008, 2012, 2014. As such, each different compression zone 2028, 2030 has a respective stiffness such that the adjunct 2000 can have a variable compression strength, for example, along its width (e.g., in a y-direction).

In certain embodiments, the spacer fibers can interact with at least a portion of the remaining fibers of the bottom layer (e.g., cartridge-contacting layer) of an adjunct in such a way that allows the spacer fibers to extend beyond the remaining fibers (e.g., in the form of loops) when the adjunct is compressed. Alternatively, or in addition, the spacer fibers can interact with at least a portion of the remaining fibers of the top layer (e.g., tissue-contacting layer) of an adjunct in such a way that allows the spacer fibers to extend beyond the remaining fibers (e.g., in the form of loops) when the adjunct is compressed.

In addition to fiber connectivity, the overall compression behavior of an adjunct can at least partially depend on the type of spacer fibers incorporated therein. As such, a desired compression behavior of the adjunct can be effected by at least incorporating spacer fibers having a particular structural configuration (e.g., monofilament or multifilament) and/or dimensions (e.g., diameter), and/or a particular compositional make-up (e.g., a first polymeric material having a low modulus of elasticity, a second polymeric material having a high modulus of elasticity, or a blend of two or more polymeric materials). Further, the compression behavior can be a function of the orientation of the portions of the spacer fibers within a core or intermediate layer of an adjunct (e.g., the direction the standing fibers extend relative to the longitudinal axis of the adjunct).

In some embodiments, different spacer fibers can be incorporated into different portions within the adjunct to effect different compression zones within the adjunct. For example, a first type of spacer fiber (e.g., first spacer fibers) can be selected to create a first compression zone and a second type of spacer fiber (e.g., second spacer fibers) that differs from the first type of spacer fiber can be selected to create a second compression zone. The first type of fiber can differ from the second type of fiber in structure (e.g., structure type, e.g., monofilament or multifilament, and/or in dimension, e.g., height and/or diameter) and/or composition. As such, the first compression zone has a first compression strength and the second compression zone has a second compression strength that is different than the second compression strength. As a result, the adjunct has a varied compression strength.

For example, the first compression zone can have a greater compression strength than the second compression zone, and therefore the first compression zone can be more stiff. In use, the first compression zone can at least partially overlap with a longitudinal slot formed in the cartridge which is configured to receive a cutting member and the second compression zone can at least partially overlap with staple cavities defined in the cartridge. Such an arrangement can facilitate the transection of the adjunct while providing desirable tissue thickness compensation properties within the staples that capture the adjunct against the tissue. In certain instances, the second compression can also partially overlap with one or more portions of the longitudinal slot. In one embodiment, the second compression zone can be the proximate-most zone to the beginning and/or end of the longitudinal slot.

Figure 21A:
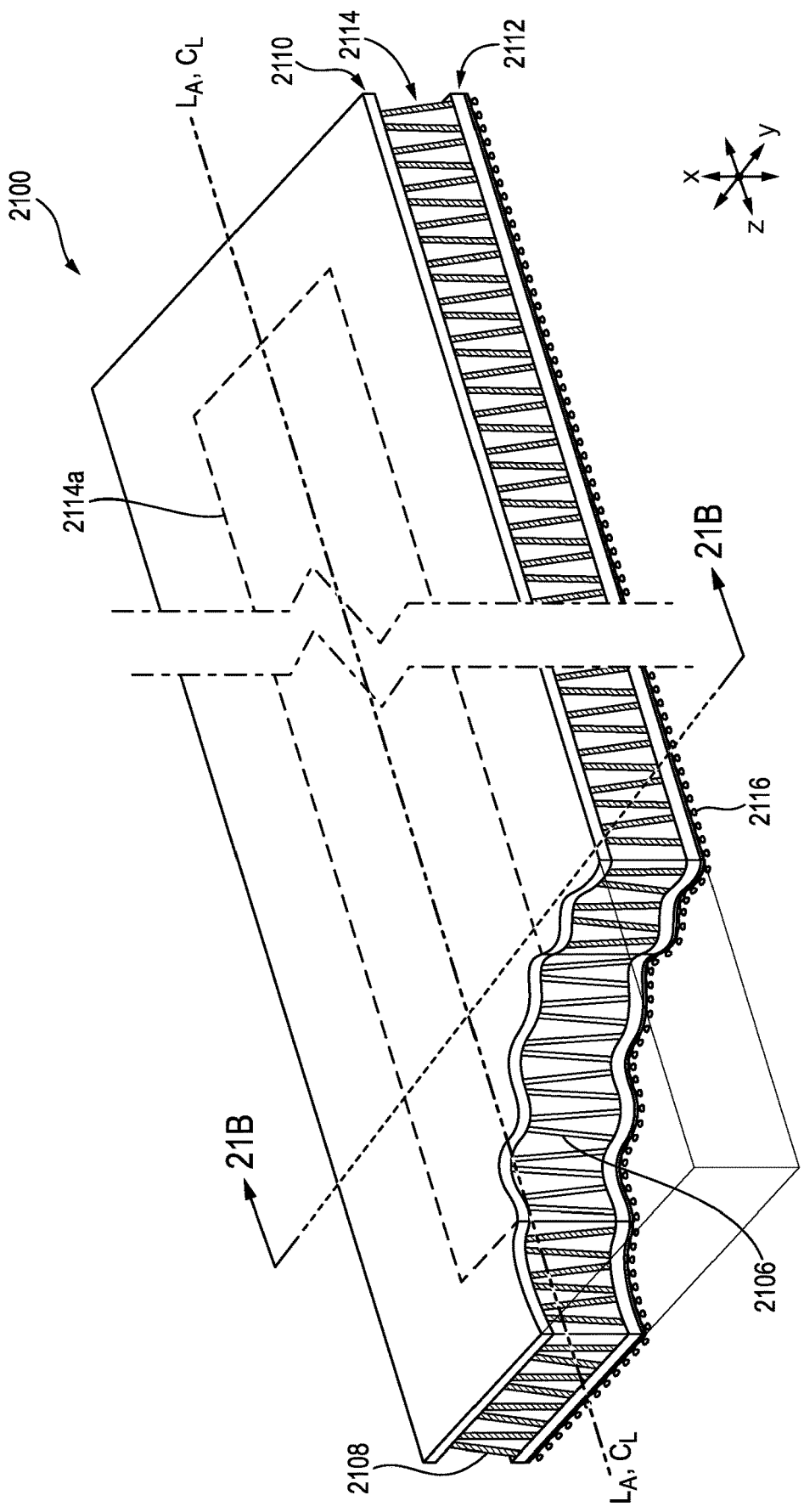
FIG. 21A is a perspective view of another exemplary embodiment of a compressible knitted adjunct.
Figure 21B:
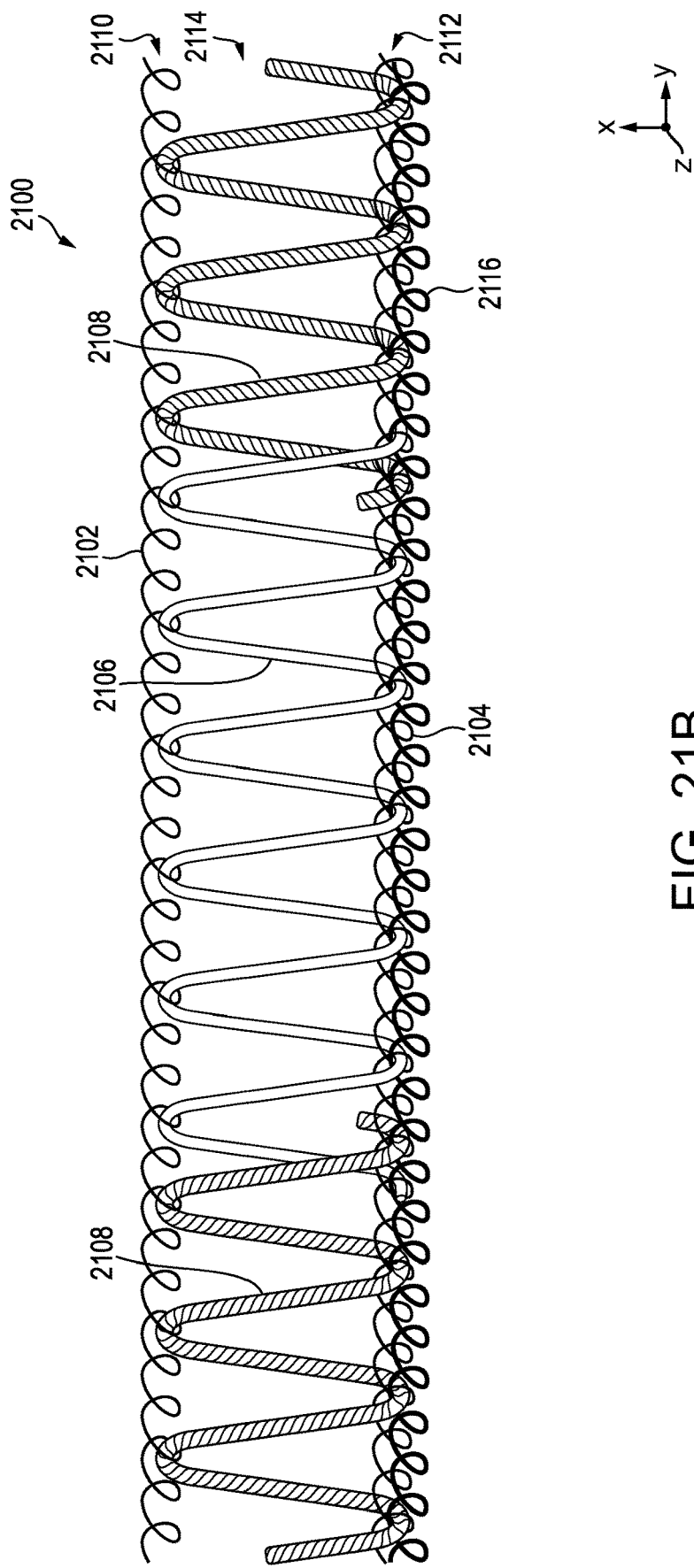
FIG. 21B is a cross-sectional view of the adjunct of FIG. 21A taken at line 21B-21B.

FIGS. 21A-21B is an exemplary embodiment of a knitted adjunct 2100 having two different types of spacer fibers. The adjunct 2100 includes first fibers 2102, second fibers 2104, first spacer fibers 2106, and second, different spacer fibers 2108 that are intertwined to form a top layer 2110 (e.g., a tissue-contacting layer), a bottom layer 2112 (e.g., a cartridge-contacting layer) and an intermediate layer 2114 that is positioned between the top and bottom layers 2110, 2112. As shown in FIG. 21A, the first spacer fibers 2106 are concentrated within a center portion of the intermediate layer 2114 (represented as a dotted box 2114a) and define a first compression zone of the adjunct 2100. The second spacer fibers 2108 are concentrated in the remaining portion of the intermediate layer 2114 and define a second compression zone within the adjunct 2100.

The first fibers 2102, the second fibers 2104, the first spacer fibers 2106, and the second spacer fibers 2108 can have a variety of configurations. For example, in some embodiments, the first fibers 2102 and the second fibers 2104 can be generally identical (e.g., nominally identical within manufacturing tolerances) in compositional makeup (e.g., formed of the same material(s)), dimension(s) (e.g., height and/or diameter), and/or in structural configuration (e.g., monofilament or multifilament). In other embodiments, the first and second fibers 2102, 2104 can be different. Further, the first fibers and/or second fibers can be the same as the first spacer fibers or the second spacer fibers. In some embodiments, the first fibers 2102, the second fibers 2104, the first spacer fibers 2106, and/or the second spacer fibers 2108 can be monofilament fibers. In other embodiments, the first fibers 2102, the second fibers 2104, the first spacer fibers 2106, and/or the second spacer fibers 2108 can be monofilament fibers. In certain embodiments, the first fibers 2102, the second fibers 2104, and the first spacer fibers 2106 can be monofilament fibers and the second spacer fibers 2108 are multifilament fibers. As such, aside from the general overall shape, the specific structural configuration of the first fibers 2102, the second fibers 2104, the first spacer fibers 2106, and the second spacer fibers 2108 are not shown.

In some embodiments, the first fibers 2102 of the top layer 2110 and/or second fibers 2104 of the bottom layer 2112 can be knitted in a respective predetermined pattern. In certain embodiments, the predetermined pattern of the first fibers 2102 within the top layer 2110 and the predetermined pattern of the second fibers 2104 of the bottom layer 2112 can be generally identical (e.g., nominally identical within manufacturing tolerances), whereas in other embodiments, the predetermined patterns can be different. Further, in some embodiments, the fiber density of the top layer 2110 can be different than the fiber density of the bottom layer 2112. While the first fibers 2102 of the top layer 2110 and the second fibers 2104 of the bottom layer 2112 can each be knitted in various patterns, in certain embodiments, the first fibers 2102 can be knitted into a first Raschel knit pattern and the second fibers 2104 can be knitted into a second Raschel knit pattern that is the same or different than the first Rachel knit pattern. A person skilled in the art will appreciate that the first fibers 2102 and the second fibers 2104 can be randomly or repeatedly knitted or woven within the top and bottom layers 2110, 2112, respectively. As such, and for sake of simplicity, the top and bottom layers 2110, 2112 are generally illustrated, and thus the specific structural configurations of the top and bottom layers 2110, 2112 are not limited to what is depicted in the figures.

As shown in FIGS. 21A-21B, the portions of the first spacer fibers 2106 and the portions of the second spacer fibers 2108 that extend between the top and bottom layers 2110, 2112 form the intermediate layer 2114. While these portions can have a variety of configurations, in this illustrated embodiment, they are arranged in a generally columnar configuration, meaning they are generally oriented in adjacent columns. The compression behavior of the adjunct 2100 can therefore be predominately driven by the buckling properties of the first and second spacer fibers 2106, 2108.

As further shown, the first compression zone 2114*a* is completely bordered by the second compression zone, and therefore the intended cut-line CL of the adjunct 2100 is defined across the first and second compression zones and along the longitudinal axis $L_A$ of the adjunct 2100. In this illustrated embodiment, the majority of the intended cut-line CL is defined by the first compression zone 2114*a*, and therefore can be configured to be stiffer, and thus exhibit a higher resistance to compression, compared to the second compression zone. For example, the first spacer fibers 2106 can be monofilament fibers and the second spacer fibers 2108 can be multifilament fibers. Thus, the resulting adjunct 2100 can have a variable compression strength in a lateral direction (e.g., the y-direction) relative to the cut-line CL of the adjunct 2100. Further, the beginning and end of the cut-line CL is defined by the second compression zone, which can therefore make cutting of the adjunct 2100 easier.

In some embodiments, the bottom layer 2112 can also be formed of one or more additional fibers 2116, as shown in more detail FIG. 21B. While the one or more additional fibers 2116 can have a variety of configurations, in this illustrated embodiment, the one or more additional fibers are interconnected within the bottom layer 2112 in such a way to form loops (e.g., traction loops) that provide traction against a top or deck surface of a cartridge to thereby help retain the adjunct to the cartridge prior to staple deployment. Alternatively, or in addition, the one or more additional fibers 2116 can be incorporated into the adjunct for purposes of thermoforming or bonding the adjunct to a cartridge. The one or more additional fibers 2116 can be multifilament or monofilament fibers. In one embodiment, the one or more additional fibers 2116 are multifilament fibers. In certain embodiments, the one or more additional fibers 2116 can include at least two first and second additional fibers, in which the first additional fiber differs from the second additional fiber in compositional makeup (e.g., formed of the same material(s)), dimension(s) (e.g., height and/or diameter) and/or in structural configuration (e.g., monofilament or multifilament).

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of a device. Other spatial terms such as "front" and "rear" similarly correspond respectively to distal and proximal. It will be further appreciated that for convenience and clarity, spatial terms such as "vertical" and "horizontal" are used herein with respect to the drawings.

However, surgical devices are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A stapling assembly for use with a surgical stapler, comprising:
    a cartridge having a plurality of staples disposed therein, the plurality of staples being configured to be deployed into tissue; and
    a knitted adjunct configured to be releasably retained on the cartridge such that the adjunct can be attached to tissue by the plurality of staples in the cartridge, the adjunct having a first end, a second end, and a longitudinal axis extending therebetween, the adjunct comprising at least one knitted layer formed of first fibers and at least one core layer formed of second fibers that are interconnected with the first fibers to form a plurality of interconnections, wherein one of the plurality of interconnections differs from at least another one of the plurality of interconnections to provide a variable compression strength;
    wherein the one of the plurality of interconnections that differs from the at least another one of the plurality of interconnections differs in at least one of a lateral direction and a longitudinal direction relative to the longitudinal axis of the adjunct.

2. The stapling assembly of claim 1, wherein the plurality of interconnections includes a first plurality of interconnections and a second plurality of interconnections.

3. A stapling assembly for use with a surgical stapler, comprising:
    a cartridge having a plurality of staples disposed therein, the plurality of staples being configured to be deployed into tissue; and
    a knitted adjunct configured to be releasably retained on the cartridge such that the adjunct can be attached to tissue by the plurality of staples in the cartridge, the adjunct having a first end, a second end, and a longitudinal axis extending therebetween, the adjunct comprising at least one knitted layer formed of first fibers and at least one core layer formed of second fibers that are interconnected with the first fibers to form a plurality of interconnections, wherein one of the plurality of interconnections differs from at least another one of the plurality of interconnections to provide a variable compression strength;
    wherein the plurality of interconnections includes a first plurality of interconnections and a second plurality of interconnections, and wherein the first plurality of interconnections each have a first tightness, and wherein the second plurality of interconnections each have a second tightness that is greater than the first tightness.

4. The stapling assembly of claim 3, wherein the cartridge includes a slot formed therein and extending along at least a portion of a longitudinal axis thereof, and wherein the first plurality of interconnections are proximate to the slot relative to the second plurality of interconnections.

5. The stapling assembly of claim 2, wherein the first plurality of interconnections are present in a first amount, and wherein the second plurality of interconnections are present in a second amount that is greater than the first amount.

6. The stapling assembly of claim 1, wherein the at least one knitted layer includes third fibers that interconnected with the first fibers and second fibers.

7. The stapling assembly of claim 1, wherein the second fibers are monofilament fibers.

8. The stapling assembly of claim 1, wherein the at least one knitted layer includes a first knitted layer that is configured to contact the cartridge.

9. The stapling assembly of claim 8, wherein the at least one knitted layer includes a second knitted layer that is configured to contact tissue, and wherein the at least one core layer is positioned therebetween.

10. The stapling assembly of claim 1, wherein the core layer further comprises third fibers that are interconnected with the second fibers.

11. A stapling assembly for use with a surgical stapler, comprising:
    a cartridge having a plurality of staples disposed therein, the plurality of staples being configured to be deployed into tissue; and
    a knitted adjunct configured to be releasably retained on the cartridge such that the adjunct can be attached to tissue by the plurality of staples in the cartridge, the adjunct having a first end, a second end, and a longitudinal axis extending therebetween, wherein the adjunct comprises at least two different compression zones, each compression zone being formed of first fibers and second fibers that are interconnected to each other at knots, wherein the knots of a first compression zone of the at least two different compression zones each have a first knot tightness and the knots of a second compression zone of the at least two different compression zones each have a second knot tightness that is greater than the first knot tightness such that the adjunct has a varying compression strength;

wherein at least one of the first compression zone and the second compression zone includes third fibers that are interconnected to the second fibers.

12. The stapling assembly of claim 11, wherein the second compression zone is positioned about at least a portion of a perimeter of the adjunct, and wherein the first compression zone is internal to the perimeter.

13. The stapling assembly of claim 11, the first compression zone has a first fiber density and the second compression zone has a second fiber density that is different than the first fiber density.

14. The stapling assembly of claim 11, wherein the cartridge includes a slot formed therein and extending along at least a portion of a longitudinal axis thereof, and wherein the first compression zone is configured to at least partially overlap with the slot when the adjunct is attached to the cartridge.

15. The stapling assembly of claim 11, wherein the second compression zone is configured to at least partially overlap with at least a portion of the plurality of staple when the adjunct is attached to the cartridge.

16. The stapling assembly of claim 11, wherein the knots of the first compression zone are present therein at a first frequency and the knots of the second compression zone are present therein at a second frequency that is different than the first frequency.

17. A stapling assembly for use with a surgical stapler, comprising:

a cartridge having a plurality of staples disposed therein, the plurality of staples being configured to be deployed into tissue; and a knitted adjunct configured to be releasably retained on the cartridge such that the adjunct can be attached to tissue by the plurality of staples in the cartridge, the adjunct having a first end, a second end, and a longitudinal axis extending therebetween, the adjunct comprising a tissue-contacting layer formed of at least first fibers, a cartridge-contacting layer formed of at least second fibers, and a core layer disposed between the tissue-contacting layer and the cartridge-contacting layer, the core layer being formed of third fibers that are interconnected with the first fibers at a first tightness and with the second fibers at a second tightness that is different than the first tightness to allow the adjunct to compress in a first predetermined direction and to limit movement in a second direction that differs from the first predetermined direction;

wherein at least one of the tissue-contacting layer and the cartridge-contacting layer includes reinforcing fibers that are knotted to the second fibers to minimize lateral movement of the second fibers relative to the longitudinal axis of the adjunct.

18. The stapling assembly of claim 17, wherein the first tightness is greater than the second tightness.

19. The stapling assembly of claim 17, wherein the first tightness is less than the second tightness.

\* \* \* \* \*